United States Patent
Armstrong

(10) Patent No.: US 10,781,433 B2
(45) Date of Patent: Sep. 22, 2020

(54) METHODS AND COMPOSITIONS FOR TREATMENT OF LAFORA DISEASE

(71) Applicant: Valerion Therapeutics, LLC, Concord, MA (US)

(72) Inventor: Dustin D. Armstrong, Quincy, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 0 days.

(21) Appl. No.: 16/332,331

(22) PCT Filed: Sep. 8, 2017

(86) PCT No.: PCT/US2017/050787
§ 371 (c)(1),
(2) Date: Mar. 11, 2019

(87) PCT Pub. No.: WO2018/049237
PCT Pub. Date: Mar. 15, 2018

(65) Prior Publication Data
US 2019/0316104 A1    Oct. 17, 2019

Related U.S. Application Data

(60) Provisional application No. 62/553,048, filed on Aug. 31, 2017, provisional application No. 62/385,656, filed on Sep. 9, 2016.

(51) Int. Cl.
| | | |
|---|---|---|
| *C12N 9/26* | (2006.01) | |
| *C07K 16/28* | (2006.01) | |
| *C07K 16/44* | (2006.01) | |
| *C12N 9/16* | (2006.01) | |
| *A61K 38/00* | (2006.01) | |

(52) U.S. Cl.
CPC ............ *C12N 9/2414* (2013.01); *C07K 16/28* (2013.01); *C07K 16/44* (2013.01); *C12N 9/16* (2013.01); *A61K 38/00* (2013.01); *C07K 2317/24* (2013.01); *C07K 2317/55* (2013.01); *C07K 2317/77* (2013.01)

(58) Field of Classification Search
None
See application file for complete search history.

(56) References Cited

U.S. PATENT DOCUMENTS

2013/0273026 A1    10/2013  Gavini et al.

FOREIGN PATENT DOCUMENTS

| WO | WO 2010/148010 A1 | 12/2010 |
| WO | WO 2015/106290 A1 | 7/2015 |
| WO | WO 2015/192092 A1 | 12/2015 |

OTHER PUBLICATIONS

International Search Report in International Application No. PCT/US2017/050787, dated Jan. 4, 2018.
Hansen, James E., Richard H. Weisbart, and Robert N, Nishimura. "Antibody mediated transduction of therapeutic proteins into living cells." *The Scientific World Journal* 5 (2005): 782-788.
Nikaido, Toru, James Austin, and Hans Stukenbrok. "Studies in myoclonus epilepsy III. The effects of arnylolytic enzymes on the ultrastructure of Lafora bodies." *Journal of Histochemistry & Cytochemistry* 19.6 (1971): 382-385.
Austin, Grant L., et al. "Central nervous system delivery and biodistribution analysis of an antibody—enzyme fusion for the treatment of Lafora disease." *Molecular pharmaceutics* 16.9 (2019): 3791-3801.
Brewer, M. Kathryn, et al. "Targeting pathogenic Lafora bodies in Lafora disease using an antibody-enzyme fusion." *Cell metabolism* 30.4 (2019): 689-705.

*Primary Examiner* — Kagnew H Gebreyesus
(74) *Attorney, Agent, or Firm* — Morse, Barnes-Brown & Pendleton, P.C.; Lisa M. Warren, Esq.

(57) ABSTRACT

In certain embodiments, the present disclosure provides compositions and methods for treating Lafora Disease.

22 Claims, 10 Drawing Sheets
Specification includes a Sequence Listing.

8 Vehicle Side (L)　　#8 FAB-amylase Side (R)

Very dark pink staining is over accumulated glycogen

7 Vehicle Side (L) #7 FAB-amylase Side (R)

Smaller light purple fibers (fast) and larger more clear fibers (slow) just represent normal fiber type differences

10 Vehicle Side (R)

10 Vehicle Side (L)

METHODS AND COMPOSITIONS FOR TREATMENT OF LAFORA DISEASE

RELATED APPLICATION

This application is a national stage filing under 35 U.S.C. 371 of International Application No. PCT/US2017/050787, filed Sep. 8, 2017, which claims the benefit of U.S. Provisional Application No. 62/385,656, filed Sep. 9, 2016, and U.S. Provisional Application No. 62/553,048, filed Aug. 31, 2017. The entire teachings of the above applications are incorporated herein by reference.

BACKGROUND OF THE DISCLOSURE

Glycogen storage diseases and glycogen metabolism disorders are a series of diseases that are caused by defects in basic metabolizing enzymes, thereby resulting in defects in glycogen synthesis or breakdown within muscles, liver, neurons and other cell types. Glycogen storage diseases may be either genetic (usually as autosomal recessive disorders) or acquired (e.g., by intoxication with alkaloids) (Monga et al.,). There are a number of different types of glycogen storage diseases, including GSDs Types I-XI, GSD Type 0, as well as Lafora disease which is often termed a glycogen metabolism disorder. These diseases differ with regard to the enzyme that is mutated and/or primary tissue affected (Monga et al., 2011, Molecular Pathology of Liver Diseases, Molecular Pathology Library 5, Chapter 45; and Gentry, et al., 2013, FEBS J, 280(2):525-37).

Lafora Disease, also called Lafora progressive myoclonic epilepsy or MELF, is a rare, fatal neurodegenerative disorder characterized by the accumulation of insoluble, poorly branched, hyperphosphorylated glycogen in cells from most tissues of affected individuals, including the brain, heart, liver, muscle and skin. Lafora Disease patients typically first develop symptoms in adolescence. Symptoms include temporary blindness, depression, seizures, drop attacks, myoclonus, ataxia, visual hallucinations, and quickly developing and severe dementia. Death usually occurs 2-10 years (5 years mean) after onset.

The prevalence of Lafora Disease is unknown. While this disease occurs worldwide, it is most common in Mediterranean countries, parts of Central Asia, India, Pakistan, North Africa and the Middle East. In Western countries, the prevalence is estimated to be below 1/1,000,000.

Lafora Disease is an autosomal recessive disorder caused by mutations in one of two genes: EPM2A and EPM2B. EPM2A encodes for the 331 amino acid protein known as laforin, which comprises an amino-terminal carbohydrate binding module and a carboxy-terminal dual specificity phosphatase domain. EPM2B encodes for the E3 ubiquitin ligase known as malin. Together, laforin and malin make up a functional complex which is believed to be involved in negatively regulating glucose uptake by modulating the subcellular localization of glucose transporters. Singh et al., 2012, Mol Cell Biol, 32(3):652-663. Recent studies also suggest that the accumulation of glycogen is responsible for neurodegeneration and impaired autophagy observed in the brains of Lafora patients. Duran et al., 2014, Hum Mol Genet, 23(12): 3147-56.

While the seizures and myoclonus can be managed, at least in early stages of the disease, with antiepileptic medications, there is currently no cure or effective treatment for patients having Lafora Disease.

SUMMARY OF THE DISCLOSURE

There is a need in the art for methods and compositions for clearing glycogen build-up, particularly cytoplasmic glycogen build-up, or for treating the cytotoxic effects associated with glycogen build-up, in patients with glycogen storage diseases and glycogen metabolism disorders (e.g., Forbes-Cori and/or Andersen Disease and/or von Gierke Disease and/or Pompe Disease and/or Lafora Disease) as well as a need for alternative therapies for treating these diseases or disorders. The present disclosure provides such methods and compositions. For example, there exists a need for decreasing glycogen accumulation in, for example, cytoplasm of cells, such as muscle (e.g. cardiac and/or diaphragm) and/or liver and/or neuronal cells (e.g., brain cells). By way of further example, such methods and compositions may decrease cytoplasmic glycogen accumulation. Accordingly, throughout the application, references to clearing glycogen build-up or decreasing glycogen accumulation (or like terms) encompass, unless otherwise specified, clearing or decreasing excess (e.g., beyond normal physiological level) glycogen, including clearing or decreasing excess glycogen present in an abnormal form (e.g., polyglucosan). In certain embodiments, the disclosure provides methods of clearing or decreasing excess polyglucosan (e.g., clearing or decreasing polyglucosan accumulation), such as in cytoplasm, such as in one or more of muscle cells (skeletal and/or cardiac), diaphragm, or neurons. In certain embodiments, clearing glycogen build-up or decreasing glycogen accumulation (or like terms) refers to doing so in, at least, cytoplasm of one or more affected cells. In certain embodiments, clearing glycogen build-up or decreasing glycogen accumulation, such as in, at least, cytoplasm, is or comprises clearing polyglucosan build-up or decreasing polyglucosan accumulation, such as in, at least, cytoplasm. Such methods and compositions would improve treatment of diseases or disorders such as Lafora Disease, particularly in patients whose disease is severe enough and/or advanced enough to have significant abnormal cytoplasmic glycogen accumulation (e.g., of normal and/or abnormal glycogen). The present disclosure provides such methods and compositions. In certain embodiments, the methods and compositions provided herein decrease glycogen build-up (e.g., such as clear glycogen build-up or decrease glycogen accumulation) in, at least, the cytoplasm. In certain embodiments, the methods and compositions of the present disclosure decrease polyglucosan build-up (e.g., build-up in, at least, the cytoplasm of cell(s), such as muscle and/or liver and/or diaphragm, and/or neuronal cell(s)). In certain embodiments, the methods and compositions of the present disclosure decrease glycogen, such as polyglucosan, build-up in, at least, cytoplasm of, at least muscle and/or neuronal cells.

In some embodiments, the disclosure provides for a chimeric polypeptide comprising: (i) an alpha-amylase polypeptide, and (ii) an internalizing moiety; wherein the alpha-amylase polypeptide comprises the amino acid sequence of SEQ ID NO: 1; and wherein the internalizing moiety is an antibody or antigen binding fragment, wherein the antibody or antigen binding fragment comprises a heavy chain variable domain and a light chain variable domain; wherein the heavy chain variable domain comprises the amino acid sequence of SEQ ID NO: 2; and wherein the light chain variable domain comprises the amino acid sequence of SEQ ID NO: 3. In some embodiments, the disclosure provides for a chimeric polypeptide comprising: (i) an alpha-amylase polypeptide, and (ii) an internalizing moiety; wherein the alpha-amylase polypeptide comprises the amino acid sequence of SEQ ID NO: 1, but wherein the alpha-amylase polypeptide does not comprise the full-length alpha-amylase polypeptide of SEQ ID NO: 36; and wherein the internalizing moiety is an antibody or antigen binding fragment, wherein the antibody or antigen binding fragment comprises a heavy chain comprising a heavy chain variable domain and a light chain comprising a light chain variable domain; wherein the heavy chain variable domain comprises the amino acid sequence of SEQ ID NO: 2; and wherein the light chain variable domain comprises the amino acid sequence of SEQ ID NO: 3. In some embodiments, the alpha-amylase polypeptide consists of the amino acid sequence of SEQ ID NO: 1. In some embodiments, the heavy chain comprises the leader sequence of SEQ ID NO: 4. In some embodiments, the light chain comprises the leader sequence of SEQ ID NO: 5. In some embodiments, the chimeric polypeptide has alpha-1,4-glucosidic bonds hydrolytic activity. In some embodiments, the chimeric polypeptide is capable of hydrolyzing alpha-1,4-glucosidic bonds in a cell-free system. In some embodiments, the chimeric polypeptide is capable of hydrolyzing alpha-1,4-glucosidic bonds in a cell from a subject having Lafora Disease. In some embodiments, the subject is a non-human animal. In some embodiments, the non-human animal is a mouse. In some embodiments, the subject is a human. In some embodiments, the cell is in vitro. In some embodiments, the cell is a muscle cell. In some embodiments, the cell is a diaphragm muscle cell. In some embodiments, the cell is a brain cell. In some embodiments, the cell is a neuron. In some embodiments, the alpha-amylase polypeptide is chemically conjugated to the internalizing moiety. In some embodiments, the chimeric polypeptide comprises a fusion protein comprising the alpha-amylase polypeptide and all or a portion of the internalizing moiety. In some embodiments, the chimeric polypeptide does not include a linker interconnecting the alpha-amylase polypeptide to the internalizing moiety. In some embodiments, the fusion protein comprises a linker. In some embodiments, the linker conjugates or joins the alpha-amylase polypeptide to the internalizing moiety. In some embodiments, the linker is a cleavable linker. In some embodiments, the linker comprises the amino acid sequence of SEQ ID NO: 6. In some embodiments, all or a portion of the internalizing moiety is conjugated or joined, directly or via a linker, to the N-terminal amino acid of the alpha-amylase polypeptide. In some embodiments, wherein all or a portion of the internalizing moiety is conjugated or joined, directly or via a linker, to the C-terminal amino acid of the alpha-amylase polypeptide. In some embodiments, all or a portion of the internalizing moiety is conjugated or joined, directly or indirectly to an internal amino acid of the alpha-amylase polypeptide. In some embodiments, the internalizing moiety promotes delivery of the chimeric polypeptide into cells via an equilibrative nucleoside transporter (ENT) transporter. In some embodiments, the internalizing moiety promotes delivery of the chimeric polypeptide into cells via ENT2. In some embodiments, the internalizing moiety promotes delivery of the chimeric polypeptide into a muscle cell. In some embodiments, the muscle cell is a diaphragm muscle cell. In some embodiments, the internalizing moiety promotes delivery of the chimeric polypeptide into a neuronal cell. In some embodiments, the neuronal cell is a brain neuronal cell. In some embodiments, the internalizing moiety comprises an antibody. In some embodiments, the antibody is a monoclonal antibody. In some embodiments, the internalizing moiety comprises an antigen-binding fragment. In some embodiments, the antigen-binding fragment is a Fab. In some embodiments, the antigen-binding fragment is a Fab'. In some embodiments, the antigen-binding fragment is an scFv. In some embodiments, the chimeric polypeptide is produced recombinantly. In some embodiments, the chimeric polypeptide is produced in a prokaryotic or eukaryotic cell. In some embodiments, the eukaryotic cell is selected from a yeast cell, an avian cell, an insect cell, or a mammalian cell. In some embodiments, one or more glycosylation groups are conjugated to the chimeric polypeptide. In some embodiments, the chimeric polypeptide comprises the amino acid sequence of SEQ ID NO: 7. In some embodiments, the chimeric polypeptide comprises the amino acid sequence of SEQ ID NO: 8. In some embodiments, the chimeric polypeptide comprises the amino acid sequence of SEQ ID NOs: 7 and 8. In some embodiments, the chimeric polypeptide comprises the amino acid sequence of SEQ ID NO: 9. In some embodiments, the chimeric polypeptide comprises the amino acid sequence of SEQ ID NO: 10. In some embodiments, the chimeric polypeptide comprises the amino acid sequence of SEQ ID NOs: 9 and 10. In some embodiments, the chimeric polypeptide comprises the amino acid sequence of SEQ ID NO: 43. In some embodiments, the chimeric polypeptide comprises the amino acid sequence of SEQ ID NO: 8. In some embodiments, the chimeric polypeptide comprises the amino acid sequences of SEQ ID NOs: 8 and 43.

In some embodiments, the disclosure provides for a nucleic acid construct, comprising a nucleotide sequence that encodes any of the chimeric polypeptides disclosed herein as a chimeric polypeptide comprising a fusion protein. In some embodiments, the nucleotide sequence is codon optimized for expression in a mammalian cell. In some embodiments, the mammalian cell is a CHO cell or a HEK-293 cell.

In some embodiments, the disclosure provides for a set of nucleic acid constructs, together comprising nucleotide sequences that encode any of the chimeric polypeptides disclosed herein. In some embodiments, the nucleotide sequences are codon optimized for expression in a mammalian cell. In some embodiments, the mammalian cell is a CHO cell or a HEK-293 cell.

In some embodiments, the disclosure provides for a vector comprising any of the nucleic acid constructs disclosed herein. In some embodiments, the disclosure provides for a set of vectors comprising any of the sets of nucleic acid constructs disclosed herein.

In some embodiments, the disclosure provides for a host cell comprising any of the vectors or sets of vectors disclosed herein.

In some embodiments, the disclosure provides for a method for delivering alpha-amylase activity into a cell from or of a subject having Lafora Disease, comprising contacting the cell with any of the chimeric polypeptides disclosed herein. In some embodiments, the subject is a non-human animal. In some embodiments, the non-human animal is a mouse. In some embodiments, the subject is a human. In some embodiments, the cell is in the subject. In some embodiments, the cell is a muscle cell. In some embodiments, the cell is a diaphragm muscle cell. In some embodiments, the cell is a brain cell. In some embodiments, the cell is a neuron. In some embodiments, the cell is in vitro.

In some embodiments, the disclosure provides for a method for treating a subject having Lafora disease, comprising administering to the subject a therapeutically effective amount of any of the chimeric polypeptides disclosed herein. In some embodiments, the subject is a non-human animal. In some embodiments, the subject is a mouse. In some embodiments, the subject is a human.

BRIEF DESCRIPTION OF THE FIGURES

The patent or application file contains at least one drawing executed in color. Copies of this patent or patent application publication with color drawings will be provided by the Office upon request and payment of the necessary fee.

FIGS. 3A-3D are images showing Lafora bodies in the brain (FIG. 3A and FIG. 3C), heart (FIG. 3B), and skeletal muscle (FIG. 3D). FIG. 3E is a graph showing the yield (mg per g tissue) of Lafora bodies isolated from the homogenate, pellet and final sample from the brain, heart and skeletal muscle of a Lafora knock out mouse. FIG. 3F is a graph showing the yield (mg per g tissue) of iodine (indicating glycogen) and total glucose from samples of the brain, heart and skeletal muscle.

FIG. 4A is a graph showing the percent of degradation of Lafora bodies from the brain, heart, and skeletal muscle when treated with Fab-amylase, Fab-glucosidase or control. FIG. 4B is a graph showing the Lafora body content Gig per mL extract) of WT and KO mice treated with −Fab-amylase and +Fab-amylse.

FIG. 5A is a graph showing amylase activity in the muscle 1 hr post-injection, 2 hrs post-injection, 4 hrs post-injection, and 24 hrs post-injection. FIG. 5B shows amylase activity (lower panel) for samples of the brain identified (upper panel) immediately post-injection and 1 hour post-injection.

DETAILED DESCRIPTION OF THE DISCLOSURE

Figure 1:
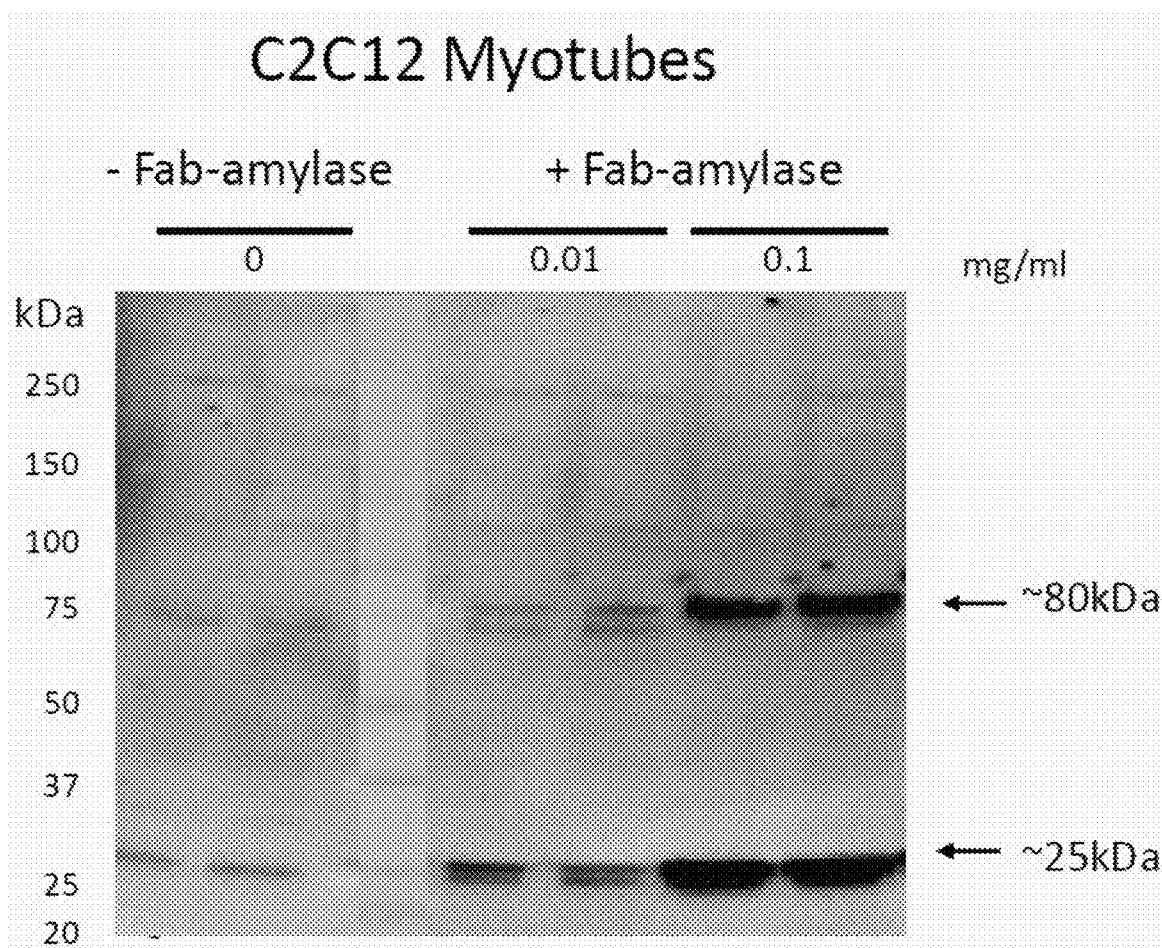
FIG. 1 demonstrates dose dependent uptake of Fab-amylase in ENT2+C2C12 myotubes. A comparison of −Fab-amylase and +Fab-amylase at 0.01 mg/ml and 0.1 mg/ml is provided. (Notes: Anti-H3L2, Rabbit pAb, 1:100; Donkey Anti-Rabbit-HRP, 1:20000).

Glycogen is a complex polysaccharide that provides a ready store of glucose to cells in the human body. Glycogen is found principally in the liver, where it is hydrolyzed and released into the bloodstream to provide glucose to other cells, and in muscle, where the glucose resulting from glycogen hydrolysis provides energy for muscle cells. The proteins laforin, malin and alpha-amylase are believed to play a role in glycogen clearance.

In some embodiments, the disclosure provides for a polypeptide comprising any of the amino acid sequences disclosed herein. In some embodiments, the disclosure provides for a polypeptide comprising an amino acid sequence that is at least 85%, 90%, 91%, 92%, 93%, 94%, 95%, 96%, 97%, 98%, 99% or 100% identical to any of the amino acid sequences disclosed herein.

I. Alpha-Amylase Polypeptides

In certain embodiments, the non-internalizing moiety polypeptide portion of a chimeric polypeptide of the disclosure (or a chimeric polypeptide for use in the methods of the disclosure) is an alpha-amylase polypeptide (e.g., a salivary or pancreatic alpha-amylase). In other words, in certain embodiments, alpha-amylase-containing chimeric polypeptides are provided. Exemplary alpha-amylase (e.g., a mature alpha-amylase) polypeptides for use in the methods and compositions of the disclosure are provided herein. In some embodiments, the alpha-amylase (e.g., a mature alpha-amylase) polypeptides have utility in clearing excess glycogen in diseased cells. In some embodiments, the diseased cells are the cells of a subject having a glycogen storage disease or a glycogen metabolic disorder. In some embodiments, the diseased cells are from a subject having Pompe Disease, Andersen Disease, von Gierke Disease, Lafora Disease and/or Forbes-Cori Disease. In some embodiments, the diseased cells are from a subject having Lafora Disease and/or Forbes-Cori Disease. In particular embodiments, the diseased cells are from a subject having Lafora Disease.

In some embodiments, the alpha-amylase (e.g., a mature alpha-amylase) is a monomer. In some embodiments, the alpha-amylase is a dimer or a trimer. In some embodiments, the alpha-amylase has been mutated such that it is incapable of multimerizing (e.g., the alpha-amylase has been mutated such that it is incapable of dimerizing or trimerizing). In some embodiments, the alpha-amylase has been treated with an agent that inhibits multimerization (e.g., dimerization or trimerization) of the alpha-amylase. In some embodiments, the agent is a small molecule.

As used herein, the alpha-amylase polypeptides include various functional fragments and variants, fusion proteins, and modified forms of the wildtype alpha-amylase polypeptide. In particular embodiments, the alpha-amylase is a mature alpha-amylase. In certain embodiments, the alpha-amylase or fragment or variant thereof is a salivary alpha-amylase or fragment or variant thereof. In certain embodiments, the alpha-amylase or fragment or variant thereof is a pancreatic alpha-amylase or fragment or variant thereof. In certain embodiments, the alpha-amylase or fragment or variant thereof is a mammalian alpha-amylase or fragment or variant thereof. In particular embodiments, the alpha-amylase or fragment or variant thereof is a human alpha-amylase or fragment or variant thereof. Such functional fragments or variants, fusion proteins, and modified forms of the alpha-amylase polypeptides have at least a portion of the amino acid sequence of substantial sequence identity to the native alpha-amylase polypeptide, and retain the function of the native alpha-amylase polypeptide (e.g., ability to hydrolyze alpha-1,4-glucosidic bonds). It should be noted that "retain the function" does not mean that the activity of a particular fragment must be identical or substantially identical to that of the native protein although, in some embodiments, it may be. However, to retain the native activity, that native activity should be at least 50%, at least 60%, at least 70%, at least 75%, at least 80%, at least 85%, at least 90%, at least 95% that of the native protein to which such activity is being compared, with the comparison being made under the same or similar conditions. In some embodiments, retaining the native activity may include scenarios in which a fragment or variant has improved activity versus the native protein to which such activity is being compared, e.g., at least 105%, at least 110%, at least 120%, or at least 125%, with the comparison being bade under the same or similar conditions.

In certain embodiments, a functional fragment, variant, or fusion protein of an alpha-amylase polypeptide comprises an amino acid sequence that is at least 80%, 85%, 90%, 95%, 97%, 98%, 99% or 100% identical to an alpha-amylase polypeptide, such as a mature alpha-amylase polypeptide (e.g., at least 80%, 85%, 90%, 95%, 97%, 98%, 99% or 100% identical to SEQ ID NO: 1), or fragments thereof.

In certain embodiments, the alpha-amylase polypeptide for use in the chimeric polypeptides and methods of the disclosure is a full length or substantially full length alpha-amylase polypeptide, or a mature form of a full-length alpha-amylase. In certain embodiments, the alpha-amylase polypeptide for use in the chimeric polypeptide and methods of the disclosure is a functional fragment that has alpha-1, 4-glucosidic bond hydrolytic activity.

In certain embodiments of any of the foregoing, the alpha-amylase portion of the chimeric polypeptide of the disclosure comprises an alpha-amylase polypeptide (e.g., a mature form), which in certain embodiments may be a functional fragment of an alpha-amylase polypeptide or may be a substantially full length alpha-amylase polypeptide.

In some embodiments, the alpha-amylase is the mature form of an alpha-amylase. In particular embodiments, the mature form of the alpha-amylase corresponds to amino acids 16-511 of SEQ ID NO: 36 (Genbank accession number NP_000690). In some embodiments, the mature form of the alpha-amylase corresponds to an amino acid sequence that is at least 80%, 85%, 90%, 91%, 92%, 93%, 94%, 95%, 96%, 97%, 98%, 99% or 100% identical to the amino acid sequence of SEQ ID NO: 1, or functional fragments thereof.

Suitable alpha-amylase polypeptides or functional fragments thereof for use in the chimeric polypeptides and methods of the disclosure have alpha-1,4-glucosidic bond hydrolytic activity, as evaluated in vitro or in vivo. Exemplary functional fragments comprise, at least 100, 125, 150, 175, 200, 225, 250, 275, 300, 325, 350, 375, 400, 425, 450, 475, 500, or 511 consecutive amino acid residues of a full length alpha-amylase polypeptide (e.g., SEQ ID NO: 36). In some embodiments, the functional fragment comprises 100-150, 100-200, 100-250, 100-300, 100-400, 100-450, 100-495, 200-495, 300-495, 400-495, 450-495, 475-495 consecutive amino acids of a mature alpha-amylase polypeptide (e.g., SEQ ID NO: 1). Similarly, in certain embodiments, the disclosure contemplates chimeric proteins where the alpha-amylase portion is a variant of any of the foregoing alpha-amylase polypeptides or bioactive fragments. Exemplary variants have an amino acid sequence at least 90%, 92%, 95%, 96%, 97%, 98%, or at least 99% identical to the amino acid sequence of a native (e.g. mature) alpha-amylase polypeptide or functional fragment thereof, and such variants retain the alpha-amylase variant's alpha-1,4-glucosidic bond hydrolytic activity. The disclosure contemplates chimeric polypeptides and the use of such polypeptides wherein the alpha-amylase portion comprises any of the alpha-amylase polypeptides, fragments, or variants described herein in combination with any internalizing moiety described herein. Moreover, in certain embodiments, the alpha-amylase portion of any of the foregoing chimeric polypeptides may, in certain embodiments, be a fusion protein. Any such chimeric polypeptides comprising any combination of alpha-amylase portions and internalizing moiety portions, and optionally including one or more linkers, one or more tags, etc., may be used in any of the methods of the disclosure.

In certain embodiments, fragments or variants of the alpha-amylase polypeptides can be obtained by screening polypeptides recombinantly produced from the corresponding fragment of the nucleic acid encoding an alpha-amylase polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native alpha-amylase polypeptide, for example, by testing their ability to treat Lafora Disease in vivo and/or by confirming in vitro (e.g., in a cell free or cell based assay) that the fragment or variant has alpha-1,4-glucosidic bond hydrolytic activity. An example of an in vitro assay for testing for activity of the alpha-amylase polypeptides disclosed herein would be to treat Lafora cells with or without the alpha-amylase-containing chimeric polypeptides and then, after a period of incubation, examining levels of polyglucosan.

In certain embodiments, the present disclosure contemplates modifying the structure of an alpha-amylase polypeptide for such purposes as enhancing therapeutic or prophylactic efficacy, or stability (e.g., ex vivo shelf life and resistance to proteolytic degradation in vivo). Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the alpha-amylase biological activity of the resulting molecule. Conservative replacements are those that take place within a family of amino acids that are related in their side chains.

This disclosure further contemplates generating sets of combinatorial mutants of an alpha-amylase polypeptide, as well as truncation mutants, and is especially useful for identifying functional variant sequences. Combinatorially-derived variants can be generated which have a selective potency relative to a naturally occurring alpha-amylase polypeptide. Likewise, mutagenesis can give rise to variants which have intracellular half-lives dramatically different than the corresponding wild-type alpha-amylase polypeptide. For example, the altered protein can be rendered either more stable or less stable to proteolytic degradation or other cellular process which result in destruction of, or otherwise inactivation of alpha-amylase. Such variants can be utilized to alter the alpha-amylase polypeptide level by modulating their half-life. There are many ways by which the library of potential alpha-amylase variants sequences can be generated, for example, from a degenerate oligonucleotide sequence. Chemical synthesis of a degenerate gene sequence can be carried out in an automatic DNA synthesizer, and the synthetic genes then can be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, alpha-amylase polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the alpha-amylase polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the alpha-amylase polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an alpha-amylase polypeptide may include a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the alpha-amylase polypeptides.

In certain embodiments, an alpha-amylase polypeptide may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified alpha-amylase polypeptides may contain non-amino acid elements, such as lipids, poly- or mono-saccharides, and phosphates. Effects of such non-amino acid elements on the functionality of an alpha-amylase polypeptide may be tested for its biological activity, for example, alpha-1,4-glucosidic bonds hydrolytic activity and/or its ability to treat Lafora Disease. In certain embodiments, the alpha-amylase polypeptide may further comprise one or more polypeptide portions that enhance one or more of in vivo stability, in vivo half life, uptake/administration, and/or purification. In other embodiments, the internalizing moiety comprises an antibody or an antigen-binding fragment thereof.

In some embodiments, an alpha-amylase polypeptide is not N-glycosylated or lacks one or more of the N-glycosylation groups present in a wildtype alpha-amylase polypeptide. For example, the alpha-amylase polypeptide for use in the present disclosure may lack all N-glycosylation sites, relative to native alpha-amylase, or the alpha-amylase polypeptide for use in the present disclosure may be under-glycosylated, relative to native alpha-amylase. In some embodiments, the alpha-amylase polypeptide comprises a modified amino acid sequence that is unable to be N-glycosylated at one or more N-glycosylation sites. In some embodiments, asparagine (Asn) of at least one predicted N-glycosylation site (i.e., a consensus sequence represented by the amino acid sequence Asn-Xaa-Ser or Asn-Xaa-Thr) in the alpha-amylase polypeptide is substituted by another amino acid. In some embodiments, the asparagine at the amino acid position corresponding to residue 412 and/or 461 of SEQ ID NO: 1 is substitute by another amino acid. The disclosure contemplates that any one or more of the foregoing examples can be combined so that an alpha-amylase polypeptide of the present disclosure lacks one or more N-glycosylation sites, and thus is either not glycosylated or is under glycosylated relative to native alpha-amylase.

In some embodiments, an alpha-amylase polypeptide is not 0-glycosylated or lacks one or more of the O-glycosylation groups present in a wildtype alpha-amylase polypeptide. In some embodiments, the alpha-amylase polypeptide comprises a modified amino acid sequence that is unable to be 0-glycosylated at one or more O-glycosylation sites. In some embodiments, serine or threonine at any one or more predicted 0-glycosylation site in the alpha-amylase polypeptide sequence is substituted or deleted. The disclosure contemplates that any one or more of the foregoing examples can be combined so that an alpha-amylase polypeptide of the present disclosure lacks one or more N-glycosylation and/or O-glycosylation sites, and thus is either not glycosylated or is under glycosylated relative to native alpha-amylase.

In one specific embodiment of the present disclosure, an alpha-amylase polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the alpha-amylase polypeptide to carry out the functions associated with wildtype mature alpha-amylase polypeptides, for example, alpha-1,4-glucosidic bond hydrolytic activity or ability to hydrolyze polyglucosan. The terms "biological activity", "bioactivity", and "functional" are used interchangeably herein. As used herein, "fragments" are understood to include bioactive fragments (also referred to as functional fragments) or bioactive variants that exhibit "bioactivity" as described herein. That is, bioactive fragments or variants of alpha-amylase exhibit bioactivity that can be measured and tested. For example, bioactive fragments/functional fragments or variants exhibit the same or substantially the same bioactivity as native (i.e., wild-type, or normal) alpha-amylase polypeptide, and such bioactivity can be assessed by the ability of the fragment or variant to, e.g., hydrolyze alpha-1,4-glucosidic bonds in a carbohydrate. As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the mature alpha-amylase polypeptide will preferably retain at least 50%, 60%, 70%, 80%, 85%, 90%, 95% or 100% of the alpha-amylase biological activity associated with the native mature alpha-amylase polypeptide, when assessed under the same or substantially the same conditions.

In certain embodiments, fragments or variants of the alpha-amylase polypeptide have a half-life ($t_{1/2}$) which is enhanced relative to the half-life of the native protein. Preferably, the half-life of alpha-amylase fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native alpha-amylase polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native alpha-amylase polypeptide.

With respect to methods of increasing alpha-amylase bioactivity in cells, the disclosure contemplates all combinations of any of the foregoing aspects and embodiments, as well as combinations with any of the embodiments set forth in the detailed description and examples. The described methods based on administering chimeric polypeptides or contacting cells with chimeric polypeptides can be performed in vitro (e.g., in cells or culture) or in vivo (e.g., in a patient or animal model). In certain embodiments, the method is an in vitro method. In certain embodiments, the method is an in vivo method.

In some aspects, the present disclosure also provides a method of producing any of the foregoing chimeric polypeptides as described herein. Further, the present disclosure contemplates any number of combinations of the foregoing methods and compositions.

In certain aspects, an alpha-amylase polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), His and c-myc tags. An exemplary His tag has the sequence HHHHHH (SEQ ID NO: 15), and an exemplary c-myc tag has the sequence EQKLISEEDL (SEQ ID NO: 16). In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the alpha-amylase polypeptides may contain one or more modifications that are capable of stabilizing the polypeptides. For example, such modifications enhance the in vitro half life of the polypeptides, enhance circulatory half life of the polypeptides or reduce proteolytic degradation of the polypeptides.

II. Internalizing Moieties

As used herein, the term "internalizing moiety" refers to a polypeptide/protein capable of interacting with a target tissue or a cell type such that the moiety is internalized into the target tissue or the cell type.

As used herein, "antibodies or antigen binding fragments of the disclosure" refer to any one or more of the antibodies and antigen binding fragments provided herein. Antibodies and antigen binding fragments of the disclosure comprise a heavy chain comprising a heavy chain variable domain and a light chain comprising a light chain variable domain. A $V_H$ domain comprises three CDRs, such as any of the CDRs provided herein and as defined or identified by the Kabat and/or IMGT systems. These CDRs are typically interspersed with framework regions (FR), and together comprise the $V_H$ domain.

Similarly, a VL comprises three CDRs, such as any of the CDRs provided herein and as defined by the Kabat and/or IMGT systems. These CDRs are typically interspersed with framework regions (FR), and together comprise the $V_L$ domain. The FR regions, such as FR1, FR2, FR3, and/or FR4 can similarly be defined or identified by the Kabat or IMGT systems. Throughout the application, when CDRs are indicated as being, as identified or defined by the Kabat or IMGT systems, what is meant is that the CDRs are in accordance with that system (e.g., the Kabat CDRs or the IMGT CDRs). Any of these terms can be used to indicate whether the Kabat or IMGT CDRs are being referred to.

The disclosure contemplates that an antibody or antigen binding fragment may comprise any combination of a $V_H$ domain, as provided herein, and a $V_L$ domain, as provided herein. In certain embodiments, at least one of the $V_H$ and/or $V_L$ domains are humanized (collectively, antibodies or antigen binding fragments of the disclosure). Chimeric antibodies are also included. Any antibody or antigen binding fragment of the disclosure may be provided alone. In other embodiments, any antibody or antigen binding fragment of the disclosure may be provided as a conjugate associated with a heterologous agent. Non-limiting examples of heterologous agents, which may include polypeptides, peptides, small molecules (e.g., a chemotherapeutic agent small molecule), or polynucleotides, are provided herein. Conjugates may refer to an antibody or antigen binding fragment associated with a heterologous agent.

In some embodiments, the antibody or antigen-binding fragment is isolated and/or purified. Any of the antibodies or antigen-binding fragments described herein, including those provided in an isolated or purified form, may be provided as a composition, such as a composition comprising an antibody or antigen-binding fragment formulated with one or more pharmaceutical and/or physiological acceptable carriers and/or excipients. Any of the antibodies or antigen-binding fragments described herein, including compositions (e.g., pharmaceutical compositions) may be used in any of the methods described herein and may be optionally provided conjugated (e.g., interconnected; associated) with a heterologous agent. In some embodiments, the internalizing moiety is capable of interacting with a target tissue or a cell type to effect delivery of the heterologous agent into a cell (i.e., penetrate desired cell; transport across a cellular membrane; deliver across cellular membranes to, at least, the cytoplasm). Such conjugates may similarly be provided as a composition and may be used in any of the methods described herein.

Internalizing moieties having limited cross-reactivity are generally preferred. In certain embodiments, this disclosure relates to an internalizing moiety which selectively, although not necessarily exclusively, targets and penetrates muscle, liver and/or neuronal cells. In certain embodiments, the internalizing moiety has limited cross-reactivity, and thus preferentially targets a particular cell or tissue type. However, it should be understood that internalizing moieties of the subject disclosure do not exclusively target specific cell types. Rather, the internalizing moieties promote delivery to one or more particular cell types, preferentially over other cell types, and thus provide for delivery that is not ubiquitous. In certain embodiments, suitable internalizing moieties include, for example, antibodies, monoclonal antibodies, or derivatives or analogs thereof. In certain embodiments, the internalizing moiety mediates transit across cellular membranes via an ENT2 transporter. In some embodiments, the internalizing moiety helps the chimeric polypeptide effectively and efficiently transit cellular membranes. In some embodiments, the internalizing moiety transits cellular membranes via an equilibrative nucleoside (ENT) transporter. In some embodiments, the internalizing moiety transits cellular membranes via an ENT1, ENT2, ENT3 or ENT4 transporter. In some embodiments, the internalizing moiety transits cellular membranes via an equilibrative nucleoside transporter 2 (ENT2) and/or ENT3 transporter. In some embodiments, the internalizing moiety promotes delivery into muscle (e.g., cardiac or diaphragm muscle), liver, skin or neuronal (e.g., brain) cells. For any of the foregoing, in certain embodiments, the internalizing moiety is internalized into the cytoplasm. In certain embodiments, the internalizing moiety is internalized into the nucleus or lysosomes.

In certain embodiments, the internalizing moiety is an antibody or antibody fragment that binds DNA. In certain embodiments, the internalizing moiety is any of the antibody or antibody fragments described herein. In other words, in certain embodiments, the antibody or antibody fragment (e.g., antibody fragment comprising an antigen binding fragment) binds DNA. In certain embodiments, DNA binding ability is measured versus a double stranded DNA substrate. In certain embodiments, the internalizing moiety is an antibody or antibody fragment that binds DNA and can transit cellular membranes via ENT2. In certain embodiments, the internalizing moiety binds a DNA bubble.

In certain embodiments, the internalizing moiety is capable of binding polynucleotides. In certain embodiments, the internalizing moiety is capable of binding DNA. In certain embodiments, the internalizing moiety is an antibody capable of binding DNA. In certain embodiments, the internalizing moiety is capable of binding DNA with a $K_D$ of less than 1 µM. In certain embodiments, the internalizing moiety is capable of binding DNA with a $K_D$ of less than 100 nM, less than 75 nM, less than 50 nM, or even less than 30 nM. $K_D$ can be measured using Surface Plasmon Resonance (SPR) or Quartz Crystal Microbalance (QCM), in accordance with currently standard methods. By way of example, a 3E10 antibody or antibody fragment, including an antibody or antibody fragment comprising a VH having the amino acid sequence set forth in SEQ ID NO: 17 and a VL having an amino acid sequence set forth in SEQ ID NO: 18 is known to bind DNA with a $K_D$ of less than 100 nM. Thus, in certain embodiments, an internalizing moiety for use in the chimeric polypeptides of the disclosure is an antibody or antibody fragment (e.g., an antigen binding fragment) that can transit cellular membranes into the cytoplasm and binds to DNA. This is also exemplary of an anti-DNA antibody. In certain embodiments, an internalizing moiety for use herein is an anti-DNA antibody or antigen binding fragment thereof. In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In fact, a full length antibody comprising the foregoing VH and VL binds a double-stranded blunt DNA substrate with an even lower $K_D$, as evaluated by ELISA. In certain embodiments, the internalizing moiety binds double-stranded, blunt DNA, and DNA binding activity is or can be demonstrated in a binding assay using blunt DNA (see, for example, Xu et. Al. (2009) EMBO Journal 28: 568-577; Hansen et al., (2012) Sci Translation Med 4: DOI 10.1126/scitranslmed.3004385), such as by ELISA, QCM, or Biacore. In certain embodiments, the foregoing $K_D$ of the antibody or antibody fragment (such as an antibody fragment comprising an antigen-binding fragment) is evaluated versus a double stranded, blunt end DNA substrate, such as the DNA substrate set forth in Xu et al. In certain embodiments, the internalizing moiety is an anti-DNA antibody. It is recognized that 3E10 and other anti-DNA antibodies may be capable of binding a variety of DNA substrates with high affinity, as has been demonstrated.

In some embodiments, any of the internalizing moieties described herein, such as any of the antibodies or antigen-binding fragments of the disclosure, is capable of binding specific nucleotide motifs present in a polynucleotide sequence. In some embodiments, the internalizing moiety is capable of binding AT-rich sequences. In some embodiments, the internalizing moiety binds to AT-rich sequences with a stronger affinity than to a GC-rich sequence. In some embodiments, the internalizing moiety is capable of binding a TATA sequence. In some embodiments, the internalizing moiety binds to 4-mer TATA motifs within a 6 base pair sequence. In some embodiments, the internalizing moiety is capable of binding a DNA bubble. In some embodiments, the internalizing moiety is capable of binding a DNA sequence adjacent to a DNA bubble. In some embodiments, the internalizing moiety is capable of binding a DNA sequence adjacent to a DNA bubble that is at least 3, 4, 5, 6, 7, 8, 9, 10, 11, 12, 13, 14, 15, 16, 17, 18, 19, 20, 21, 22, 23, 24, or at least 25 base pairs in length. In some embodiments, the internalizing moiety is capable of binding a 5-mer variable region adjacent to a 7-base or 11-base bubble. In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In some embodiments, any of the internalizing moieties described herein bind DNA at DNA response elements. In some embodiments, the internalizing moieties bind DNA response elements to prevent transcription factors or proteins from binding to the elements. In some embodiments, the internalizing moieties block or inhibit transcription.

In certain aspects, any of the internalizing moieties described herein bind DNA at DNA repair sites. In some embodiments, the internalizing moiety binds a DNA bubble formed at a DNA repair site. In some embodiments, the internalizing moiety binds DNA at a DNA repair site, wherein the DNA repair site is present as the result of DNA damage due to chemotherapeutic or radiotherapeutic treatment. In some embodiments, the internalizing moiety binds DNA at a DNA repair site wherein the DNA repair site is present as the result of DNA damage due to chemotherapeutic treatment. In some embodiments, the chemotherapeutic treatment is treatment with a DNA cross-linker (e.g., a platin such as cisplatin, carboplatin, oxaliplatin or an active analog thereof), an inhibitor of DNA synthesis (e.g., methotrexate or an active analog thereof), a topoisomerase poison (e.g., doxorubicin, daunorubicin, or an active analog thereof), a DNA alkylating agent (e.g., a nitrosurea, triazene compound or an active analog thereof), and/or an antimetabolite (e.g., a pyrimidine analog such as 5-fluorouracil or an active analog thereof).

In some embodiments, any of the internalizing moieties of the disclosure are capable of binding DNA at DNA sites independent of DNA repair sites.

In certain aspects, an internalizing moiety may comprise an antibody, including a monoclonal antibody, a polyclonal antibody, and a humanized antibody. In some embodiments, the internalizing moiety is a full-length antibody. In some embodiments, internalizing moieties may comprise antibody fragments, derivatives or analogs thereof, including without limitation: antibody fragments comprising antigen binding fragments (e.g., Fv fragments, single chain Fv (scFv) fragments, Fab fragments, Fab' fragments, F(ab')2 fragments), single domain antibodies, camelized antibodies and antibody fragments, humanized antibodies and antibody fragments, human antibodies and antibody fragments, and multivalent versions of the foregoing; multivalent internalizing moieties including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In some embodiments, the antibodies or variants thereof may be chimeric, e.g., they may include variable heavy or light regions from the murine 3E10 antibody, but may include constant regions from an antibody of another species (e.g., a human). In some embodiments, the antibodies or variants thereof may comprise a constant region that is a hybrid of several different antibody subclass constant domains (e.g., any combination of IgG1, IgG2a, IgG2b, IgG3 and IgG4, from any species or combination of species). In some embodiments, the antibodies or variants thereof (e.g., the internalizing moiety) comprise the following constant domain scheme: IgG2a CH1-IgG1 hinge-IgG1 CH2-CH3, for example, any of the foregoing may be human IgG or murine IgG. Other suitable combinations are also contemplated. In other embodiments, the antibody comprises a full length antibody and the CH1, hinge, CH2, and CH3 is from the same constant domain subclass (e.g., IgG1). In some embodiments, the antibodies or variants thereof are antibody fragments (e.g., the internalizing moiety is an antibody fragment comprising an antigen binding fragment; e.g., the internalizing moiety is an antigen binding fragment) comprising a portion of the constant domain of an immunoglobulin, for example, the following constant domain scheme: IgG2a CH1-IgG1 upper hinge. In some embodiments, the antibodies or variants thereof are antibody fragments that comprise a sequence that is at least 85%, 90%, 91%, 92%, 93%, 94%, 95%, 96%, 97%, 98%, 99% or 100% identical to the amino acid sequence of SEQ ID NO: 11.

In some embodiments, the antibodies or variants thereof comprise a kappa constant domain (e.g., of the Km3 allotype). In some embodiments, the antibodies or variants thereof are antibody fragments that comprise a sequence that is at least 85%, 90%, 91%, 92%, 93%, 94%, 95%, 96%, 97%, 98%, 99% or 100% SEQ ID NO: 12. Heavy chain constant domains (whether for a full length antibody or for an antibody fragment (e.g., an antigen binding fragment) comprising an amino acid substitution, relative to native IgG domains, to decrease effector function and/or facilitate production are included within the scope of antibodies and antigen binding fragments. For example, one, two, three, or four amino acid substitutions in a heavy chain, relative to a native murine or human immunoglobulin constant region, such as in the hinge or CH2 domain of a heavy chain constant region.

In certain embodiments, an internalizing moiety comprises an antibody, and the heavy chain comprises a VH region, and a constant domain comprising a CH1, hinge, CH2, and CH3 domain. In certain embodiments, a heavy chain comprises a VH region, and a constant domain comprising a CH1 domain and, optionally, the upper hinge. The upper hinge may include, for example, 1, 2, 3, or 4 amino acid residues of the hinge region. In certain embodiments, the upper hinge does not include a cysteine residue. In certain embodiments, the upper hinge includes one or more consecutive residues N-terminal to a cysteine that exists in the native hinge sequence. In certain embodiments, the heavy chain comprises a CH region, and a constant domain comprising a CH1 domain and a hinge. In certain embodiments, the hinge (whether present as part of a full length antibody or an antibody fragment) comprises a C to S substitution at a position corresponding to Kabat position 222 (e.g., a C222S in the hinge, where the variation is at a position corresponding to Kabat position 222). In other words, in certain embodiments, the internalizing moiety comprises a serine residue, rather than a cysteine residue, in a hinge domain at a position corresponding to Kabat 222. In certain embodiments, the heavy chain comprises a constant domain comprising a CH1, hinge, CH2 and, optionally CH3 domain. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In some embodiments, the internalizing moiety comprises all or a portion of the Fc region of an immunoglobulin. In other words, in addition to an antigen binding portion, in certain embodiments, the internalizing moiety comprises all or a portion of a heavy chain constant region of an immunoglobulin (e.g., one or two polypeptide chains of a heavy chain constant region. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region, or a portion of a hinger (e.g., an upper hinge). In certain embodiments, an internalizing moiety further comprises a light chain constant region (CL).

In some embodiments, the Fc portion of any of the internalizing moieties described herein has been modified such that it does not induce antibody-dependent cell-mediated cytotoxicity (ADCC). In some embodiments, the Fc portion has been modified such that it does not bind complement. In certain embodiments, a CH2 domain of the Fc portion comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fcγ or the homologous domains in any of IgA, IgD, IgE, or IgM. Furthermore, it is contemplated that substitution or deletion of amino acids within the immunoglobulin heavy chain constant regions may be useful in the practice of the disclosure. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In some embodiments, any of the internalizing moieties disclosed herein comprise a signal sequence conjugated to the heavy chain and/or the light chain amino acid sequence. In some embodiments, the heavy chain comprises a signal sequence that is at least 85%, 90%, 91%, 92%, 93%, 94%, 95%, 96%, 97%, 98%, 99% or 100% identical to the amino acid sequence of SEQ ID NO: 4. In some embodiments, the light chain comprises a signal sequence that is at least 85%, 90%, 91%, 92%, 93%, 94%, 95%, 96%, 97%, 98%, 99% or 100% identical to the amino acid sequence of SEQ ID NO: 5. In some embodiments, the signal sequence lacks the N-terminal Methionine. In some embodiments, any of the polypeptides disclosed herein lacks the N-terminal Methionine.

In some embodiments, the internalizing moiety is any peptide or antibody-like protein having the complementarity determining regions (CDRs) of the 3E10 antibody sequence, or of an antibody that binds the same epitope (e.g., the same target, such as DNA) as 3E10. Also, transgenic mice, or other mammals, may be used to express humanized or human antibodies. Such humanization may be partial or complete.

In certain embodiments, the internalizing moiety comprises the monoclonal antibody 3E10 or an antigen binding fragment thereof. In other embodiments, the internalizing moiety comprises an antibody or an antigen binding fragment thereof, such as any of the antigen binding fragments described herein. For example, the antibody or antigen binding fragment thereof may be monoclonal antibody 3E10, or a variant thereof that retains cell penetrating activity, or an antigen binding fragment of 3E10 or said 3E10 variant. Additionally, the antibody or antigen binding fragment thereof may be an antibody that binds to the same epitope (e.g., target, such as DNA) as 3E10, or an antibody that has substantially the same cell penetrating activity as 3E10, or an antigen binding fragment thereof. These are exemplary of agents that can transit cells via ENT2. In certain embodiments, the internalizing moiety is capable of binding polynucleotides. In certain embodiments, the internalizing moiety is capable of binding DNA, such as double-stranded blunt DNA. In certain embodiments, the internalizing moiety is capable of binding DNA with a $K_D$ of less than 100 nM. In certain embodiments, the internalizing moiety is capable of binding DNA with a $K_D$ of less than 100 nM, less than 75 nM, less than 50 nM, or even less than 30 nM. $K_D$ is determined using SPR or QCM or ELISA, according to manufacturer's instructions and current practice. In some embodiments, $K_D$ is determined using a fluorescence polarization assay.

In certain embodiments, the antigen binding fragment is an Fv or scFv fragment thereof. Monoclonal antibody 3E10 can be produced by a hybridoma 3E10 placed permanently on deposit with the American Type Culture Collection (ATCC) under ATCC accession number PTA-2439 and is disclosed in U.S. Pat. No. 7,189,396. This antibody has been shown to bind DNA. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used to refer to the antibody, regardless of the method used to produce the antibody. Similarly, when referring to variants or antigen-binding fragments of 3E10, such terms are used without reference to the manner in which the antibody was produced. At this point, 3E10 is generally not produced by the hybridoma but is produced recombinantly. Thus, in the context of the present application, 3E10 antibody, unless otherwise specified, will refer to an antibody having the sequence of the hybridoma or comprising a variable heavy chain domain comprising the amino acid sequence set forth in SEQ ID NO: 17 (which has a one amino acid substitution relative to that of the 3E10 antibody deposited with the ATCC, as described herein) and the variable light chain domain comprising the amino acid sequence set forth in SEQ ID NO: 18, and antibody fragments thereof.

The internalizing moiety may also comprise variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative or non-conservative substitutions are introduced into the heavy chain, the light chain and/or the constant region(s) of the antibody. Such variants include humanized versions of 3E10 or a 3E10 variant, particularly those with improved activity or utility, as provided herein. In some embodiments, the light chain or heavy chain may be modified at the N-terminus or C-terminus. Similarly, the foregoing description of variants applies to antigen binding fragments. Any of these antibodies, variants, or fragments may be made recombinantly by expression of the nucleotide sequence(s) in a host cell.

The internalizing moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety.

In certain embodiments, the internalizing moiety comprises an antibody or antigen binding fragment comprising an VH domain comprising an amino acid sequence at least 80%, 85%, 90%, 95%, 96%, 97%, 99%, or 100% identical to SEQ ID NO: 17 and/or a VL domain comprising an amino acid sequence at least 85%, 90%, 95%, 96%, 97%, 99%, or 100% identical to SEQ ID NO: 18, or a humanized variant thereof. It is understood that, when a signal sequence is included for expression of an antibody or antibody fragment, that signal sequence is generally cleaved and not presented in the finished chimeric polypeptide (e.g., the signal sequence is generally cleaved and present only transiently during protein production). Such internalizing moieties transit, in certain embodiments, cells via ENT2 and/or bind DNA. In certain embodiments, an internalizing moiety for use in the methods of the present disclosure (or an antibody or antigen binding fragment for such use) is not an antibody or antibody fragment having the VH and VL of the antibody produced by the hybridoma deposited with the ATCC under ATCC accession number PTA-2439. In some embodiments, an internalizing moiety for use in the methods of the present disclosure (or an antibody or antigen binding fragment for such use) is not an antibody or antibody fragment having a VH comprising the amino acid sequence set forth in SEQ ID NO: 17 and a VL comprising the amino acid sequence set forth in SEQ ID NO: 18.

In certain embodiments, the internalizing moiety is capable of binding polynucleotides. In certain embodiments, the internalizing moiety is capable of binding (specifically binding) DNA. In certain embodiments, the internalizing moiety is capable of binding DNA with a $K_D$ of less than 100 nM. In certain embodiments, the internalizing moiety is capable of binding DNA with a $K_D$ of less than 50 nM. In certain embodiments, the internalizing moiety is an anti-DNA antibody, such as an antibody or antigen binding fragment that binds double-stranded blunt DNA. In certain embodiments, the internalizing moiety is an anti-DNA antibody or antigen binding fragment (thereof), where $K_D$ is evaluated versus a double stranded DNA substrate, such as provided herein.

In certain embodiments, the internalizing moiety is an antigen binding fragment, such as a single chain Fv of 3E10 (scFv) comprising SEQ ID NOs: 17 and 18. In certain embodiments, the internalizing moiety comprises a single chain Fv of 3E10 (or another antigen binding fragment), and the amino acid sequence of the $V_H$ domain is at least 90%, 95%, 96%, 97%, 98%, 99%, or 100% identical to SEQ ID NO: 17, and amino acid sequence of the $V_L$ domain is at least 90%, 95%, 96%, 97%, 98%, 99%, or 100% identical to SEQ ID NO: 18. The variant 3E10 or fragment thereof retains the function of an internalizing moiety. When the internalizing moiety is an scFv, the VH and VL domains are typically connected via a linker, such as a gly/ser linker. The VH domain may be N-terminal to the VL domain or vice versa.

In certain embodiments, the internalizing moiety is an antigen binding fragment, such as a Fab comprising a VH and a VL. In certain embodiments, the internalizing moiety is a Fab (or another antigen binding fragment, such as a Fab'), and the amino acid sequence of the $V_H$ domain is at least 90%, 95%, 96%, 97%, 98%, 99%, or 100% identical to SEQ ID NO: 17. In certain embodiments, the internalizing moiety is a Fab (or another antigen binding fragment, such as a Fab'), and the amino acid sequence of the $V_L$ domain is at least 90%, 95%, 96%, 97%, 98%, 99%, or 100% identical to SEQ ID NO: 18. Our VH and VL domains, or combinations thereof, described herein are similarly contemplated. In certain embodiments, when the internalizing moiety is a Fab the heavy chain comprises a CH1 domain and an upper hinge of an immunoglobulin constant region. In certain embodiments, the upper hinge comprises a substitution, relative to a native immunoglobulin constant region, such as to decrease effector function and/or to eliminate a cysteine (e.g., a C to S). In certain embodiments, the upper hinge does not include a cysteine.

In certain embodiments, an internalizing moiety for use in the methods of the present disclosure (or an antibody or antigen binding fragment for such use) is not an antibody or antibody fragment having the VH and VL of the antibody produced by the hybridoma deposited with the ATCC under ATCC accession number PTA-2439. In some embodiments, an internalizing moiety for use in the methods of the present disclosure (or an antibody or antigen binding fragment for such use) is not an antibody or antibody fragment having a VH comprising the amino acid sequence set forth in SEQ ID NO: 17 and a VL comprising the amino acid sequence set forth in SEQ ID NO: 18.

In certain embodiments, the constant domain of the antibody or antibody fragment (e.g., antigen binding fragment) comprises all or a portion of a human Fc domain. In certain embodiments, the internalizing moiety is a full length antibody, and the constant domain of the antibody comprises a CH1, hinge, CH2 and CH3 domain. In certain embodiments, the constant domain comprises one or more substitutions, relative to a native immunoglobulin, that reduce effector function. Optionally, in certain embodiments, such a constant domain may include one or more (e.g., 1 substitution, 2 substitutions, 3 substitutions) substitutions in the heavy chain constant domain, such as in the hinge and/or CH2 domains, such as to reduce effector function. Such substitutions are known in the art.

In certain embodiments, the internalizing moiety is an antigen binding fragment—a fragment of an antibody comprising an antigen binding fragment. Suitable such fragments of antibodies, such as scFv, Fab, Fab' and the like are described herein. In certain embodiments, the internalizing moiety is an antigen binding fragment or a full length antibody. In certain embodiments, the internalizing moiety comprises a light chain comprising a constant region (CL). In certain embodiments, the internalizing moiety comprises a heavy chain comprising a constant region, wherein the constant region comprises a CH1 domain. In certain embodiments, the internalizing moiety comprises a heavy chain comprising a constant region and a light chain comprising a constant region, wherein the heavy chain constant region comprises a CH1 domain. Optionally, the internalizing moiety may further comprise a heavy chain constant region comprising all or a portion of a hinge (e.g., an upper hinge or more than the upper hinge). Optionally, the internalizing moiety may further comprise a heavy chain comprising a CH2 and/or CH3 domain.

In some embodiments, the internalizing moiety comprises one or more of the CDRs of the 3E10 antibody. In certain embodiments, the internalizing moiety comprises one or more of the CDRs of a 3E10 antibody comprising the amino acid sequence of a $V_H$ domain that is identical to SEQ ID NO: 17 and the amino acid sequence of a $V_L$ domain that is identical to SEQ ID NO: 18. The CDRs of the 3E10 antibody may be determined using any of the CDR identification schemes available in the art. For example, in some embodiments, the CDRs of the 3E10 antibody are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs of the 3E10 antibody are defined according to Chothia et al., 1987, J Mol Biol. 196: 901-917 and Chothia et al., 1989, Nature. 342:877-883. In other embodiments, the CDRs of the 3E10 antibody are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs of the 3E10 antibody are defined according to any of the CDR identification schemes discussed in Kunik et al., 2012, PLoS Comput Biol. 8(2): e1002388. In order to number residues of a 3E10 antibody for the purpose of identifying CDRs according to any of the CDR identification schemes known in the art, one may align the 3E10 antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence.

In certain embodiments, the internalizing moiety comprises at least 1, 2, 3, 4, or 5 of the CDRs of 3E10 as determined using the Kabat CDR identification scheme (e.g., the CDRs set forth in SEQ ID NOs: 19-24; the internalizing moiety is an antibody or antigen binding fragment thereof comprising a heavy chain comprising CDR1, CDR2, and CDR 3, as set forth in SEQ ID NOs: 19-21, respectively, and a light chain comprising CDR1, CDR2, and CDR3, as set forth in SEQ ID NOs: 22-24, respectively; e.g., and these CDRs in the internalizing moiety are as determined using the Kabat scheme). In other embodiments, the internalizing moiety comprises at least 1, 2, 3, 4 or 5 of the CDRs of 3E10 as determined using the IMGT identification scheme (e.g., the CDRs set forth in SEQ ID NOs: 27-32; the internalizing moiety is an antibody or antigen binding fragment thereof comprising a heavy chain comprising CDR1, CDR2, and CDR 3, as set forth in SEQ ID NOs: 27-29, respectively, and a light chain comprising CDR1, CDR2, and CDR3, as set forth in SEQ ID NOs: 30-32, respectively; e.g., and these CDRs in the internalizing moiety are as determined using the IMGT identification scheme). In certain embodiments, the internalizing moiety comprises all six CDRs of 3E10 as determined using the Kabat CDR identification scheme (e.g., comprises SEQ ID NOs 19-24). In other embodiments, the internalizing moiety comprises all six CDRS of 3E10 as determined using the IMGT identification scheme (e.g., which are set forth as SEQ ID NOs: 27-32). For any of the foregoing, in certain embodiments, the internalizing moiety is an antibody that binds the same epitope (e.g., the same target, such as DNA) as 3E10 and/or the internalizing moiety competes with 3E10 for binding to antigen. Exemplary internalizing moieties target and transit cells via ENT2. Exemplary internalizing moieties comprise antibodies or antigen binding fragments that bind DNA, such as double stranded blunt DNA.

In certain embodiments, the internalizing moiety comprising an antibody fragment, and the antibody fragment comprises an antigen binding fragment, such as an Fab or Fab'. In other words, in certain embodiments, the internalizing moiety comprises an Fab or Fab'.

In certain embodiments, the internalizing moiety competes with binding for a DNA substrate, such as double-stranded blunt DNA, with an antibody (or antigen-binding fragment) of the antibody produced by hybridoma 3E10 placed permanently on deposit with the American Type Culture Collection (ATCC) under ATCC accession number PTA-2439.

Preparation of antibodies or fragments thereof (e.g., a single chain Fv fragment encoded by $V_H$-linker-$V_L$ or $V_L$-linker-$V_H$ or a Fab) is well known in the art. In particular, methods of recombinant production of mAb 3E10 antibody fragments have been described in WO 2008/091911. Further, methods of generating scFv fragments of antibodies or Fabs are well known in the art. When recombinantly producing an antibody or antibody fragment, a linker may be used. For example, typical surface amino acids in flexible protein regions include Gly, Asn and Ser. One exemplary linker is provided in SEQ ID NO: 6, 13 or 14. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)n$, wherein n is an integer from 1-10, such as 2, 3, or 4. Other near neutral amino acids, such as Thr and Ala, can also be used in the linker sequence.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen (s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

The disclosure contemplates the use of internalizing moieties (including antibodies or antigen binding fragments of the disclosure) described based on any combination of any of the foregoing or following structural and/or functional characteristics. Any such internalizing moieties, such as antibodies or antigen-binding fragments, are considered antibodies and antigen binding fragments of the disclosure and can be used for any of the uses or methods described herein, such as to treat Lafora Disease.

Further Examples of Antibodies or Antigen-Binding Fragments, Such as Humanized Antibodies or Antigen Binding Fragments In some embodiments, the disclosure provides any of the antibodies or antigen-binding fragments disclosed herein, wherein the antibody or antigen-binding fragment is humanized. In other words, one class of internalizing moiety, such as antibody or antigen binding fragment, is a humanized antibody or antigen binding fragment. Such internalizing moiety may be humanized in whole or in part. Numerous examples of such humanized internalizing moieties are provided herein and are also described in WO 2015/106290, which is incorporated herein in its entirety.

In one embodiment, the disclosure provides an antibody or antigen-binding fragment comprising a humanized antibody or antigen-binding fragment, wherein the humanized antibody or antigen-binding fragment comprises a light chain variable (VL) domain and a heavy chain variable (VH) domain; wherein the $V_H$ domain is humanized and comprises:

a VH CDR1 having the amino acid sequence of SEQ ID NO: 27;

a VH CDR2 having the amino acid sequence of SEQ ID NO: 28; and a VH CDR3 having the amino acid sequence of SEQ ID NO: 29;

and the VL is humanized and comprises:

a VL CDR1 having the amino acid sequence of SEQ ID NO: 30;

a VL CDR2 having the amino acid sequence of SEQ ID NO: 31; and a VL CDR3 having the amino acid sequence of SEQ ID NO: 32;

which CDRs are in accordance with the IMGT system, and wherein the humanized antibody or antigen-binding fragment has increased DNA binding and/or cell penetration, relative to that of a murine 3E10 antibody comprising a light chain variable (VL) domain having the amino acid sequence of SEQ ID NO: 18 and a heavy chain variable (VH) domain having the amino acid sequence of SEQ ID NO: 17. In certain embodiments, when comparing an antibody or antigen-binding fragment of the disclosure to a murine antibody or to another humanized antibody, the suitable comparison is between two proteins of the same structure (e.g., comparing a full length antibody to another full length antibody or comparing an Fab to another Fab). However, in other embodiments, the comparison is to an scFv or Fv of the murine antibody as a constant basis for comparison.

In some embodiments, an asparagine is mutated to another amino acid residue in the VH or VL domains in order to reduce N-linked glycosylation of the humanized antibody or antibody fragment. This humanized antibody or antibody fragment is based on a murine parent antibody—specifically a murine 3E10 antibody comprising a heavy chain and a light chain, wherein the light chain comprises a VL comprising the amino acid sequence of SEQ ID NO: 18 and the heavy chain comprises a VH comprising the amino acid sequence of SEQ ID NO: 17. In preferred embodiments, the internalizing moieties and fragments are associated with at least the cell-penetration properties associated with the murine 3E10 antibody (e.g., retain at least 75%, 80%, 85%, 90%, 95%, or greater than 95%) of the cell penetration properties. In certain embodiments, the humanized antibody or antibody fragment has one or more preferable cell penetration characteristics, such as improved penetration efficiency. In other embodiments, the humanized antibody or antibody fragment has improved DNA binding activity and/or a different range of DNA substrate affinity or specificity.

As used herein, the term "fragment" or "antigen-binding fragment" of a humanized antibody moiety or "antigen binding fragment" includes any fragment of a humanized internalizing moiety that retains at least the cell-penetration and/or DNA binding properties associated with the murine 3E10 antibody. In this application, the terms "fragment" and "antigen binding fragment" are used interchangeably. Exemplary antibody fragments include scFv fragments, Fab fragments (e.g., Fab' or F(ab')2), and the like.

In some embodiments, the humanized internalizing moiety (e.g., the humanized antibody and antigen binding fragments of the disclosure) is not directly fused to any heterologous agent or not fused or otherwise linked to a therapeutic or toxic heterologous agent. However, in such embodiments, and as described in greater detail below, the internalizing moiety may still be post-translationally modified (e.g., glycosylated or) and/or provided as part of a composition.

In other embodiments, the humanized internalizing moiety (e.g., the antibodies or antigen binding fragments of the disclosure, such as humanized antibodies or antibody binding fragments) is fused to a heterologous agent or a therapeutic or toxic heterologous agent. In some embodiments, the internalizing moiety effects delivery of a heterologous agent into a cell (i.e., penetrate desired cell; transport across a cellular membrane; deliver across cellular membranes to, at least, the cytoplasm). In certain embodiments, this disclosure relates to an internalizing moiety which promotes delivery of a heterologous agent into muscle, liver and/or neuronal cells, as well as certain other cell types. This portion promotes entry of the conjugate into cells. Like the murine, parental antibody, the humanized antibody and antigen binding fragments of the disclosure promote entry into cells via an ENT transporter, such as an ENT2 transporter and/or an ENT3 transporter. Without being bound by theory, ENT2 is expressed preferentially in certain cell types, including muscle (skeletal and cardiac), neuronal and/or liver cells. Accordingly, conjugates (e.g., conjugates in which a humanized antibody or antigen binding fragment of the disclosure is conjugated to a heterologous agent) are delivered into cells, but generally not ubiquitously. Rather, the conjugates may be delivered with some level of enrichment for particular tissues, including skeletal muscle, cardiac muscle, diaphragm, liver and neurons.

In certain embodiments, the internalizing moiety is capable of binding polynucleotides (e.g., a target/antigen for an antibody of the disclosure is DNA). This is consistent with the properties of the 3E10 antibody which is known to bind DNA (e.g., to specifically bind DNA). In certain embodiments, the internalizing moiety is capable of binding DNA. In certain embodiments, the internalizing moiety is capable of binding DNA with a $K_D$ of less than 100 nM. In certain embodiments, the internalizing moiety is capable of binding DNA (e.g., single stranded DNA or blunt double stranded DNA) with a $K_D$ of less than 500 nM, less than 100 nM, less than 75 nM, less than 50 nM, or even less than 30 nM, less than 20 nM, less than 10 nM, or even less than 1 nM. $K_D$ can be measured using Surface Plasmon Resonance (SPR) or Quartz Crystal Microbalance (QCM), or by ELISA, in accordance with currently standard methods. By way of example, an antibody or antibody fragment comprising a VH having the amino acid sequence set forth in SEQ ID NO: 2 and a VL having an amino acid sequence set forth in SEQ ID NO: 3 specifically binds DNA with a $K_D$ of less than 100 nM, and is an example of an anti-DNA antibody. In certain embodiments, the internalizing moiety binds double-stranded, blunt DNA, and DNA binding activity is or can be demonstrated in a binding assay using blunt DNA (see, for example, Xu et. Al. (2009) EMBO Journal 28: 568-577; Hansen et al., (2012) Sci Translation Med 4: DOI 10.1126/scitranslmed.3004385), such as by ELISA, QCM, or Biacore. In certain embodiments, the internalizing moiety is an anti-DNA antibody. Thus, in certain embodiments, an internalizing moiety (e.g., an antibody or antigen binding fragment) for use alone or associated with a heterologous agent comprises an antibody or antibody fragment that can transit cellular membranes into the cytoplasm and/or the nucleus and is capable of binding to DNA. In certain embodiments, the antibody and antigen binding fragments of the disclosure, such as humanized antibodies and antigen binding fragments, are based upon a murine, parental 3E10 antibody having VH and VL domains, as described above.

Preferably, the humanized antibody has the same, substantially the same, or even improved cell penetration and/or DNA binding characteristics in comparison to the murine, parental antibody, including a murine parental antibody comprising, when present, a murine constant domain.

In certain embodiments, the antibodies and antigen binding fragments of the disclosure have the same CDRs, as defined using the IMGT system, as the murine, parent antibody (e.g., the antibody comprising a heavy chain comprising a VH comprising the amino acid sequence set forth in SEQ ID NO: 17 and a light chain comprising a VL comprising the amino acid sequence set forth in SEQ ID NO: 18). In certain embodiments, the antibodies and antigen binding fragments of the disclosure have at least one CDR of the heavy chain and/or the light chain that differs from that of the murine, parent antibody (e.g., differ at VH CDR2 and/or VL CDR2 and/or VL CDR1, according to Kabat). In some embodiments, a humanized antibody or antigen binding fragment of the disclosure comprises a $V_H$ domain and a $V_L$ domain comprising:

a VH CDR1 having the amino acid sequence of SEQ ID NO: 27;

a VH CDR2 having the amino acid sequence of SEQ ID NO: 28;

a VH CDR3 having the amino acid sequence of SEQ ID NO: 29;

a VL CDR1 having the amino acid sequence of SEQ ID NO: 30;

a VL CDR2 having the amino acid sequence of SEQ ID NO: 31; and a VL CDR3 having the amino acid sequence of SEQ ID NO: 32, which CDRs are in accordance with the IMGT system.

In some embodiments, a humanized antibody or antigen binding fragment of the disclosure comprises a $V_H$ domain and a $V_L$ domain comprising:

a VH CDR1 having the amino acid sequence of SEQ ID NO: 19;

a VH CDR2 having the amino acid sequence of SEQ ID NO: 20; and a VH CDR3 having the amino acid sequence of SEQ ID NO: 21, which CDRs are according to Kabat; and a VL CDR1 having the amino acid sequence of SEQ ID NO: 30;

a VL CDR2 having the amino acid sequence of SEQ ID NO: 31; and a VL CDR3 having the amino acid sequence of SEQ ID NO: 32, which CDRs are according to the IMGT system.

In some embodiments, a humanized antibody or antigen binding fragment of the disclosure comprises a $V_H$ domain and a $V_L$ domain comprising:

a VH CDR1 having the amino acid sequence of SEQ ID NO: 27;

a VH CDR2 having the amino acid sequence of SEQ ID NO: 28; and a VH CDR3 having the amino acid sequence of SEQ ID NO: 29, which CDRs are according to the IMGT system, and a VL CDR1 having the amino acid sequence of SEQ ID NO: 22;

a VL CDR2 having the amino acid sequence of SEQ ID NO: 23; and a VL CDR3 having the amino acid sequence of SEQ ID NO: 24, which CDRs are according to Kabat.

In certain embodiments, an antibody or antigen binding fragment of the disclosure comprises a $V_H$ domain comprising:

a VH CDR1 having the amino acid sequence of SEQ ID NO: 19;

a VH CDR2 having the amino acid sequence of SEQ ID NO: 37; and a VH CDR3 having the amino acid sequence of SEQ ID NO: 21, which CDRs are according to the Kabat system, and a $V_L$ domain comprising a VL CDR1 having the amino acid sequence of SEQ ID NO: 22 or 38;

a VL CDR2 having the amino acid sequence of SEQ ID NO: 39; and a VL CDR3 having the amino acid sequence of SEQ ID NO: 24, which CDRs are according to Kabat.

As detailed throughout the application, the antibody or antigen-binding fragments of the disclosure, such as humanized antibody or antigen binding fragments, can be compared to the murine, parent antibody or to the original 3E10 antibody or antigen binding fragment thereof. Additionally or alternatively, antibodies of the disclosure (or antigen binding fragments thereof) can be compared to alternate antibodies and fragments (e.g., other humanized antibodies based on the same murine parent). In such scenarios, the comparison could be to an alternate antibody or antigen binding fragment have the foregoing 6 IMGT or Kabat CDRs, but have one or more changes in the framework regions relative to the humanized antibody or antigen-binding fragment of the disclosure. Also contemplated are antibodies or antigen binding fragments having the CDRs disclosed herein, but with one, two, three, or four amino acid substitutions in one or more CDRs (e.g., with one substitution in one CDR, with two substitution—one in each of two CDRS, or with three substitutions—one in each of three CDRs). When comparing activity, the ability and efficiency to penetrate cells, such as muscle, liver and/or neuronal cells, via ENT2 and/or ENT3 may be assessed. Activity will be considered comparable or substantially the same if it is approximately 70%, 75%, 80%, 85%, 90%, 95%, or greater than about 95% the activity of the murine, parental antibody. Activity is considered improved, relative to the murine, parental antibody, if a characteristic is at least about 5%, preferably at least about 10% better (e.g., approximately 105%, 110%, 115%, 120%, 125%, 130%, 150%, or greater than 150% the activity of the murine, parental antibody or an alternate humanized antibody). In certain embodiments, an activity is considered improved, relative to another antibody, if a characteristic is at least 2-fold better. In other embodiments, an activity is considered improved if a characteristic is at least 3-, 4-, 5-, 6-, 8, or 10-fold better.

In some embodiments, antibodies or humanized antibodies may comprise antibody fragments, derivatives or analogs thereof, including without limitation: antibody fragments comprising an antigen binding fragments (e.g., Fv fragments, single chain Fv (scFv) fragments, Fab fragments, Fab' fragments, F(ab')2 fragments, single domain antibodies, and multivalent versions of the foregoing; multivalent internalizing moieties including without limitation: Fv fragments, single chain Fv (scFv) fragments, Fab fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In certain embodiments, the antigen-binding fragment is an scFv and a peptide linker interconnects the VH domain and the VL domain. In some embodiments, the antibodies or variants thereof may comprise a constant region that is a hybrid of several different antibody subclass constant domains (e.g., any combination of IgG1, IgG2a, IgG2b, IgG3 and IgG4).

In certain embodiments, the internalizing moiety is an antibody fragment comprising an antigen binding fragment. In other words, in certain embodiments, the internalizing moiety is not a full length antibody but is a fragment thereof comprising an antigen binding fragment. In certain embodiments, the internalizing moiety is an scFv, Fab, Fab', or Fab2'. In certain embodiments, the internalizing moiety is a full length antibody comprising a heavy chain comprising a CH1, hinge, CH2, and CH3 domains, optionally substituted to reduce effector function, such as in the hinge and/or CH2 domains, as described herein. In certain embodiments, the heavy chain comprises a VH domain, and a constant domain comprising a CH1, hinge, CH2, and CH3 domain. In certain embodiments, a heavy chain comprises a VH domain, and a constant domain comprising a CH1 domain and, optionally the upper hinge. The upper hinge may include, for example, 1, 2, 3, or 4 amino acid residues of the hinge region. In certain embodiments, the upper hinge does not include a cysteine residue. In certain embodiments, the upper hinge includes one or more consecutive residues N-terminal to a cysteine that exists in the native hinge sequence. In certain embodiments, the heavy chain comprises a CH region, and a constant domain comprising a CH1 domain and a hinge. In certain embodiments, the hinge (whether present as part of a full length antibody or an antibody fragment) comprises a C to S substitution at a position corresponding to Kabat position 222 (e.g., a C222S in the hinge, where the variation is at a position corresponding to Kabat position 222). In other words, in certain embodiments, the internalizing moiety comprises a serine residue, rather than a cysteine residue, in a hinge domain at a position corresponding to Kabat 222. In certain embodiments, the heavy chain comprises a constant domain comprising a CH1, hinge, CH2 and, optionally CH3 domain. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In certain embodiments, an antibody or antigen binding fragment as disclosed herein is a full length antibody comprising CH1, hinge, CH2, and CH3 of a heavy chain constant domain and a light chain constant domain. In certain embodiments the heavy chain constant region comprises one or more of a CH1, CH2, and CH3 domains, optionally with a hinge.

Monoclonal antibody 3E10 can be produced by hybridoma 3E10 placed permanently on deposit with the American Type Culture Collection (ATCC) under ATCC accession number PTA-2439 and is disclosed in U.S. Pat. No. 7,189,396. This antibody has been shown to bind DNA. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used also herein to refer to a murine antibody (or antigen binding fragment) comprising the a VL domain comprising the amino acid sequence of SEQ ID NO: 18 and a VH domain comprising the amino acid sequence of SEQ ID NO:17, regardless of the method used to produce the antibody. Thus, in the context of the present application, 3E10 antibody will refer, unless otherwise specified, to an antibody having the sequence of the hybridoma or comprising a variable heavy chain domain comprising the amino acid sequence set forth in SEQ ID NO: 17 (which has a one amino acid substitution relative to that of the 3E10 antibody deposited with the ATCC, as described herein and previously demonstrated as retaining cell penetration and DNA binding activity) and the variable light chain domain comprising the amino acid sequence set forth in SEQ ID NO: 18. However, in the context of the present disclosure, the parent murine antibody used as the basis for humanization was an antibody comprising the VL domain comprising the amino acid sequence of SEQ ID NO: 18 and a VH domain comprising the amino acid sequence of SEQ ID NO: 17. The disclosure provides, in certain embodiments, humanized antibodies based on murine 3E10.

Similarly, when referring to variants or antigen-binding fragments of 3E10, such terms are used without reference to the manner in which the antibody was produced. At this point, 3E10 is generally produced recombinantly.

The humanized internalizing moiety may also be derived from variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative substitutions are introduced into the heavy chain, the light chain and/or the constant region(s) of the antibody. In some embodiments, the light chain or heavy chain may be modified at the N-terminus or C-terminus. Moreover, the antibody or antibody fragment may be modified to facilitate conjugation to a heterologous agent. Similarly, the foregoing description of variants applies to antigen binding fragments. Any of these antibodies, variants, or fragments may be made recombinantly by expression of the nucleotide sequence(s) in a host cell. Such internalizing moieties can transit cells via an ENT transporter, such as ENT2 and/or ENT3 and/or bind the same epitope (e.g., target, such as DNA) as 3E10.

The humanized internalizing moiety may also be derived from mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain or the light chain. Numerous variants of mAb 3E10 have been characterized in, e.g., U.S. Pat. No. 7,189,396 and WO 2008/091911, the teachings of which are incorporated by reference herein in their entirety. In the examples provided herein, the parent, murine 3E10 comprises a VH comprising the amino acid sequence set forth in SEQ ID NO: 17 and a VL comprising the amino acid sequence set forth in SEQ ID NO: 18.

In certain embodiments, the internalizing moiety is an antigen binding fragment, such as a humanized single chain Fv (scFv). In other embodiments, the humanized antibody is a Fab' fragment.

In some embodiments, the internalizing moiety is an antibody or antibody fragment comprising an immunoglobulin heavy chain constant region or fragment thereof. As is known, each immunoglobulin heavy chain constant region comprises four or five domains. The domains are named sequentially as follows: $C_H1$-hinge-$C_H2$-$C_H3$ (-$C_H4$). The DNA sequences of the heavy chain domains have cross-homology among the immunoglobulin classes, e.g., the $C_H2$ domain of IgG is homologous to the $C_H2$ domain of IgA and IgD, and to the $C_H3$ domain of IgM and IgE. As used herein, the term, "immunoglobulin Fc region" is understood to mean the carboxyl-terminal portion of an immunoglobulin heavy chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In one embodiment, the immunoglobulin Fc region comprises at least an immunoglobulin hinge region a CH2 domain and a CH3 domain, and lacks the CH1 domain. In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region may comprise at least a portion of a hinge domain, and preferably at least a portion of a CH3 domain of Fc γ or the homologous domains in any of IgA, IgD, IgE, or IgM. Furthermore, it is contemplated that substitution or deletion of amino acids within the immunoglobulin heavy chain constant regions may be useful in the practice of the disclosure. In certain embodiments, the constant region domains are human. In some embodiments, the Fc portion of any of the internalizing moieties described herein has been modified such that it does not induce antibody-dependent cell-mediated cytotoxicity (ADCC). In some embodiments, the Fc portion has been modified such that it does not bind complement. In certain embodiments, a CH2 domain comprises an N to Q substitution at a position corresponding to Kabat position 297 (e.g., a N297Q in a CH2 domain, wherein the variation is at a position corresponding to Kabat position 297). In other words, in certain embodiments, the internalizing moiety comprises a glutamine, rather than an asparagine, at a position corresponding to Kabat position 297.

In some embodiments, the antibody or antigen binding fragment comprises hybrid heavy chain constant regions, i.e., the antibody or antigen binding fragment comprise multiple heavy chain constant region domains selected from: a CH1 domain, a CH2 domain, a CH3 domain, and a CH4 domain; wherein at least one of the constant region domains in the antibody or antigen binding fragment is of a class or subclass of immunoglobulin distinct from the class or subclass of another domain in the antibody or antigen binding fragment. In some embodiments, at least one of the constant region domains in the antibody or antigen binding fragment is an IgG constant region domain, and at least one of the constant region domains in the antibody or antigen binding fragment is of a different immunoglobulin class, i.e., an IgA, IgD, IgE, or IgM constant region domain. In some embodiments, at least one of the constant region domains in the antibody or antigen binding fragment is an IgG1 constant region domain, and at least one of the constant region domains in the antibody or antigen binding fragment is of a different IgG subclass, i.e., an IgG2A, IgG2B, IgG3 or IgG4. Suitable constant regions may be human or from another species (e.g., murine). Humanized antibodies and antigen binding fragments of the disclosure are consider humanized regardless of whether and constant region sequence (heavy or light chain), if present, corresponds to that of a human immunoglobulin or corresponds to that of another species.

The cell penetrating ability of the humanized internalizing moieties or fragments or variants may be utilized to promote delivery of a heterologous agent. Humanized moieties derived from 3E10 are particularly well suited for this because of their demonstrated ability to effectively promote delivery to muscle, liver and neuronal cells. Thus, humanized internalizing moieties are especially useful for promoting effective delivery into cells in subjects, such as human patients or model organisms. In certain embodiments, antibodies and antigen binding fragments of the disclosure are useful as intermediates for further conjugation to a heterologous agent, such as a heterologous protein, peptide, polynucleotide, or small molecule. However, in other embodiments, the humanized internalizing moieties or fragments or variants are not utilized to deliver any heterologous agent.

Preparation of antibodies or fragments thereof (e.g., a single chain Fv fragment encoded by $V_H$-linker-$V_L$ or $V_L$-linker-$V_H$) is well known in the art. In particular, methods of recombinant production of mAb 3E10 antibody fragments have been described in WO 2008/091911. Further, methods of generating scFv fragments of antibodies are well known in the art. When recombinantly producing an antibody or antibody fragment, a linker may be used. For example, typical surface amino acids in flexible protein regions include Gly, Asn and Ser. One exemplary linker is provided in SEQ ID NO: 6, 13 or 14. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)n$, wherein n is an integer from 1-10, such as 2, 3, or 4. Other near neutral amino acids, such as Thr and Ala, can also be used in the linker sequence.

In addition to linkers interconnecting portions of, for example, an scFv, the disclosure contemplates the use of additional linkers to, for example, interconnect the heterologous agent to the antibody portion of a conjugate or to interconnect the heterologous agent portion to the antibody portion of conjugate.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the humanized internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising an peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

A "Fab fragment" is comprised of one light chain and the $C_H1$ and variable regions of one heavy chain. Generally, the heavy chain of a Fab molecule cannot form a disulfide bond with another heavy chain molecule. A Fab may optionally include a portion of the hinge, such as the upper hinge.

A "Fab' fragment" contains one light chain and one heavy chain that contains more of the constant region, between the $C_H1$ and $C_H2$ domains, such that an interchain disulfide bond can be formed between two heavy chains to form a F(ab')$_2$ molecule.

A "F(ab')$_2$ fragment" contains two light chains and two heavy chains containing a portion of the constant region between the CH1 and CH2 domains, such that an interchain disulfide bond is formed between two heavy chains.

Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains (CH). Each light chain has a variable domain at one end (VL) and a constant domain (CL) at its other end; the constant domain of the light chain is aligned with the first constant domain of the heavy chain, and the light chain variable domain is aligned with the variable domain of the heavy chain. Light chains are classified as either lambda chains or kappa chains based on the amino acid sequence of the light chain constant region. The variable domain of a kappa light chain may also be denoted herein as VK.

The antibodies of the disclosure include full length or intact antibody, antibody fragments, native sequence antibody or amino acid variants, human, humanized (a form of chimeric antibodies), post-translationally modified, chimeric antibodies, immunoconjugates, and functional fragments thereof. The antibodies can be modified in the Fc region to provide desired effector functions or serum half-life.

Preparation of Antibodies

Naturally occurring antibody structural units typically comprise a tetramer. Each such tetramer typically is composed of two identical pairs of polypeptide chains, each pair having one full-length "light" chain (typically having a molecular weight of about 25 kDa) and one full-length "heavy" chain (typically having a molecular weight of about 50-70 kDa). The amino-terminal portion of each chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. See, e.g., Fundamental Immunology, Ch. 7, 2.sup.nd ed., (Paul, W., ed.), 1989, Raven Press, N.Y. (incorporated by reference in its entirety for all purposes). The combination of the variable regions of each light chain/heavy chain pair typically forms the antigen-binding site. In some embodiments, antibodies or antigen binding fragments of the disclosure comprise the following constant domain scheme: IgG2a CH1-IgG1 hinge-IgG1 CH2-CH3. Other suitable combinations are also contemplated. In other embodiments, the antibody comprises a full length antibody and the CH1, hinge, CH2, and CH3 is from the same constant domain subclass (e.g., IgG1). In some embodiments, the antibodies or antigen binding fragment comprises an antigen binding fragment comprising a portion of the constant domain of an immunoglobulin, for example, the following constant domain scheme: IgG2a CH1-IgG1 upper hinge. In some embodiments, the antibodies or antigen binding fragments of the disclosure comprise a kappa constant domain (e.g., SEQ ID NO: 12).

The variable regions of each of the heavy chains and light chains typically exhibit the same general structure comprising four relatively conserved framework regions (FR) joined by three hyper variable regions, also called complementarity determining regions or CDRs. The CDRs from the two chains of each pair typically are aligned by the framework regions, which alignment may enable binding to a specific target (e.g., antigen, DNA in the context of the present disclosure). From N-terminal to C-terminal, both light and heavy chain variable regions typically comprise the domains FR1, CDR1, FR2, CDR2, FR3, CDR3 and FR4. The assignment of amino acids to each domain (FR or CDR) is typically in accordance with the definitions of Kabat Sequences of Proteins of Immunological Interest (1987 and 1991, National Institutes of Health, Bethesda, Md.). In certain embodiments, the CDRs of a particular antibody, such as an antibody provided herein, are CDRs, as defined by this Kabat system (e.g., the CDRs being referred to for an antibody or antigen binding fragment are identified using the Kabat system). Similarly, in certain embodiments, particularly when the CDRs are defined or identified as by the Kabat system, the FR regions are also defined and/or identified using the Kabat system. However, alternative systems for identifying CDR and FR regions are also available, including the IMGT system (described herein). In certain embodiments, the CDRs of a particular antibody, such as an antibody provided herein, are CDRs as defined by the IMGT system (e.g., CDRs for an antibody or antigen binding fragment are identified using the IMGT system).

Antibodies became useful and of interest as pharmaceutical agents with the development of monoclonal antibodies. Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63). In many cases, hybridomas are used to generate an initial antibody of murine or rodent origin. That initial antibody may then be modified, such as using recombinant techniques to produce rodent variants, chimeric antibodies, humanized antibodies and the like. Other methods exist to produce an initial antibody, and such methods are known in the art. However, regardless of the method used to generate an initial antibody or even a variant of that initial antibody, any given antibody of non-human origin can then be modified to increase its humanness.

It can be advantageous to increase the humanness of a non-human antibody to make it more suitable for use in human subject and cells, whether for diagnostic, therapeutic, or research purposes. Antibodies may be modified for use as therapeutics. Examples of such antibodies (including antibody fragments) include chimeric, humanized, and fully human antibodies. Numerous methods exist in the art for the generation of chimeric, humanized and human antibodies. In the context of the present disclosure, an antibody is considered humanized if at least one of the VH domain or VL domain is humanized. Moreover, an VH or VL domain is humanized if the amino acid sequence of at least a portion of at least one FR regions has been modified, relative to a parent murine antibody, such that the amino acid sequence of that portion corresponds to that of a human antibody or a human consensus sequence. In certain embodiments, at least one, two, three, or four FR regions of the VH domain and/or at least one, two, three, or four FR regions of the VL domain have been modified (in whole or in part) so that their sequence is more closely related to a human sequence. For any of the foregoing in certain embodiments, a humanized antibody fragment may be provided in the context of a human or non-human light chain and/or heavy chain constant region (e.g., comprising a CL and one or more of a CH1, hinge, CH2, and/or CH3 domains). In certain embodiments, a humanized antibody or antigen binding fragment of the disclosure is provided in the context of human light and/or heavy chain constant domains, when present. Numerous examples of humanized light and heavy chain variable domains based on a 3E10 parent antibody are provided herein. Antibodies and antibody binding fragments combining any of the humanized light chain variable domains and/or heavy chain variable domains described herein are exemplary of antibodies and antigen binding fragments of the disclosure.

Once the nucleotide sequences encoding such antibodies have been determined, chimeric or humanized antibodies may be produced by recombinant methods. Nucleic acids encoding the antibodies are introduced into host cells and expressed using materials and procedures generally known in the art.

In certain embodiments, the antibodies or antigen binding fragments of the disclosure are of the IgG1, IgG2, or IgG4 isotype. In certain embodiments of the disclosure, the antibodies comprise a human kappa light chain and a human IgG1, IgG2, or IgG4 heavy chain. In certain embodiments, the antibodies of the disclosure have been cloned for expression in mammalian cells.

Regardless of when an antibody of the disclosure is a full length antibody or an antigen binding fragment, antibodies and antigen binding fragments of the disclosure can be recombinantly expressed in cell lines. In these embodiments, sequences encoding particular antibodies can be used for transformation of a suitable host cell, such as a mammalian host cell or yeast host cell. According to these embodiments, transformation can be achieved using any known method for introducing polynucleotides into a host cell, including, for example packaging the polynucleotide in a virus (or into a viral vector) and transducing a host cell with the virus (or vector) or by transfection procedures known in the art. Generally, the transformation procedure used may depend upon the host to be transformed. Methods for introducing heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

According to certain embodiments of the disclosure, a nucleic acid molecule encoding the amino acid sequence of a heavy chain constant region (all or a portion), a heavy chain variable region of the disclosure, a light chain constant region, or a light chain variable region of the disclosure is inserted into an appropriate expression vector using standard ligation techniques. In a preferred embodiment, the heavy or light chain constant region is appended to the C-terminus of the appropriate variable region and is ligated into an expression vector. The vector is typically selected to be functional in the particular host cell employed (i.e., the vector is compatible with the host cell machinery such that amplification of the gene and/or expression of the gene can occur). For a review of expression vectors, see, Goeddel (ed.), 1990, Meth. Enzymol. Vol. 185, Academic Press. N.Y. In the context of antibody expression, both the heavy and light chain may be expressed from the same vector (e.g., from the same or different promoters present on the same vector) or the heavy and light chains may be expressed from different vectors. In certain embodiments, the heavy and light chains are expressed from different vectors which are transfected into the same host cell and co-expressed. Regardless of when the heavy and light chains are expressed in the same host cell from the same or a different vector, the chains can then associate to form an antibody (or antibody fragment, depending on the portions of the heavy and light chain being expressed).

In some embodiments, an antibody or antigen binding fragment of the disclosure is not conjugated to a heterologous agent. In other embodiments, an antibody or antigen binding fragment of the disclosure is conjugated to a heterologous agent. In certain embodiments, the heterologous agent is a protein or peptide. That protein or peptide may be expressed as an inframe, co-translation fusion protein with, for example, the heavy chain, and expressed as described herein. Chemical conjugation is also possible. Conjugated as described in detail herein and unless otherwise specified, refers to scenarios where any of the antibody or antigen binding portions of the disclosure are associated with or interconnected with the heterologous agent, regardless of the interconnection (e.g., the interconnection/association may comprise a chemical conjugation, covalent bond, di-sulfide bond, etc. or combinations thereof). In certain embodiments, at least a portion of the interconnection is via a covalent bond, such as the forming of a fusion protein between a heavy chain of the antibody of the disclosure and the heterologous agent (which may further associate with a light chain of the antibody of the disclosure). Accordingly, the disclosure provides such conjugates and pharmaceutical compositions comprising such conjugates. A conjugate is a molecule comprising an antibody or antigen binding portion of the disclosure associate with a heterologous agent. Similarly, antibodies or antigen binding fragments of the disclosure may further comprise a heterologous agent. Conjugates along molecules where the two portions are associated or interconnected (e.g., the interconnection may comprise a chemical conjugation, covalent bond, di-sulfide bond, etc. or combinations thereof). In certain embodiments, at least a portion of the interconnection is via a covalent bond, such as the forming of a fusion protein between a heavy chain of an antibody of the disclosure and the heterologous agent (which may further associate with a light chain of the antibody or antibody fragment of the disclosure).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. These portions of vectors are well known, and there are numerous generally available vectors that can be selected and used for the expression of proteins. One can readily selected vectors based on the desired host cell and application.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

The expression and cloning vectors of the disclosure will typically contain a promoter that is recognized by the host organism and operably linked to the molecule encoding heavy and/or light chain. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding the heavy chain or light chain comprising an antibody or antigen binding fragment of the disclosure. In certain embodiments, the same promoter is used for both the heavy and light chain. In other embodiments, different promoters (present on the same or different vectors) are used for each.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: the SV40 early promoter region (Bernoist and Chambon, 1981, Nature 290:304-10); the CMV promoter; the promoter contained in the 3' long terminal repeat of Rous sarcoma virus (Yamamoto et al., 1980, Cell 22:787-97); the herpes thymidine kinase promoter (Wagner et al., 1981, Proc. Natl. Acad. Sci. USA 78:1444-45); the regulatory sequences of the metallothionine gene (Brinster et al., 1982, Nature 296:39-42); prokaryotic expression vectors such as the beta-lactamase promoter (Villa-Kamaroff et al., 1978, Proc. Natl. Acad. Sci. USA 75:3727-31); or the tac promoter (DeBoer et al., 1983, Proc. Natl. Acad. Sci. USA 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-46; Ornitz et al., 1986, Cold Spring Harbor Symp. Quant. Biol.

50:399-409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol. 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol. 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315:338-40; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234:1372-78).

The vector may also include an enhancer sequence to increase transcription of DNA encoding light chain or heavy chain.

Expression vectors of the disclosure may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain or heavy chain or light chain and heavy chain comprising an antibody or antigen binding fragment of the disclosure has been inserted into the proper site of the vector, the completed vector may be inserted into a suitable host cell for amplification and/or polypeptide expression. The transformation of an expression vector into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., supra.

The host cell, when cultured under appropriate conditions, synthesizes the antibody or antigen binding fragment of the disclosure that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (A.T.C.C.), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In another embodiment, one may select a cell line from the B cell lineage that does not make its own antibody but has a capacity to make and secrete a heterologous antibody (e.g., mouse myeloma cell lines NSO and SP2/0). In other embodiments, a cell other than a mammalian cell is used, such as a yeast cell line (e.g., *Pichia*).

In certain embodiments, the cell line stably expresses an antibody or antigen binding fragment of the disclosure. In other embodiments, the cells transiently express an antibody or antigen binding fragment of the disclosure.

In certain embodiments is provided antibodies of the disclosure (including antigen binding fragments) that are substantially purified/isolated. Numerous methods, filters, and devices for substantially purifying antibodies grown in recombinant cell culture are available.

Antibody fragments can also be made by enzymatic digestion of a full length antibody.

In certain embodiments, the antibodies or antigen binding fragments of the disclosure, whether provided alone or as conjugates with a heterologous agent, are detectably labeled. In certain embodiments, the detectable label is itself an example of a heterologous agent. Methods for conjugation to a substance, such as a detectable label, are well known in the art. In one embodiment, the attached substance is a detectable label (also referred to herein as a reporter molecule). Suitable substances for attachment to include, but are not limited to, a fluorophore, a chromophore, a dye, a radioisotope, and combinations thereof. Methods for conjugation or covalently attaching another substance to an antibody are well known in the art.

The terms "label" or "labeled" refers to incorporation of a detectable marker, e.g., by incorporation of a radiolabeled amino acid or attachment to a polypeptide of biotin moieties that can be detected by marked avidin (e.g., streptavidin preferably comprising a detectable marker such as a fluorescent marker, a chemiluminescent marker or an enzymatic activity that can be detected by optical or colorimetric methods). Various methods of labeling polypeptides and glycoproteins are known in the art and may be used advantageously in the methods disclosed herein. Examples of labels for polypeptides include, but are not limited to, the following: radioisotopes or radionuclides (e.g., $^{3}$H, $^{14}$C, $^{15}$N, $^{35}$S, $^{90}$Y, $^{99m}$Tc, $^{111}$In, $^{125}$I, $^{131}$I). In certain embodiments, the label is a radioactive isotope. Examples of suitable radioactive materials include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In,), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$SM, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh and $^{97}$Ru.).

Further examples of labels include fluorescent labels (e.g., fluoroscein isothiocyanate (FITC), rhodamine, or lanthanide phosphors), enzymatic labels (e.g., horseradish peroxidase, β-galactosidase, luciferase, alkaline phosphatase), chemiluminescent labels, hapten labels such as biotinyl groups, and predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

When present, regardless of the particular label, one of skill can select an appropriate label to facilitate purification, diagnostic, or research use. In other embodiments, the heterologous agent is a therapeutic molecule and either does not include a detectable label and/or epitope tag, or includes a therapeutic molecule in addition to the detectable label and/or epitope tag.

"Humanized" refers to an immunoglobulin such as an antibody, wherein the amino acids directly involved in antigen binding, the so-called complementary determining regions (CDR), of the heavy and light chains are not necessarily of human origin, while at least a portion of the rest of the variable domain (e.g., one or more of FR1, FR2, FR3, FR4) of one or both chains of the immunoglobulin molecule, the so-called framework regions of the variable heavy and/or light chains, and, if present, optionally the constant regions of the heavy and light chains are modified so that their amino acid sequence more closely correspond to human sequences.

A "humanized antibody" as used herein in the case of a two or greater chain antibody is one where at least one chain is humanized. A humanized antibody chain has a variable region where one or more of the framework regions are human or contain alterations, relative to a murine parent, so that one or more framework regions are more human than a murine parent. A humanized antibody which is a single chain is one where the chain has a variable region where one or more of the framework regions are human or contain alterations, relative to a murine parent, so that one or more framework regions are more human. The non-human portions of the variable region of the humanized antibody chain or antigen-binding fragment is derived from a non-human source, particularly a non-human antibody, typically of rodent origin. The non-human contribution to the humanized antibody is typically provided in the form of at least one CDR region which is interspersed among framework regions derived from one (or more) human immunoglobulin(s). In addition, framework support residues may be altered to preserve binding affinity. Thus, as is understood in the art, an entire framework region or all of the framework regions on a particular chain need not contain residues corresponding to a human antibody in order for the antibody to be considered humanized.

A "humanized antibody" may further comprise constant regions (e.g., at least one constant region or portion thereof, in the case of a light chain, and in some embodiments three constant regions in the case of a heavy chain). The constant regions of a humanized antibody, if present, typically are human in origin.

In some embodiments, a humanized antibody is generated by first subjecting a murine 3E10 light or heavy chain antibody sequence (e.g., the murine 3E10 antibody light and heavy chain amino acid sequences of SEQ ID NO: 18 and 17, respectively) to a sequence database search (e.g., BLAST) in order to identify the top closest human immunoglobulin kappa or heavy chain homologues in sequence similarity (e.g., the top 1, 2, 3, 4, 5, 6, 7, 8, 9 or 10 closest immunoglobulin kappa or heavy chain homologues). The top closest human immunoglobulin kappa or heavy chain homologues are considered candidates for kappa or heavy chain CDR grafting. In some embodiments, sequence alignment tools, such as Vector NTi sequence alignment tools, are then used to analyze the chimeric amino acid sequences consisting of the CDRs from the 3E10 kappa or heavy chain and the framework regions of any one of the top human immunoglobulin kappa or heavy chain homologues.

In general, as used herein, humanized antibodies comprise one or two variable domains in which all or part of the CDR regions correspond to parts derived from the non-human parent sequence and in which all or part of the FR regions are derived from a human immunoglobulin sequence. The humanized antibody can then, optionally, comprise at least one portion of a constant region of immunoglobulin (Fc), in particular that of a selected reference human immunoglobulin.

In some embodiments, the antibodies and antigen binding fragments of the disclosure (e.g., an antibody or antigen binding fragment, such as a humanized antibody or antigen binding fragment) comprises one or more of the CDRs of the 3E10 antibody. In certain embodiments, the antibodies and antigen binding fragments comprise one or more of the CDRs of a 3E10 antibody comprising a $V_H$ domain comprising the amino acid sequence set forth in SEQ ID NO: 17 and a $V_L$ domain comprising the amino acid sequence set forth in SEQ ID NO: 18. Either or both of the Kabat or IMGT CDRs may be used to refer to or describe an antibody. CDRs of the 3E10 antibody or an antibody of the disclosure may be determined using any of the CDR identification schemes available in the art, and such scheme may be used to describe the antibody. For example, in some embodiments, the CDRs are defined according to the Kabat definition as set forth in Kabat et al. Sequences of Proteins of Immunological Interest, 5th Ed. Public Health Service, National Institutes of Health, Bethesda, Md. (1991). In other embodiments, the CDRs are defined according to Chothia et al., 1987, J Mol Biol. 196: 901-917 and Chothia et al., 1989, Nature. 342:877-883. In other embodiments, the CDRs are defined according to the international ImMunoGeneTics database (IMGT) as set forth in LeFranc et al., 2003, Development and Comparative Immunology, 27: 55-77. In other embodiments, the CDRs of the 3E10 antibody are defined according to Honegger A, Pluckthun A., 2001, J Mol Biol., 309:657-670. In some embodiments, the CDRs are defined according to any of the CDR identification schemes discussed in Kunik et al., 2012, PLoS Comput Biol. 8(2): e1002388. In certain embodiments, antibodies and antigen binding fragments of the disclosure comprise one or more differences in the Kabat CDRs as compared to the murine, parent antibody. For example, in certain embodiments, the antibodies and antigen binding fragments of the disclosure differ at VH CDR2 and/or VL CDR2 and, optionally, at VL CDR1 in comparison to the murine, parent antibody. However, in certain embodiments, such antibodies share the IMGT CDRs of the murine, parent antibody.

Herein, the amino acid positions of residues in the VH and VL domains are referred to by linear sequence relative to, for example, SEQ ID NO: 17 or 18. Thus, the sequence of the VH and/or VL of an antibody or antigen binding fragment of the disclosure can be described relative to the corresponding amino acid position(s) of SEQ ID NO: 17 or 18. For example, an VH or VL domain may include an alteration at a particular amino acid position, and that position may correspond to a particular position in SEQ ID NO: 17 or 18.

However, the CDR identification scheme also provide numbering systems that may be used to facilitate comparisons between antibodies. Although not specifically used herein, one of skill in the art can readily use the available numbering scheme to refer to the CDRs described herein using a uniform numbering system, rather than by referring to the linear sequence. In certain embodiments, to number residues of an antibody for the purpose of identifying CDRs according to any of the CDR identification schemes known in the art, one may align the antibody at regions of homology of the sequence of the antibody with a "standard" numbered sequence known in the art for the elected CDR identification scheme. Maximal alignment of framework residues frequently requires the insertion of "spacer" residues in the numbering system, to be used for the Fv region. In addition, the identity of certain individual residues at any given site number may vary from antibody chain to antibody chain due to interspecies or allelic divergence. These uniform schemes for numbering residues are not expressly used herein, but can be readily used based on the disclosed sequences and identified CDRs.

In certain embodiments, the antibodies and antigen binding fragments of the disclosure (e.g., a humanized antibody or antigen binding fragment of the disclosure) comprises Kabat CDRs. In some embodiments, the antibodies and antigen binding fragments comprise a $V_H$ CDR1 that corresponds to amino acid residues 31-35 of SEQ ID NO: 17, a $V_H$ CDR2 that corresponds to amino acid residues 50-66 of SEQ ID NO: 17, and/or a $V_H$ CDR3 that corresponds to amino acid residues 99-105 of SEQ ID NO: 17. We note that this numbering of amino acid residues is with reference to the linear amino acid sequence of SEQ ID NO: 17. One of skill in the art can readily use the Kabat system to identify these residues using Kabat numbering. In certain embodiments, the antibodies and antigen binding fragments comprise a $V_L$ CDR1 that corresponds to amino acid residues 24-38 of SEQ ID NO: 18, a $V_L$ CDR2 that corresponds to amino acid residues 54-60 of SEQ ID NO: 18, and/or a $V_L$ CDR3 that corresponds to amino acid residues 93-101 of SEQ ID NO: 18. We note that this numbering of amino acid residues is with reference to the linear amino acid sequence of SEQ ID NO: 18. One of skill in the art can readily use the Kabat system to identify these residues using Kabat numbering.

In certain embodiments, the antibodies and antigen binding fragments of the disclosure comprise CDRs that are defined using the IMGT system. In some embodiments, the antibodies and antigen binding fragments comprise $V_H$ CDR1 that corresponds to amino acid residues 26-33 of SEQ ID NO: 17, a $V_H$ CDR2 that corresponds to amino acid residues 51-58 of SEQ ID NO: 17, and/or a $V_H$ CDR3 that corresponds to amino acid residues 97-105 of SEQ ID NO: 17. We note that this numbering of amino acid residues is with reference to the linear amino acid sequence of SEQ ID NO: 17. In certain embodiments, the antibodies and antigen binding fragments comprise a $V_L$ CDR1 that corresponds to amino acid residues 27-36 of SEQ ID NO: 18, a $V_L$ CDR2 that corresponds to amino acid residues 54-56 of SEQ ID NO: 18, and/or a $V_L$ CDR3 that corresponds to amino acid residues 93-101 of SEQ ID NO: 18. We note that this numbering of amino acid residues is with reference to the linear amino acid sequence of SEQ ID NO: 18. In certain embodiments, an antibody or antigen binding fragment of the disclosure comprises all 6 of the foregoing CDRs. In certain embodiments, the antibody or antigen binding fragment comprises 4 of the foregoing CDRs, and a VH CDR2 as set forth in SEQ ID NO: 37 and a VL CDR 2 as set forth in SEQ ID NO: 39.

In certain embodiments, the antibodies and antigen binding fragments of the disclosure comprise at least 1, 2, 3, 4, or 5 of the CDRs of 3E10 as determined using the Kabat CDR identification scheme (e.g., the CDRs set forth in SEQ ID NOs: 19-24). In certain embodiments, the antibody or antigen binding fragment further comprises a VH CDR2 as set forth in SEQ ID NO: 37 and/or a VL CDR2 as set forth in SEQ ID NO: 38 and/or a VL CDR1 as set forth in SEQ ID NO: 39. In certain embodiments, the antibodies and antigen binding fragments comprise at least 1, 2, 3, 4 or 5 of the CDRS of 3E10 as determined using the IMGT identification scheme (e.g., the CDRs set forth in SEQ ID NOs: 27-32). In certain embodiments, the antibodies and antigen binding fragments comprise all six CDRs of 3E10 as determined using the Kabat CDR identification scheme (e.g., comprises SEQ ID NOs 19-24). In other embodiments, the antibodies and antigen binding fragments comprise all six CDRS of 3E10 as determined using the IMGT identification scheme (e.g., which are set forth as SEQ ID NOs: 27-32). For any of the foregoing, in certain embodiments, the antibodies and antigen binding fragments is an antibody that binds the same epitope (e.g., the same target, such as DNA) as 3E10 and/or the internalizing moiety competes with 3E10 for binding to antigen (e.g., DNA). Exemplary antibodies and antigen binding fragments can transit cells via ENT2 and/or ENT3. In certain embodiments, antibodies or antigen binding fragments of the disclosure comprise 6 of the foregoing CDRs, but include 1, 2 3, or 4 amino acid substitutions in one or more CDRs. For example, the antibodies or antigen binding fragments comprise 3 CDR substitutions: one substitution in each of three CDRs.

In certain embodiments, antibodies or antigen binding fragments of the disclosure (e.g., a humanized antibody or antigen binding fragment of the disclosure) comprise an amino acid sequence having at least one, two, three, four, or five amino acid alterations in one or more CDRs using IMGT numbering (e.g., in one or more CDRs having the amino acid sequence of any one of SEQ ID NOs: 27-32, such as having 1-2, 1-3, 1-4, or 1-5 alternations) or Kabat numbering (e.g., in one or more CDRs having the amino acid sequence of any one of SEQ ID NOs: 19-24, such as having 1-2, 1-3, 1-4, or 1-5 alterations). In certain embodiments, antibodies or antigen binding fragments of the disclosure (e.g., a humanized antibody or antigen binding fragment of the disclosure) comprise an amino acid sequence having at least one, two, three, four, or five amino acid alterations in one or more CDRs using Kabat numbering (e.g., in one or more CDRs having the amino acid sequence of any one of SEQ ID NOs: 19-24, such as have 2, 3, 4, or 5 alterations) In some embodiments, antibodies or antigen binding fragments of the disclosure comprise a $V_L$ domain comprising one or more of the following amino acid alterations: M37L, H38A or E59Q, as compared with and numbered with respect to the linear amino acid sequence of SEQ ID NO: 18. In some embodiments, any of the antibodies or antigen binding fragments disclosed herein comprise a $V_H$ domain comprising a T63 S alteration, as compared with and numbered with respect to the linear amino acid sequence of SEQ ID NO: 17. In some embodiments, antibodies or antigen binding fragments of the disclosure comprise a $V_L$ domain comprising an E59Q alteration as compared with and numbered with respect to the linear amino acid sequence of SEQ ID NO: 18, and a $V_H$ domain comprising a T63S alteration as compared with and numbered with respect to the linear amino acid sequence of SEQ ID NO: 17.

Without wishing to be bound by theory, one of the surprising findings of the present disclosure is the ability to generate antibodies and antigen-binding fragments that—have improved DNA binding activity versus murine 3E10, and further include an amino acid alteration (here, a substitution) in certain Kabat CDRs. Moreover, in certain embodiments, these improved antibodies having CDR substitutions are, in certain embodiments, also humanized.

In certain embodiments, an internalizing moiety of the disclosure, such as an antibody or antibody fragment described herein, binds a given DNA substrate with higher affinity as compared to an antibody or scFv or Fv having the VH and VL of the antibody produced by the hybridoma deposited with the ATCC under ATCC accession number PTA-2439. In certain embodiments, an internalizing moiety for use in the methods of the present disclosure is not an antibody or antibody fragment having the VH and VL of the antibody produced by the hybridoma deposited with the ATCC under ATCC accession number PTA-2439. In some embodiments, an internalizing moiety for use in the methods of the present disclosure is not a murine antibody or antibody fragment.

In certain embodiments, the antibodies and antigen binding fragments of the disclosure comprise a variable heavy chain domain comprising at least one CDR different from the corresponding CDR set forth in SEQ ID NO: 17, as determined using the Kabat CDR identification scheme. In some embodiments, the at least one different CDR is $V_H$ CDR2 as set forth in SEQ ID NO: 37.

In certain embodiments, the antibodies and antigen binding fragments of the disclosure comprise a variable light chain domain comprising at least one CDR different from the corresponding CDR set forth in SEQ ID NO: 18, as determined using the Kabat CDR identification scheme. In some embodiments, the at least one different CDR is a $V_L$ CDR1 as set forth in SEQ ID NO: 38. In some embodiments, the at least one different CDR is a $V_L$ CDR2 as set forth in SEQ ID NO: 39.

Where the acceptor is derived from a human immunoglobulin, one may optionally select a human framework sequence that is selected based on its homology to the donor framework sequence by aligning the donor framework sequence with various human framework sequences in a collection of human framework sequences, and select the most homologous framework sequence as the acceptor. The acceptor human framework may be from or derived from human antibody germline sequences available in public databases.

Regardless of the specific methodologies used to generate a humanized antibody or antibody fragment, the antibody must be evaluated to make sure that it (i) retains the desired function of the parent, murine antibody (or optionally has enhanced function); (ii) does not have deleterious properties that make it difficult to make or use; and preferably (iii) possesses one or more advantageous properties in comparison to the murine, parent antibody. Whether and to what extent any or all of these occur for any specific humanized antibody is unpredictable and uncertain. This is particularly true where substitutions are also introduced into the CDRs. Moreover, amongst a panel of humanized antibodies or antibody fragments, some may not have the required activity and one or more antibodies that do have the required activity may have advantageous properties in comparison to other humanized antibodies. This too is unpredictable and uncertain.

In certain embodiments, the antibodies or antigen-binding fragments of the disclosure comprise a light chain variable (VL) domain and a heavy chain variable (VH) domain; wherein the VL domain is humanized and comprises:
  a VH CDR1 having the amino acid sequence of SEQ ID NO: 27;
  a VH CDR2 having the amino acid sequence of SEQ ID NO: 28; and
  a VH CDR3 having the amino acid sequence of SEQ ID NO: 29; which CDRs are in accordance with the IMGT system
and the VH domain is humanized and comprises:
  a VL CDR1 having the amino acid sequence of SEQ ID NO: 30;
  a VL CDR2 having the amino acid sequence of SEQ ID NO: 31; and
  a VL CDR3 having the amino acid sequence of SEQ ID NO: 32; which CDRs are in accordance with the IMGT system, and wherein the antibody or antigen-binding fragment has increased DNA binding and/or cell penetration, relative to that of a murine 3E10 antibody comprising a light chain variable (VL) domain having the amino acid sequence of SEQ ID NO: 18 and a heavy chain variable (VH) domain having the amino acid sequence of SEQ ID NO: 17.

In certain embodiments the antibodies or antigen-binding fragments of the disclosure comprise a light chain variable (VL) domain and a heavy chain variable (VH) domain; wherein the VH domain comprises:
  a VH CDR1 having the amino acid sequence of SEQ ID NO: 19;
  a VH CDR2 having the amino acid sequence of SEQ ID NO: 37; and
  a VH CDR3 having the amino acid sequence of SEQ ID NO: 21, which CDRs are according to the Kabat system;
and the VL comprises:
  a VL CDR1 having the amino acid sequence of SEQ ID NO: 38;
  a VL CDR2 having the amino acid sequence of SEQ ID NO: 39; and
  a VL CDR3 having the amino acid sequence of SEQ ID NO: 24, which CDRs are according to the Kabat system; wherein the antibody or antigen-binding fragment binds DNA.

In certain embodiments the antibodies or antigen-binding fragments of the disclosure comprise a light chain variable (VL) domain and a heavy chain variable (VH) domain; wherein the VH domain comprises:
  a VH CDR1 having the amino acid sequence of SEQ ID NO: 19;
  a VH CDR2 having the amino acid sequence of SEQ ID NO: 37; and
  a VH CDR3 having the amino acid sequence of SEQ ID NO: 21, which CDRs are according to Kabat;
and the VL comprises:
  a VL CDR1 having the amino acid sequence of SEQ ID NO: 22;
  a VL CDR2 having the amino acid sequence of SEQ ID NO: 39; and
  a VL CDR3 having the amino acid sequence of SEQ ID NO: 24, which CDRs are according to Kabat;
wherein the antibody or antigen-binding fragment binds DNA.

In certain embodiments, antibodies or antigen binding fragments of the disclosure penetrate cells (e.g., can transit the plasma membrane and enter into cells, such as cells expressing ENT2).

In some embodiments, the VH domain is humanized. In some embodiments, the VL domain is humanized.

In certain embodiments the antibodies or antigen-binding fragments of the disclosure comprise a $V_L$ domain that comprises the amino acid sequence set forth in SEQ ID NO: 35, or an amino acid sequence that differs from SEQ ID NO: 35 by the presence of a total of 1, 2, 3, 4, 5, or 6 amino acid substitutions, insertions and/or deletions in the framework regions, as defined by the IMGT system, relative to SEQ ID NO: 35. In other embodiments, the $V_L$ domain comprises the amino acid sequence set forth in SEQ ID NO: 3, or an amino acid sequence that differs from SEQ ID NO: 3 by the presence of a total of 1, 2, 3, 4, 5, or 6 amino acid substitutions, insertions and/or deletions in the framework regions, as defined by the IMGT system, relative to SEQ ID NO: 3. In some embodiments, the VL domain comprises the amino acid sequence set forth in SEQ ID NO: 35. In some embodiments, the VL domain comprises the amino acid sequence set forth in SEQ ID NO: 3.

In certain embodiments the antibodies or antigen-binding fragments of the disclosure comprise a $V_H$ domain that comprises the amino acid sequence set forth in SEQ ID NO: 33, or an amino acid sequence that differs from SEQ ID NO: 33 by the presence of a total of 1, 2, 3, 4, 5, or 6 amino acid substitutions, insertions and/or deletions in the framework regions, as defined by the IMGT system, relative to SEQ ID NO: 33. In some embodiments, the $V_H$ domain comprises the amino acid sequence set forth in SEQ ID NO: 34, or an amino acid sequence that differs from SEQ ID NO: 34 by the presence of a total of 1, 2, 3, 4, 5, or 6 amino acid substitutions, insertions and/or deletions in the framework regions, as defined by the IMGT system, relative to SEQ ID NO: 34. In some embodiments, the $V_H$ domain comprises the amino acid sequence set forth in SEQ ID NO: 2, or an amino acid sequence that differs from SEQ ID NO: 2 by the presence of a total of 1, 2, 3, 4, 5, or 6 amino acid substitutions, insertions and/or deletions in the framework regions, as defined by the IMGT system, relative to SEQ ID NO: 2. In some embodiments, the VH domain comprises the amino acid sequence set forth in SEQ ID NO: 33. In some embodiments, the VH domain comprises the amino acid sequence set forth in SEQ ID NO: 34. In some embodiments, the VH domain comprises the amino acid sequence set forth in SEQ ID NO: 2.

In certain embodiments the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 3; wherein the $V_H$ domain comprises three CDRs of the amino acid sequence set forth in SEQ ID NO: 17, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_L$ domain is humanized and comprises the amino acid sequence set forth in SEQ ID NO: 35; wherein the $V_H$ domain comprises three CDRs of the amino acid sequence set forth in SEQ ID NO: 17, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 2; wherein the $V_L$ domain comprises three CDRs of the amino acid sequence set forth in SEQ ID NO: 18, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 33; wherein the $V_L$ domain comprises three CDRs of the amino acid sequence set forth in SEQ ID NO: 18, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain comprises the amino acid sequence set forth in SEQ ID NO: 34; wherein the $V_L$ domain comprises three CDRs of the amino acid sequence set forth in SEQ ID NO: 18, wherein the antibody or antigen-binding fragment binds DNA and penetrates cells.

In certain embodiments the antibodies or antigen-binding fragments of the disclosure comprise a light chain variable ($V_L$) domain and a heavy chain variable ($V_H$) domain; wherein the $V_H$ domain is humanized and comprises the amino acid sequence set forth in SEQ ID NO: 2; wherein the $V_L$ domain comprises three CDRs of the amino acid sequence set forth in SEQ ID NO: 3, wherein the antibody or antigen-binding fragment binds DNA and penetrates cells.

In certain embodiments, the $V_H$ domain of the antibodies or antigen-binding fragments described herein comprise:
a VH CDR1 having the amino acid sequence of SEQ ID NO: 27;
a VH CDR2 having the amino acid sequence of SEQ ID NO: 28; and
a VH CDR3 having the amino acid sequence of SEQ ID NO: 29.

In certain embodiments, the $V_L$ domain of the antibodies or antigen-binding fragments described herein comprise:
a VL CDR1 having the amino acid sequence of SEQ ID NO: 30;
a VL CDR2 having the amino acid sequence of SEQ ID NO: 31; and
a VL CDR3 having the amino acid sequence of SEQ ID NO: 32.

In some embodiments, the antibodies or antigen-binding fragments disclosed herein comprise a light chain variable ($V_L$) domain and a heavy chain variable ($V_H$) domain; wherein the $V_L$ domain comprises the amino acid sequence set forth in SEQ ID NO: 3; wherein the $V_H$ domain comprises three CDRs of the amino acid sequence set forth in SEQ ID NO: 17, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_L$ domain comprises the amino acid sequence set forth in SEQ ID NO: 35; wherein the $V_H$ domain comprises three CDRs of the amino acid sequence set forth in SEQ ID NO: 17, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 2; wherein the $V_L$ domain comprises three CDRs of the amino acid sequence set forth in SEQ ID NO: 18, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain; wherein the $V_H$ domain comprises the amino acid sequence set forth in SEQ ID NO: 33; wherein the $V_L$ domain comprises three CDRs of the amino acid sequence set forth in SEQ ID NO: 18, wherein the antibody or antigen-binding fragment binds DNA and penetrates cells. In some embodiments, the antibodies or antigen-binding fragments disclosed herein comprise a light chain variable ($V_L$) domain and a heavy chain variable ($V_H$) domain;

wherein the $V_H$ domain comprises the amino acid sequence set forth in SEQ ID NO: 34; wherein the $V_L$ domain comprises three CDRs of the amino acid sequence set forth in SEQ ID NO: 18, wherein the antibody or antigen-binding fragment binds DNA and penetrates cells.

In some embodiments, an antibody or antigen-binding fragment of the disclosure comprises: a) a humanized $V_H$ domain that comprises the amino acid sequence of SEQ ID NO: 2, and b) a $V_L$ domain that comprises the amino acid sequence of SEQ ID NO: 18. In some embodiments, an antibody or antigen-binding fragment of the disclosure comprises: a) a humanized $V_H$ domain that comprises the amino acid sequence of SEQ ID NO: 2, and b) a humanized $V_L$ domain that comprises the amino acid sequence of SEQ ID NO: 3. In some embodiments, an antibody or antigen-binding fragment of the disclosure comprises: a) a humanized $V_H$ domain that comprises the amino acid sequence of SEQ ID NO: 2, and b) a humanized $V_L$ domain that comprises the amino acid sequence of SEQ ID NO: 35. In some embodiments, an antibody or antigen-binding fragment of the disclosure comprises: a) a humanized $V_H$ domain that comprises the amino acid sequence of SEQ ID NO: 33, and b) a $V_L$ domain that comprises the amino acid sequence of SEQ ID NO: 18. In some embodiments, an antibody or antigen-binding fragment of the disclosure comprises: a) a humanized $V_H$ domain that comprises the amino acid sequence of SEQ ID NO: 33, and b) a humanized $V_L$ domain that comprises the amino acid sequence of SEQ ID NO: 3. In some embodiments, an antibody or antigen-binding fragment of the disclosure comprises: a) a humanized $V_H$ domain that comprises the amino acid sequence of SEQ ID NO: 33, and b) a humanized $V_L$ domain that comprises the amino acid sequence of SEQ ID NO: 35. In some embodiments, an antibody or antigen-binding fragment of the disclosure comprises: a) a humanized $V_H$ domain that comprises the amino acid sequence of SEQ ID NO: 34, and b) a $V_L$ domain that comprises the amino acid sequence of SEQ ID NO: 18. In some embodiments, an antibody or antigen-binding fragment of the disclosure comprises: a) a humanized $V_H$ domain that comprises the amino acid sequence of SEQ ID NO: 34, and b) a humanized $V_L$ domain that comprises the amino acid sequence of SEQ ID NO: 3. In some embodiments, an antibody or antigen-binding fragment of the disclosure comprises: a) a humanized $V_H$ domain that comprises the amino acid sequence of SEQ ID NO: 34, and b) a humanized $V_L$ domain that comprises the amino acid sequence of SEQ ID NO: 35. In some embodiments, an antibody or antigen-binding fragment of the disclosure comprises: a) a $V_H$ domain that comprises the amino acid sequence of SEQ ID NO: 17, and b) a humanized $V_L$ domain that comprises the amino acid sequence of SEQ ID NO: 3. In some embodiments, an antibody or antigen-binding fragment of the disclosure comprises: a) a $V_H$ domain that comprises the amino acid sequence of SEQ ID NO: 17, and b) a humanized $V_L$ domain that comprises the amino acid sequence of SEQ ID NO: 35.

In some embodiments, an antibody or antigen-binding fragment of the disclosure includes a signal sequence. In some embodiments, the signal sequence is conjugated to the N-terminal portion of any of the $V_L$ sequences disclosed herein (e.g., SEQ ID NO: 3). In some embodiments, the signal sequence conjugated to the light chain is SEQ ID NO: 5. In some embodiments, the signal sequence is conjugated to the N-terminal portion of any of the $V_H$ sequences disclosed herein (e.g., SEQ ID NO: 2). In some embodiments, the signal sequence conjugated to the heavy chain is SEQ ID NO: 4. It is understood that, when a signal sequence is included for expression of an antibody or antibody fragment, that signal sequence is generally cleaved and not present in the finished polypeptide (e.g., the signal sequence is generally cleaved and present only transiently during protein production).

In some embodiments, the $V_H$ domain of any of the antibodies or antigen-binding fragments of the disclosure described herein comprise one or more of the following amino acid alterations: V5Q, E6Q, L11V, V12I, K13Q, R18L, K19R, V37I, E42G, A49S, T63S, A75S, F80Y, T84N, S88A, M93V, T111L or L112V, as compared with an numbered with reference to the amino acid sequence of SEQ ID NO: 17. In other words, in certain embodiments, an antibody or antigen-binding fragment comprises one or more amino acid alteration at a position corresponding to the foregoing, where the corresponding position is compared with SEQ ID NO: 17. In certain embodiments, the $V_H$ domain comprises one or more of the following amino acid alterations: V5Q, L11V, K13Q, R18L, K19R, V37I, E42G, A49S, T63S, A75S, F80Y, T84N, M93V, T111L or L112V, as compared with and numbered with reference to the amino acid sequence of SEQ ID NO: 17. In certain embodiments, the $V_H$ domain comprises at least 5, at least 6, at least 7, at least 8, at least 9, at least 10, at least 11, at least 12, at least 13, at least 14, at least 15, at least 16, or at least 17 of said alterations, as compared with and numbered with reference to the amino acid sequence of SEQ ID NO: 17. In certain embodiments, at least one of the alterations in the $V_H$ domain is a V5Q alteration, as compared with and numbered with reference to the amino acid sequence of SEQ ID NO: 17. In certain embodiments, at least one of the alterations in the $V_H$ domain is a E6Q alteration, as compared with and numbered with reference to the amino acid sequence of SEQ ID NO: 17. In certain embodiments, at least one of the alterations in the $V_H$ domain is a L11V alteration, as compared with and numbered with reference to the amino acid sequence of SEQ ID NO: 17. In certain embodiments, at least one of the alterations in the $V_H$ domain is a V37I alteration, as compared with and numbered with reference to the amino acid sequence of SEQ ID NO: 17. In certain embodiments, the $V_H$ domain retains a serine at the amino acid position corresponding to amino acid position 88 of SEQ ID NO: 17. In certain embodiments, the $V_H$ domain retains a valine at the amino acid position corresponding to amino acid position 12 of SEQ ID NO: 17. In certain embodiments, the $V_H$ domain retains a tryptophan at the amino acid position corresponding to amino acid position 47 of SEQ ID NO: 17. All operable combinations of the foregoing are contemplated, as are combinations with any of the aspect and embodiments provided herein for the VL. The foregoing numbering of amino acid residues is with reference to linear amino acid sequence of a given VH and the disclosure contemplates humanized antibodies and antigen binding fragments having one or more of the recited substitutions at a position corresponding to the recited position in the murine, parent VH or VL.

In certain embodiments of any of the foregoing, or of any of the aspects and embodiments disclosed herein, the $V_L$ domain of any of the humanized antibodies or antigen-binding fragments described herein comprise one or more of the following amino acid alterations: V3Q, L4M, A9S, A12S, V13A, L15V, Q17D, A19V, S22T, M37L, H38A, G45E, Q46K, P47A, E59Q, A64S, H76T, N78T, H80S, P81S, V82L, E83Q, E84P, A87V, A87F, or G104A, as compared with and numbered with reference to the amino acid sequence of SEQ ID NO: 18. In certain embodiments, the $V_L$ domain comprises one or more of the following amino acid alterations: V3Q, L4M, A9S, A12S, V13A, L15V, Q17D, A19V, G45E, Q46K, P47A, E59Q, A64S, H76T, N78T, H80S, P81S, V82L, E83Q, E84P, A87V, or G104A, as compared with and numbered with reference to the amino acid sequence of SEQ ID NO: 18. In certain embodiments, the $V_L$ domain comprises at least 5, at least 6, at least 7, at least 8, at least 9, at least 10, at least 11, at least 12, at least 13, at least 14, at least 15, at least 16, at least 17, at least 18, at least 19, at least 20, at least 21, or at least 22 of said amino acid alterations, as compared with and numbered with reference to the amino acid sequence of SEQ ID NO: 18.

It should be understood that any of the foregoing variations at particular positions are referred to relative to the amino acid sequence set forth in SEQ ID NO: 18 or 17. An antibody or antigen binding fragment of the disclosure may comprise one or more of such amino acid alterations at the corresponding position, relative to the amino acid sequence of SEQ ID NO: 18 or 17. By way of example, in certain embodiments, the VH domain comprises an L to V alteration at a position corresponding to position 11 of SEQ ID NO: 17 (e.g., an L11V alteration). This is exemplary of how all of the foregoing alterations can also be described, and such description is expressly contemplated. By way of another example, in certain embodiments, the VL domain comprises a V to Q alteration at a position corresponding to position 3 of SEQ ID NO: 18 (e.g., a V3Q alteration).

In certain embodiments, the $V_L$ domain comprises a serine at each of the amino acid positions corresponding to amino acid positions 80 and 81 of SEQ ID NO: 18. In certain embodiments, the $V_L$ domain retains a lysine at the amino acid position corresponding to amino acid position 53 of SEQ ID NO: 18. In certain embodiments, the $V_L$ domain does not have any one or more of the following amino acid combinations:

a) asparagine and serine at the amino acid positions corresponding to amino acid positions 80 and 81 of SEQ ID NO: 18, respectively; or b) asparagine and glycine at the amino acid positions corresponding to amino acid positions 80 and 81 of SEQ ID NO: 18, respectively; or c) asparagine and proline at the amino acid positions corresponding to amino acid positions 80 and 81 of SEQ ID NO: 18, respectively. All operable combinations of the foregoing are contemplated, as are combinations with any of the aspect and embodiments provided herein for the VH. The foregoing numbering of amino acid residues is with reference to linear amino acid sequence of a given VH and the disclosure contemplates humanized antibodies and antigen binding fragments having one or more of the recited substitutions at a position corresponding to the recited position in the murine, parent VH or VL.

In some embodiments, the humanized internalizing moiety (e.g., a humanized antibody or antigen-binding fragment comprising a light chain variable ($V_L$) domain comprising the amino acid sequence set forth in SEQ ID NO: 3 and a heavy chain variable ($V_H$) domain comprising the amino acid sequence set forth in SEQ ID NO: 2) is associated with at least one superior physiological or biological property as compared to a reference non-humanized internalizing moiety (e.g., the murine, parent 3E10 antibody). In other embodiments, the humanized internalizing moiety is associated with at least two superior physiological or biological properties as compared to a reference non-humanized internalizing moiety. In other embodiments, the humanized internalizing moiety is associated with at least three superior physiological or biological properties as compared to a reference non-humanized internalizing moiety (e.g., the murine, parent 3E10 antibody). In some embodiments, the reference non-humanized internalizing moiety comprises the murine parent antibody comprising a VH comprising the amino acid sequence of SEQ ID NO: 17 and a VL comprising the amino acid sequence of SEQ ID NO: 18. In some embodiments, the reference humanized internalizing moiety is an antibody comprising the amino acid sequence of SEQ ID NO: 42. In some embodiments, the reference internalizing moiety is a humanized antibody or antigen binding fragment comprising the $V_H$ amino acid sequence of SEQ ID NO: 41 and the $V_L$ amino acid sequence of SEQ ID NO: 40.

In certain embodiments, the antibodies or antigen-binding fragments described herein are humanized and are associated with at least one superior biological or physiological property as compared to a murine antibody, which murine antibody comprises a $V_L$ domain comprising the amino acid sequence set forth in SEQ ID NO: 18 and a $V_H$ domain comprising the amino acid sequence set forth in SEQ ID NO: 17, and/or as compared to an alternative antibody or antigen-binding fragment thereof, wherein said alternative antibody or antigen-binding fragment comprises a $V_L$ domain comprising the CDRs of the amino acid sequence set forth in SEQ ID NO: 18 and a $V_H$ domain comprising the CDRs of the amino acid sequence set forth in SEQ ID NO: 17; and wherein said alternative antibody or fragment does not comprise a $V_L$ domain comprising the amino acid sequence of SEQ ID NO: 3 or 35, and/or wherein said alternative antibody or fragment does not comprise a $V_H$ domain comprising the amino acid sequence of any of SEQ ID NOs: 2, 33 or 34; or, in some embodiments, wherein said alternative antibody or fragment does not comprise a $V_L$ domain comprising the amino acid sequence of SEQ ID NO: 3, and/or wherein said alternative antibody or fragment does not comprise a $V_H$ domain comprising the amino acid sequence of any of SEQ ID NOs: 2.

In some embodiments, a humanized internalizing moiety of the disclosure (e.g., a humanized antibody or antigen-binding fragment thereof comprises a light chain variable ($V_L$) domain comprising the amino acid sequence set forth in SEQ ID NO: 3 and a heavy chain variable ($V_H$) domain comprising the amino acid sequence set forth in SEQ ID NO: 2) is associated with at least one superior physiological or biological property as compared to an alternative internalizing moiety or fragment thereof (e.g., a different humanized antibody based on the same parent, murine antibody and, optionally, having the same CDRs). In other embodiments, a humanized internalizing moiety of the disclosure is associated with at least two superior physiological or biological properties as compared to the alternative internalizing moiety (e.g., a different humanized antibody based on the same parent, murine antibody and, optionally, having the same CDRs). In other embodiments, the humanized internalizing moiety of the disclosure is associated with at least three superior physiological or biological properties as compared to the alternative internalizing moiety (e.g., a different humanized antibody based on the same parent, murine antibody and, optionally, having the same CDRs). In some embodiments, the alternative antibody is the parent antibody from which the humanized antibody was derived (e.g., the parent, murine antibody). In some embodiments, the alternative antibody is another humanized antibody that is derived from the 3E10 antibody but that has a different amino acid sequence than the humanized internalizing moieties or antigen-binding fragments thereof of the present disclosure. In some embodiments, an antibody or antigen binding fragment of the disclosure has one or more improved characteristics in comparison to the murine parent antibody and/or an alternative humanized antibody. In some embodiments, the alternative humanized antibody has one, two, or three amino acid substitutions in the Kabat CDRs, as compared to an antibody of the disclosure. In some embodiments, the alternative internalizing moiety or fragment thereof comprises:

a VH CDR1 having the amino acid sequence of SEQ ID NO: 19;

a VH CDR2 having the amino acid sequence of SEQ ID NO: 20;

a VH CDR3 having the amino acid sequence of SEQ ID NO: 21;

a VL CDR1 having the amino acid sequence of SEQ ID NO: 22;

a VL CDR2 having the amino acid sequence of SEQ ID NO: 23; and a VL CDR3 having the amino acid sequence of SEQ ID NO: 24, which CDRs are defined in accordance with Kabat, but does not comprise the same scaffold amino acid sequence present in the humanized internalizing moieties or fragments thereof of the present disclosure (e.g. a humanized internalizing moiety or fragment thereof comprising the amino acid sequence of any of SEQ ID NOs: 2, 3 or 38-40).

In some embodiments, the superior biological or physiological property associated with the humanized internalizing moieties or fragments of the disclosure described herein is that the humanized internalizing moiety or antigen-binding fragment is associated with reduced immunogenicity in a human patient as compared to the immunogenicity of the non-humanized or to the alternative antibody or antigen-binding fragment in a human patient. The skilled worker is familiar with numerous assays for determining the immunogenicity of the antibodies. In preferred embodiments, the humanized antibodies of the disclosure are associated with reduced immunogenicity in a human patient, but retain the cell penetration properties associated with the murine 3E10 antibody.

In some embodiments, the superior biological or physiological property associated with the humanized internalizing moieties or fragments of the disclosure described herein is that the humanized internalizing moiety or antigen-binding fragment is associated with increased solubility in a physiologically acceptable carrier as compared to the solubility of the non-humanized or to the alternative antibody or antigen-binding fragment in the same type of physiologically acceptable carrier. As used herein, a physiologically acceptable carrier includes include water, ethanol, polyols (such as glycerol, propylene glycol, polyethylene glycol, and the like), and suitable mixtures thereof, vegetable oils, such as olive oil, and injectable organic esters, such as ethyl oleate. In some embodiments, the humanized internalizing moiety or fragment is associated with at least 5%, 10%, 25%, 50%, 75%, 100%, 150%, 200% or 300% greater solubility in a physiologically acceptable carrier as compared to a non-humanized or alternative internalizing moiety or antigen-binding fragment in the same type of physiologically acceptable carrier. The skilled worker is aware of routine experiments that may be utilized for testing the solubility of the humanized internalizing moieties or fragments thereof. Examples of solubility assays include standard turbidity or light-scattering assays, commercial solubility assays, such as the OptiSol™ solubility assay kit (DiLyx, Seattle, Wash.), or the protein solubility assay screen described in Bondos et al., 2003, Analytical Biochemistry, 316:223-231 may be utilized.

In some embodiments, the superior biological or physiological property associated with the humanized internalizing moieties or fragments of the disclosure described herein is that the humanized internalizing moiety or antigen-binding fragment is associated with a higher expression level in a type of cell as compared to the expression level of the non-humanized or alternative antibody or antigen-binding fragment in the same type of cell. In some embodiments, the humanized internalizing moiety or fragment is associated with at least 5%, 10%, 25%, 50%, 75%, 100%, 150%, 200% or 300% higher expression level in a cell as compared to the expression level of a non-humanized or alternative internalizing moiety or antigen-binding fragment in the same type of cell. The skilled worker is aware of routine experiments that may be utilized for testing the expression level of the humanized internalizing moieties or fragments thereof.

In some embodiments, the superior biological or physiological property associated with the humanized internalizing moieties or fragments of the disclosure described herein is that the humanized internalizing moiety or antigen-binding fragment is associated with lower toxicity (e.g., cytotoxicity and/or genotoxicity) in a cell type as compared to the toxicity in the same type of cell that is associated with the non-humanized or alternative antibody or antigen-binding fragment. In some embodiments, the humanized internalizing moiety or fragment is associated with at least 5%, 10%, 25%, 50%, 75%, 100%, 150%, 200% or 300% lower toxicity as compared to the toxicity of a non-humanized or alternative internalizing moiety or antigen-binding fragment in the same type of cell. In some embodiments the cell is a mammalian cell. In some embodiments the cell is a human cell. In some embodiments, the cell is in an organism, such as a mammal. In some embodiments, the cell is a human cell in a human organism. The skilled worker is aware of routine experiments that may be utilized for testing the toxicity of the humanized internalizing moieties or fragments thereof. For example, the toxicity of the humanized internalizing moieties or fragments of the disclosure and of the non-humanized or alternative internalizing moieties or fragments thereof may be tested in an in vitro cell or cell culture, such as in a cell or cell culture derived from human cells, or may be tested in an in vitro animal model such as a mouse or rat.

In some embodiments, the superior biological or physiological property associated with the humanized internalizing moieties or fragments of the disclosure described herein is that the humanized internalizing moiety or antigen-binding fragment is associated with reduced aggregation in a physiologically acceptable carrier as compared to aggregation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less aggregation in a physiologically acceptable carrier as compared to a non-humanized or alternative internalizing moiety or antigen-binding fragment in the same type of physiologically acceptable carrier. In some embodiments, the humanized antibody or antigen-binding antigen-binding fragment in a pharmaceutically acceptable carrier is associated with reduced aggregation after a period of at least 1 hour, 6 hours, 12 hours, 18 hours, 24 hours, 36 hours, 2 days, 5 days, one week, two weeks, four weeks, one month, two months, three months, six months or one year. The skilled worker is aware of routine experiments that may be utilized for testing the aggregation of the humanized internalizing moieties or fragments thereof. Examples of aggregation assays include standard turbidity or light-scattering assays (e.g., A600 nm assay), visual inspection, SDS-PAGE, commercial aggregation assays, such as the OptiSol™ aggregation assay kit (DiLyx, Seattle, Wash.), HP-SEC analysis, or the protein aggregation assay screen described in Bondos et al., 2003, Analytical Biochemistry, 316:223-231 may be utilized.

In some embodiments, the superior biological or physiological property associated with the humanized internalizing moieties or antigen-binding fragments of the disclosure described herein is that the humanized internalizing moiety or antigen-binding fragment is associated with increased stability in a physiologically acceptable carrier as compared to the stability of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% greater stability in a physiologically acceptable carrier as compared to a non-humanized or alternative internalizing moiety or antigen-binding fragment in the same type of physiologically acceptable carrier. In some embodiments, the humanized antibody or antigen-binding antigen-binding fragment in a pharmaceutically acceptable carrier is associated with increased stability after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the stability of the humanized internalizing moieties or fragments thereof. For example, the skilled worker could test the stability of the humanized and non-humanized or alternative internalizing moieties or fragments thereof after various intervals of being stored in a physiologically acceptable carrier. Commercial assays such as the ProteoStat™ Thermal shift stability assay (Enzo, Farmingdale, N.Y.) may be utilized in assessing the stability of the moieties or fragments thereof. Alternatively, the stability of the moieties or fragments thereof may be determined by HP-SEC or by SDS-PAGE analysis.

In some embodiments, the superior biological or physiological property associated with the humanized internalizing moieties or antigen-binding fragments of the disclosure described herein is that the humanized internalizing moiety or antigen-binding fragment is associated with improved cell penetration as compared to the cell penetration of the non-humanized or alternative antibody or antigen-binding fragment. In some embodiments, the improved penetration is due to the increased efficiency of the humanized internalizing moiety or antigen-binding fragment to be internalized by an ENT transporter (e.g., an ENT2 and/or ENT3 transporter). In some embodiments, the humanized internalizing moiety or fragment is associated with at least 5%, 10%, 25%, 50%, 75%, 100%, 150%, 200% or 300% greater cell penetration as compared to a non-humanized or alternative internalizing moiety or antigen-binding fragment in the same type of physiologically acceptable carrier. The skilled worker is aware of routine experiments that may be utilized for testing the cell penetration of the humanized internalizing moieties or fragments thereof. For example, the humanized internalizing moieties or fragments thereof may be labeled (e.g. fluorescently or radiolabeled) and administered to a cell or cell culture in order to determine the cell penetration of the humanized internalizing moieties or fragments thereof. Alternatively, the humanized internalizing moieties or fragments may be administered to a cell or cell culture and then detected with a secondary agent, e.g., a fluorescently labeled or radiolabeled secondary antibody, in order to determine the cell penetration of the humanized internalizing moieties or fragments thereof.

In some embodiments, the superior biological or physiological property associated with the humanized internalizing moieties or fragments of the disclosure described herein is that the humanized internalizing moiety or antigen-binding fragment is associated with reduced glycosylation in a cell type as compared to the glycosylation of the non-humanized or alternative antibody or antigen-binding fragment in the same cell type. In some embodiments, an asparagine is mutated to another amino acid residue in the VH or VL domains in order to reduce N-linked glycosylation of the humanized antibody or antibody fragment. In other embodiments, the superior biological or physiological property associated with the humanized internalizing moieties or fragments described herein is that the humanized internalizing moiety or antigen-binding fragment is associated with increased glycosylation in a cell type as compared to the glycosylation of the non-humanized or alternative antibody or antigen-binding fragment in the same cell type. In some embodiments, the superior biological or physiological property associated with the humanized internalizing moieties or fragments described herein is that the humanized internalizing moiety or antigen-binding fragment is associated with a specific pattern of glycosylation in a cell type that differs from the glycosylation pattern of the non-humanized or alternative internalizing moiety or antigen-binding fragment in the same type of cell. For example, the humanized internalizing moiety or antigen-binding fragment may be hemi-glycosylated in a cell type while the non-humanized or alternative internalizing moiety or antigen-binding fragment is not hemi-glycosylated in the same type of cell. In some embodiments, the superior biological or physiological property associated with the humanized internalizing moieties or fragments described herein is that the humanized internalizing moiety or antigen-binding fragment is post-translationally modified with a specific glycosylation group in a cell type that differs from the post-translational modification of the non-humanized or alternative internalizing moiety or antigen-binding fragment in the same type of cell. The skilled worker is aware of routine experiments that may be utilized for testing the glycosylation patterns of the humanized internalizing moieties or fragments thereof. Examples of experiments for testing the glycosylation levels and patterns of the internalizing moieties and fragments thereof include protocols described in Mohammad, 2002, Protein Protocols Handbook, pages 795-802; standard procedures involving mass spectrometry and/or HPLC; GLYCO-PRO™ (Sigma-Aldrich); and Qproteome Total Glycoprotein Kit™ (Qiagen, Valencia, Calif.). In order to identify the exact sites of glycosylation in a protein sequence, standard endoproteinase cleavage may be performed (e.g. tryptic digest) followed by analysis by LC/MS or HILIC-MS/MS, similar to the protocols described in Zauner G et al., 2010, J Sep Sci., 33:903-10.

In some embodiments, the superior biological or physiological property associated with the humanized internalizing moieties or fragments of the disclosure described herein is that the humanized internalizing moiety or antigen-binding fragment is associated with reduced deamidation in a physiologically acceptable carrier as compared to deamidation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less deamidation in a physiologically acceptable carrier as compared to a non-humanized or alternative internalizing moiety or antigen-binding fragment in the same type of physiologically acceptable carrier. In some embodiments, the humanized antibody or antigen-binding fragment in a pharmaceutically acceptable carrier is associated with reduced deamidation after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the deamidation of the humanized internalizing moieties or fragments thereof. Examples of assays for testing protein deamidation include commercially available deamidation assays such as the ISOQUANT® Isoaspartate Detection Kit (Promega, Madison Wis.) or Dionex UltiMate 3000 Titanium System (Dionex, Sunnyvale, Calif.). Other assays may include peptide mapping. See generally, Kalgahtgi, K., & Horvath, C. "Rapid Peptide Mapping by High Performance Liquid Chromatography", J. Chromatography 443, 343-354 (1988).

In some embodiments, the superior biological or physiological property associated with the humanized internalizing moieties or fragments of the disclosure described herein is that the humanized internalizing moiety or antigen-binding fragment is associated with reduced oxidation in a physiologically acceptable carrier as compared to oxidation of the non-humanized or alternative antibody or antigen-binding fragment in the same type of physiologically acceptable carrier. In some embodiments, the humanized internalizing moiety or fragment is associated with at least 5%, 10%, 25%, 50%, 75%, 100%, 150%, 200% or 300% less oxidation in a physiologically acceptable carrier as compared to a non-humanized or alternative internalizing moiety or antigen-binding fragment in the same type of physiologically acceptable carrier. In some embodiments, the humanized antibody or antigen-binding antigen-binding fragment in a pharmaceutically acceptable carrier is associated with reduced oxidation after a period of at least 1 hour, 6 hours, 12 hours, 18 hours, 24 hours, 36 hours, 2 days, 5 days, one week, two weeks, four weeks, one month, two months, three months, six months or one year as compared to a non-humanized or alternative internalizing moiety or antigen-binding fragment in the same type of physiologically acceptable carrier. The skilled worker is aware of routine experiments that may be utilized for testing the oxidation of the humanized internalizing moieties or fragments thereof. For example, oxidation levels may be assessed by using any one of several commercially available oxidation assays, such as the Methionine Sulfoxide Immunoblotting Kit (Cayman Chemical, Ann Arbor, Mich.). Other assays may include peptide mapping. See generally, Kalgahtgi, K., & Horvath, C. "Rapid Peptide Mapping by High Performance Liquid Chromatography", J. Chromatography 443, 343-354 (1988).

In some embodiments, the superior biological or physiological property associated with the humanized internalizing moieties or fragments of the disclosure described herein is that the humanized internalizing moiety or antigen-binding fragment is associated with reduced lipidation when produced in a cell type as compared to the lipidation of the non-humanized or alternative antibody or fragment when produced in the same type of cell. In other embodiments, the superior biological or physiological property associated with the humanized internalizing moieties or fragments described herein is that the humanized internalizing moiety or antigen-binding fragment is associated with increased lipidation when produced in a cell type as compared to the lipidation of the non-humanized or alternative antibody or antigen-binding fragment when produced in the same type of cell. In some embodiments, the superior biological or physiological property associated with the humanized internalizing moieties or fragments described herein is that the humanized internalizing moiety or antigen-binding fragment is associated with a specific pattern of lipidation when produced in a cell type that differs from the lipidation pattern of the non-humanized or alternative internalizing moiety or antigen-binding fragment when produced in the same type of cell. In some embodiments, the superior biological or physiological property associated with the humanized internalizing moieties or fragments described herein is that the humanized internalizing moiety or antigen-binding fragment is post-translationally modified with a specific lipidation group when produced in a cell type that differs from the post-translational modification of the non-humanized or alternative internalizing moiety or antigen-binding fragment when produced in the same type of cell. The skilled worker is aware of routine experiments that may be utilized for testing the lipidation patterns of the humanized internalizing moieties or fragments thereof. For example, the internalizing moieties or fragments thereof may be assessed by the protocols described in Gelb et al., 1999, Protein Lipidation Protocols, Humana Press, pages 1-256.

In some embodiments, the superior biological or physiological property associated with the humanized internalizing moieties or fragments of the disclosure described herein is that the humanized internalizing moiety or antigen-binding fragment is capable of binding a polynucleotide (e.g., DNA) with higher affinity (lower $K_D$) as compared to the binding affinity of the non-humanized, parent antibody or an alternative antibody or fragment, such as a different humanized antibody. In some embodiments, the humanized internalizing moiety or fragment is associated with at least 5%, 10%, 25%, 50%, 75%, 100%, 150%, 200% or 300% stronger binding affinity for a polynucleotide (e.g., DNA; double stranded blunt DNA) as compared to a non-humanized or alternative internalizing moiety or antigen-binding fragment in the same type of physiologically acceptable carrier. The skilled worker is aware of routine experiments that may be utilized for testing the binding affinity ($K_D$) of the humanized internalizing moieties or fragments thereof. Binding affinity can be measured using Surface Plasmon Resonance (SPR) or Quartz Crystal Microbalance (QCM), in accordance with currently standard methods and the manufacturer's protocols.

III. Chimeric Polypeptides

The disclosure provides chimeric polypeptides comprising an internalizing moiety portion and a non-internalizing moiety portion. As detailed above, the non-internalizing moiety polypeptide portion comprises or consists of a alpha-amylase polypeptide (e.g., a mature alpha-amylase). Numerous examples of internalizing moieties, and each of the potential non-internalizing moiety polypeptide portions are described above, and all suitable combinations of internalizing moiety portions and non-internalizing moiety polypeptide portions to generate chimeric polypeptides are contemplated.

Without being bound by theory, the association of the alpha-amylase polypeptide (e.g., a mature alpha-amylase polypeptide) with the internalizing moiety portion facilitates delivery of the chimeric polypeptide, and thus, the non-internalizing moiety portion to the cytoplasm and, optionally, to the lysosome and/or autophagic vesicles. In certain embodiments, the internalizing moiety delivers alpha-amylase activity into cells. In certain embodiments, the chimeric polypeptide of the disclosure comprises an alpha-amylase-containing chimeric polypeptide (e.g., the non-internalizing moiety portion comprises or consists of an alpha-amylase polypeptide). Any of the internalizing moieties described herein may be combined with any of the non-internalizing moiety polypeptide portions, as described herein, to generate a chimeric polypeptide of the disclosure.

The disclosure provides chimeric polypeptides (e.g., chimeric polypeptides of the disclosure). Chimeric polypeptides for use in the methods disclosed herein can be made in various manners. The chimeric polypeptides may comprise any of the internalizing moiety portions and the alpha-amylase polypeptide portions disclosed herein. As used herein, chimeric polypeptides of the disclosure comprise (i) an alpha-amylase polypeptide portion and (ii) an internalizing moiety portion. In addition, any of the chimeric polypeptides disclosed herein may be utilized in any of the methods or compositions disclosed herein. In some embodiments, an internalizing moiety (e.g. an antibody or antigen-binding fragment) is linked, directly or indirectly, to any of the alpha-amylase polypeptides and/or fragments and/or variants disclosed herein.

In some embodiments, the alpha-amylase polypeptide is a mature alpha-amylase and comprises the amino acid sequence of SEQ ID NO: 1, or variants or fragments thereof, fused to the C-terminus of an internalizing moiety. In some embodiments, the alpha-amylase polypeptide comprises the amino acid sequence of SEQ ID NO: 1, or variants or fragments thereof, fused to the C-terminus of the heavy chain segment of a Fab internalizing moiety. In some embodiments, the alpha-amylase polypeptide comprises the amino acid sequence of SEQ ID NO: 1, or variants or fragments thereof, fused to the C-terminus of the heavy chain segment of a full-length antibody internalizing moiety.

In some embodiments, the chimeric polypeptide comprises: (i) an alpha-amylase polypeptide, and (ii) an internalizing moiety; wherein the alpha-amylase polypeptide comprises an amino acid sequence that is at least 85%, 90%, 91%, 92%, 93%, 94%, 95%, 96%, 97%, 98%, 99% or 100% identical to the amino acid sequence of SEQ ID NO: 1; and wherein the internalizing moiety is an antibody or antigen binding fragment, wherein the antibody or antigen binding fragment comprises a heavy chain variable domain and a light chain variable domain; wherein the heavy chain variable domain comprises an amino acid sequence that is at least 85%, 90%, 91%, 92%, 93%, 94%, 95%, 96%, 97%, 98%, 99% or 100% identical to the amino acid sequence of SEQ ID NO: 2; and wherein the light chain variable domain comprises an amino acid sequence that is at least 85%, 90%, 91%, 92%, 93%, 94%, 95%, 96%, 97%, 98%, 99% or 100% identical to the amino acid sequence of SEQ ID NO: 3. In some embodiments, the chimeric polypeptide comprises: (i) an alpha-amylase polypeptide, and (ii) an internalizing moiety; wherein the alpha-amylase polypeptide comprises the amino acid sequence of SEQ ID NO: 1; and wherein the internalizing moiety is an antibody or antigen binding fragment, wherein the antibody or antigen binding fragment comprises a heavy chain variable domain and a light chain variable domain; wherein the heavy chain variable domain comprises the amino acid sequence of SEQ ID NO: 2; and wherein the light chain variable domain comprises the amino acid sequence of SEQ ID NO: 3. In some embodiments, the heavy chain comprises the leader sequence of SEQ ID NO: 4. In some embodiments, the light chain comprises the leader sequence of SEQ ID NO: 5. In some embodiments, the disclosure provides a chimeric polypeptide that does not include a leader sequence, for example, the leader sequence has been proceesed. In some embodiments, the chimeric polypeptide comprises a linker interconnecting the alpha-amylase polypeptide to the internalizing moiety. In some embodiments, the linker comprises the amino acid sequence of SEQ ID NO: 6. In some embodiments, the chimeric polypeptide comprises a heavy chain amino acid sequence lacking a leader sequence (e.g., lacking the leader sequence of SEQ ID NO: 4). In some embodiments, the chimeric polypeptide comprises the amino acid sequence of SEQ ID NO: 7. In some embodiments, the chimeric polypeptide comprises a light chain amino acid sequence lacking a leader sequence (e.g., lacking the leader sequence of SEQ ID NO: 5). In some embodiments, the chimeric polypeptide comprises the amino acid sequence of SEQ ID NO: 8. In some embodiments, the chimeric polypeptide comprises the amino acid sequence of both SEQ ID NOs: 7 and 8.

In some embodiments, the chimeric polypeptide comprises an amino acid sequence that is at least 85%, 90%, 91%, 92%, 93%, 94%, 95%, 96%, 97%, 98%, 99% or 100% identical to the amino acid sequence of SEQ ID NO: 9. In some embodiments, the chimeric polypeptide comprises an amino acid sequence that is at least 85%, 90%, 91%, 92%, 93%, 94%, 95%, 96%, 97%, 98%, 99% or 100% identical to the amino acid sequence of SEQ ID NO: 10. In some embodiments, the chimeric polypeptide comprises the amino acid sequences of both SEQ ID NOs: 9 and 10. In some embodiments, the chimeric polypeptide comprises an amino acid sequence that is at least 85%, 90%, 91%, 92%, 93%, 94%, 95%, 96%, 97%, 98%, 99% or 100% identical to the amino acid sequence of SEQ ID NO: 43. In some embodiments, the chimeric polypeptide comprises an amino acid sequence that is at least 85%, 90%, 91%, 92%, 93%, 94%, 95%, 96%, 97%, 98%, 99% or 100% identical to the amino acid sequence of SEQ ID NO: 8. In some embodiments, the chimeric polypeptide comprises the amino acid sequences of both SEQ ID NOs: 8 and 43.

In some embodiments, a chimeric polypeptide comprising any of the mature alpha-amylase polypeptide or fragments or variants thereof disclosed herein and any of the antibodies or antigen binding fragments disclosed herein (e.g., a protein comprising the amino acid sequences of SEQ ID NOs: 8 and 43), has a higher biological activity (e.g., at least 10%, 20%, 30%, 40%, 50%, 60%, 70%, 80%, 90%, 100%, 150%, or 200% higher biological activity) at a slightly acidic pH (e.g., pH 5.5) as compared to a reference wildtype mature alpha amylase (e.g., an alpha-amylase consisting of the amino acid sequence of SEQ ID NO: 1). In some embodiments, the chimeric polypeptide has a higher biological activity (e.g., at least 10%, 20%, 30%, 40%, 50%, 60%, 70%, 80%, 90%, 100%, 150%, or 200% higher biological activity) at a slightly acidic pH (e.g., pH 5.5) as compared to the biological activity of the same chimeric polypeptide at a neutral pH (e.g., pH 7.0). In some embodiments, the chimeric polypeptide has a higher biological activity (e.g., at least 10%, 20%, 30%, 40%, 50%, 60%, 70%, 80%, 90%, 100%, 150%, or 200% higher biological activity) at a slightly acidic pH (e.g., pH 5.5) as compared to the biological activity of the same chimeric polypeptide at a more acidic pH (e.g., pH 4.3). In some embodiments, the "slightly acidic pH" is selected from the group consisting of ranges 4.5 to 6.5; 4.8 to 6.3; 5.2 to 6.2; 5.3 to 6.3; 5.0 to 6.0; 5.2 to 5.8; 5.3 to 5.7; 5.4 to 5.6; or at 5.5. In some embodiments, the chimeric polypeptide has highest biological activity at a pH range of 4.5 to 6.5; 4.8 to 6.3; 5.2 to 6.2; 5.3 to 6.3; 5.0 to 6.0; 5.2 to 5.8; 5.3 to 5.7; 5.4 to 5.6; or at 5.5. In some embodiments, the biological activity is the ability of the alpha-amylase portion of the chimeric polypeptide to hydrolyze glycogen. In some embodiments, the biological activity may be measured using a glycogen digestion assay, similar to the assay described in the Exemplification section provided herein.

In certain embodiments, potential configurations include the use of truncated portions of an antibody's heavy and light chain sequences (e.g., mAB 3E10) as needed to maintain the functional integrity of the attached alpha-amylase. Further still, the internalizing moiety can be linked to an exposed internal (non-terminus) residue of alpha-amylase or a fragment and/or variant thereof. In some embodiments, any combination of the alpha-amylase-internalizing moiety configurations can be employed, thereby resulting in a alpha-amylase:internalizing moiety ratio that is greater than 1:1 (e.g., two alpha-amylase molecules to one internalizing moiety).

The alpha-amylase polypeptide and the internalizing moiety may be linked directly to each other. Alternatively, they may be linked to each other via a linker sequence, which separates alpha-amylase polypeptide and the internalizing moiety by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional domains of the alpha-amylase polypeptide or the internalizing moiety, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence. In a specific embodiment, a linker sequence length of about 20 amino acids can be used to provide a suitable separation of functional protein domains, although longer or shorter linker sequences may also be used. The length of the linker sequence separating the alpha-amylase polypeptide from the internalizing moiety can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. In other embodiments, the linker joining the alpha-amylase polypeptide to an internalizing moiety can be a constant domain of an antibody (e.g., constant domain of mAb 3E10 or all or a portion of an Fc region of another antibody). In certain embodiments, the linker is a cleavable linker. In certain embodiments, the linker sequence comprises the linker sequence of SEQ ID NO: 6. In certain embodiments, the internalizing moiety is an antibody or antibody fragment and the conjugation includes chemical or recombinant conjugation to a constant domain, such as the constant domain of a heavy chain of the antibody or antibody fragment. In such embodiments, it is appreciated that the alpha-amylase polypeptide and internalizing moiety may be further associated via the association between the heavy chain and light chain of the antibody or antibody fragment. This is also included within the scope of the conjugation.

In other embodiments, the alpha-amylase polypeptide or functional fragment thereof may be conjugated or joined directly to the internalizing moiety. For example, a recombinantly conjugated chimeric polypeptide can be produced as an in-frame fusion of the alpha-amylase portion and the internalizing moiety portion. In certain embodiments, the linker may be a cleavable linker. In any of the foregoing embodiments, the internalizing moiety may be conjugated (directly or via a linker) to the N-terminal or C-terminal amino acid of the alpha-amylase polypeptide. In other embodiments, the internalizing moiety may be conjugated (directly or indirectly) to an internal amino acid of the alpha-amylase polypeptide. Note that the two portions of the construct are conjugated/joined to each other. Unless otherwise specified, describing the chimeric polypeptide as a conjugation of the alpha-amylase portion to the internalizing moiety is used equivalently as a conjugation of the internalizing moiety to the alpha-amylase portion. Further, unless otherwise specified, conjugation and/or joining refers to either chemical or genetic conjugation.

In certain embodiments, the chimeric polypeptides of the present disclosure can be generated using well-known cross-linking reagents and protocols. For example, there are a large number of chemical cross-linking agents that are known to those skilled in the art and useful for cross-linking the alpha-amylase polypeptide with an internalizing moiety (e.g., an antibody). For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MB S); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this disclosure. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NETS), or its water soluble analog N-hydroxysulfosuccinimide (sulfo-NHS). Primary amines (lysine epsilon groups) at alkaline pH's are unprotonated and react by nucleophilic attack on NHS or sulfo- NETS esters. This reaction results in the formation of an amide bond, and release of NETS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

In some embodiments, the chimeric polypeptide comprises multiple linkers. For example, if the chimeric polypeptide comprises an scFv internalizing moiety, the chimeric polypeptide may comprise a first linker conjugating the alpha-amylase to the internalizing moiety, and a second linker in the scFv conjugating the $V_H$ domain (e.g., SEQ ID NO: 2) to the $V_L$ domain (e.g., SEQ ID NO: 3).

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain specific embodiments, chimeric polypeptides of the disclosure can be produced by using a universal carrier system. For example, a alpha-amylase polypeptide can be conjugated to a common carrier such as protein A, poly-L-lysine, hex-histidine, and the like. The conjugated carrier will then form a complex with an antibody which acts as an internalizing moiety. A small portion of the carrier molecule that is responsible for binding immunoglobulin could be used as the carrier.

In certain embodiments, chimeric polypeptides of the disclosure can be produced by using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). In any of the foregoing methods of cross-linking for chemical conjugation of alpha-amylase to an internalizing moiety, a cleavable domain or cleavable linker can be used. Cleavage will allow separation of the internalizing moiety and the alpha-amylase polypeptide. For example, following penetration of a cell by a chimeric polypeptide, cleavage of the cleavable linker would allow separation of alpha-amylase from the internalizing moiety.

In certain embodiments, the chimeric polypeptides comprising a alpha-amylase polypeptide and an internalizing moiety portion can be generated as a fusion protein containing the alpha-amylase polypeptide and the internalizing moiety. In certain embodiments, the chimeric polypeptides of the present disclosure can be generated as a fusion protein containing a alpha-amylase polypeptide and an internalizing moiety (e.g., an antibody or a homing peptide), expressed as one contiguous polypeptide chain. In certain embodiments, the chimeric polypeptide is generated as a fusion protein that comprises an alpha-amylase polypeptide portion and internalizing moiety portion. In preparing such fusion protein, a fusion gene is constructed comprising nucleic acids which encode a alpha-amylase polypeptide and an internalizing moiety, and optionally, a peptide linker sequence to span the alpha-amylase polypeptide and the internalizing moiety. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or staggerended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The chimeric polypeptides encoded by the fusion gene may be recombinantly produced using various expression systems as is well known in the art (also see below).

Recombinantly conjugated chimeric polypeptides include embodiments in which the alpha-amylase polypeptide is conjugated to the N-terminus or C-terminus of the internalizing moiety. Exemplary chimeric polypeptides in which alpha-amylase are conjugated to variant light and heavy chains of Fv3E10 are indicated in SEQ ID NOs: 3 and 2, respectively.

Recombinantly conjugated chimeric polypeptides include embodiments in which the internalizing moiety is N-terminal to the alpha-amylase polypeptide and embodiments in which the internalizing moiety is C-terminal to the alpha-amylase polypeptide portion. We note that methods of making fusion proteins recombinantly are well known in the art. Any of the chimeric proteins described herein can readily be made recombinantly. This includes proteins having one or more tags and/or one or more linkers. For example, if the chimeric polypeptide comprises an scFv internalizing moiety, the chimeric polypeptide may comprise a first linker interconnection the internalizing moiety to the alpha-amylase polypeptide portion, and a second linker in the scFv conjugating the $V_H$ domain. Moreover, in certain embodiments, the chimeric polypeptides comprise a "AGIH" portion (SEQ ID NO: 25) on the N-terminus of the chimeric polypeptide (or within 10 amino acid residues of the N-terminus), and such chimeric polypeptides may be provided in the presence or absence of one or more epitope tags. In further embodiments, the chimeric polypeptide comprises a serine at the N-terminal most position of the polypeptide. In some embodiments, the chimeric polypeptides comprise an "SAGIH" (SEQ ID NO: 26) portion at the N-terminus of the polypeptide (or within 10 amino acid residues of the N-terminus), and such chimeric polypeptides may be provided in the presence or absence of one or more epitope tags.

In some embodiments, the chimeric polypeptides comprise a signal sequence (e.g., SEQ ID NO: 4 or 5). In some embodiments, the signal sequence (e.g., SEQ ID NO: 5) is at the N-terminus of the light chain sequence of any of the antibodies or antigen binding fragments disclosed herein. In some embodiments, the signal sequence (e.g., SEQ ID NO: 5) is at the N-terminus of the amino acid sequence SEQ ID NO: 3, or fragments or variants thereof. In some embodiments, the signal sequence (e.g., SEQ ID NO: 4) is at the N-terminus of the heavy chain sequence of any of the antibodies or antigen binding fragments disclosed herein. In some embodiments, the signal sequence (e.g., SEQ ID NO: 4) is at the N-terminus of the amino acid sequence SEQ ID NO: 2, or fragments or variants thereof.

In some embodiments, the chimeric polypeptides are produced recombinantly in cells. In some embodiments, the cells are bacteria (e.g., *E. coli*), yeast (e.g., *Picchia*), insect cells (e.g., 519 cells) or mammalian cells (e.g., CHO or HEK-293 cells). Chimeric polypeptides of the disclosure are, in certain embodiments, made in any of the foregoing cells in culture using art recognized techniques for making and purifying protein from cells or cell supernatant.

The presence in the chimeric polypeptide of all or a portion of an immunoglobulin or an epitope tag, such as an HA or myc tag, provides a region for purification of chimeric polypeptide.

In some embodiments, the immunogenicity of the chimeric polypeptide may be reduced by identifying a candidate T-cell epitope within a junction region spanning the chimeric polypeptide and changing an amino acid within the junction region as described in U.S. Patent Publication No. 2003/0166877.

Chimeric polypeptides according to the disclosure can be used for numerous purposes. We note that any of the chimeric polypeptides described herein can be used in any of the methods described herein, and such suitable combinations are specifically contemplated.

Chimeric polypeptides described herein can be used to deliver alpha-amylase polypeptide to cells, particular to a muscle cell. In certain embodiments, chimeric polypeptides deliver alpha-amylase to liver cells. Thus, the chimeric polypeptides can be used to facilitate transport of alpha-amylase to cells in vitro or in vivo. By facilitating transport to cells, the chimeric polypeptides improve delivery efficiency, thus facilitating working with alpha-amylase polypeptide in vitro or in vivo. Further, by increasing the efficiency of transport, the chimeric polypeptides may help decrease the amount of alpha-amylase needed for in vitro or in vivo experimentation. Moreover, by facilitating delivery to the cytoplasm, the chimeric polypeptides and methods of the disclosure can address the problems associated with cytoplasmic accumulation of glycogen in, for example, Lafora Disease.

The chimeric polypeptides can be used to study the function of alpha-amylase in cells in culture, as well as to study transport of alpha-amylase. The chimeric polypeptides can be used to identify binding partners for alpha-amylase in cells, such as transport between cytoplasm and lysosome. The chimeric polypeptides can be used in screens to identify modifiers (e.g., small organic molecules or polypeptide modifiers) of alpha-amylase activity in a cell. The chimeric polypeptides can be used to help treat or alleviate the symptoms of Lafora Disease in humans or in an animal model. The foregoing are merely exemplary of the uses for the subject chimeric polypeptides.

Any of the chimeric polypeptides described herein, including chimeric polypeptides combining any of the features of the alpha-amylase polypeptides, internalizing moieties, and linkers, may be used in any of the methods of the disclosure.

IV. Alpha-Amylase-Related Nucleic Acids and Expression

In certain embodiments, the present disclosure makes use of nucleic acids for producing an alpha-amylase polypeptide (including a mature alpha-amylase polypeptide and functional fragments, variants, and fusions thereof). In certain specific embodiments, the nucleic acids may further comprise DNA which encodes an internalizing moiety for making a recombinant chimeric protein of the disclosure.

In certain embodiments, the disclosure relates to isolated or recombinant nucleic acid sequences that are at least 80%, 85%, 90%, 95%, 97%, 98%, 99% or 100% identical to a region of an alpha-amylase nucleotide sequence (e.g., GenBank Accession No. AH002672.1 or AH002671.1). In some embodiments, the nucleotide sequence encodes a mature alpha-amylase polypeptide sequence. In particular embodiments, the alpha-amylase nucleotide sequence encodes an alpha-amylase polypeptide that lacks the amino acids corresponding to amino acids 1-15 of SEQ ID NO: 1. In further embodiments, the alpha-amylase nucleic acid sequences can be isolated, recombinant, and/or fused with a heterologous nucleotide sequence, or in a DNA library.

In certain embodiments, alpha-amylase nucleic acids also include nucleotide sequences that hybridize under highly stringent conditions to any of the above-mentioned nucleotide sequences, or complement sequences thereof. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the native alpha-amylase nucleic acids due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In some embodiments, any of the nucleic acids disclosed herein are codon optimized for expression in a particular cell expression system, e.g., a mammalian cell, a yeast cell, a bacterial cell, a plant cell or an insect cell. In some embodiments, the nucleic acids are codon optimized for expression in a mammalian cell, such as a CHO or HEK-293 cell.

In certain embodiments, the recombinant alpha-amylase nucleic acids may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used. In certain aspects, this disclosure relates to an expression vector comprising a nucleotide sequence encoding a alpha-amylase polypeptide, such as any of the alpha-amylase polypeptides described herein, and operably linked to at least one regulatory sequence. Regulatory sequences are art-recognized and are selected to direct expression of the encoded polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). It should be understood that the design of the expression vector may depend on such factors as the choice of the host cell (e.g., Chinese Hamster Ovary cells) to be transformed and/or the type of protein desired to be expressed. Moreover, the vector's copy number, the ability to control that copy number and the expression of any other protein encoded by the vector, such as antibiotic markers, should also be considered.

In some embodiments, a nucleic acid construct, comprising a nucleotide sequence that encodes a alpha-amylase polypeptide or a bioactive fragment thereof, is operably linked to a nucleotide sequence that encodes an internalizing moiety, wherein the nucleic acid construct encodes a chimeric polypeptide having alpha-amylase biological activity. In certain embodiments, the nucleic acid constructs may further comprise a nucleotide sequence that encodes a linker.

This disclosure also pertains to a host cell transfected with a recombinant gene which encodes a alpha-amylase polypeptide or a chimeric polypeptide of the disclosure. The host cell may be any prokaryotic or eukaryotic cell. For example, a alpha-amylase polypeptide or a chimeric polypeptide may be expressed in bacterial cells such as *E. coli*, insect cells (e.g., using a baculovirus expression system), yeast, or mammalian cells. Other suitable host cells are known to those skilled in the art.

The present disclosure further pertains to methods of producing a alpha-amylase polypeptide or a chimeric polypeptide of the disclosure. For example, a host cell transfected with an expression vector encoding a alpha-amylase polypeptide or a chimeric polypeptide can be cultured under appropriate conditions to allow expression of the polypeptide to occur. The polypeptide may be secreted and isolated from a mixture of cells and medium containing the polypeptides. Alternatively, the polypeptides may be retained cytoplasmically or in a membrane fraction and the cells harvested, lysed and the protein isolated. A cell culture includes host cells, media and other byproducts. Suitable media for cell culture are well known in the art. The polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptides (e.g., an alpha-amylase polypeptide). In a preferred embodiment, the polypeptide is a fusion protein containing a domain which facilitates its purification.

A recombinant alpha-amylase nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

The disclosure contemplates methods of producing chimeric proteins recombinantly, such as described above. Suitable vectors and host cells may be readily selected for expression of proteins in, for example, yeast or mammalian cells. Host cells may express a vector encoding a chimeric polypeptide stably or transiently. Such host cells may be cultured under suitable conditions to express chimeric polypeptide which can be readily isolated from the cell culture medium.

Chimeric polypeptides of the disclosure (e.g., polypeptides comprising a mature alpha-amylase portion and an internalizing moiety portion) may be expressed as a single polypeptide chain or as more than one polypeptide chains. An example of a single polypeptide chain is when a alpha-amylaseportion is fused inframe to an internalizing moiety, which internalizing moiety is an scFv. In certain embodiments, this single polypeptide chain is expressed from a single vectors as a fusion protein.

An example of more than one polypeptide chains is when the internalizing moiety is an antibody or Fab. In certain embodiments, the heavy and light chains of the antibody or Fab may be expressed in a host cell expressing a single vector or two vectors (one expressing the heavy chain and one expressing the light chain). In either case, the alpha-amylase polypeptide may be expressed as an inframe fusion to, for example, the C-terminus of the heavy chain such that the alpha-amylase polypeptide is appended to the internalizing moiety but at a distance to the antigen binding region of the internalizing moiety.

As noted above, methods for recombinantly expressing polypeptides, including chimeric polypeptides, are well known in the art. Nucleotide sequences expressing a mature alpha-amylase polypeptide, such as a human mature alpha-amylase polypeptide, having a particular amino acid sequence are available and can be used. Moreover, nucleotide sequences expressing an internalizing moiety portion, such as expressing a 3E10 antibody, scFv, or Fab comprising the VH and VL set forth in SEQ ID NO: 2 and 3) are publicly available and can be combined with nucleotide sequence encoding suitable heavy and light chain constant regions. The disclosure contemplates nucleotide sequences encoding any of the chimeric polypeptides of the disclosure, vectors (single vector or set of vectors) comprising such nucleotide sequences, host cells comprising such vectors, and methods of culturing such host cells to express chimeric polypeptides of the disclosure.

V. Methods of Treatment and Other Methods of Use

For any of the methods described herein, the disclosure contemplates the use of any of the chimeric polypeptides and/or compositions described throughout the application. In addition, for any of the methods described herein, the disclosure contemplates the combination of any step or steps of one method with any step or steps from another method.

For example, a chimeric polypeptide of the disclosure comprising a mature alpha-amylase polypeptide (e.g., a mature alpha-amylase polypeptide) portion and an internalizing moiety portion can be used in any of the methods of the disclosure.

In certain embodiments, a chimeric polypeptide of the disclosure (e.g., a polypeptide comprising a mature alpha-amylase polypeptide portion and an internalizing moiety portion) is delivered to the cytoplasm of cells, such as muscle (e.g., diaphragm muscle and/or cardiac muscle), neuronal cells (e.g., neuronal cells of the brain) and/or liver cells to decrease cytoplasmic glycogen accumulation (e.g., deleterious accumulation of normal of abnormal glycogen, such as polyglucosan). Such cells may be present in vitro or in a subject (e.g., a patient, such as a human). In certain embodiments, the subject is a subject having, or suspected or having, a glycogen storage disorder, particularly Pompe Disease, GSD III, or GSD IV, and/or a glycogen metabolism disorder, such as Lafora Disease. In certain embodiments, a chimeric polypeptide of the disclosure is suitable for use in delivering alpha-amylase to cytoplasm in a subject in need thereof, such as a subject having Pompe Disease, GSD III, or GSD IV, and/or a glycogen metabolism disorder, such as Lafora Disease. In certain embodiments, the subject in need thereof has or is suspected of having GSD III. In certain embodiments, the subject in need thereof has or is suspected of having GSD IV. In certain embodiments, the disclosure provides a method of treating (e.g., improving one or more symptoms of; decreasing glycogen accumulation, such as cytoplasmic glycogen accumulation) GSD III. In certain embodiments, the disclosure provides a method of treating (e.g., improving one or more symptoms of; decreasing glycogen accumulation, such as cytoplasmic glycogen accumulation) GSD IV. In certain embodiments, the disclosure provides a method of treating (e.g., improving one or more symptoms of; decreasing glycogen accumulation) Lafora Disease. In certain embodiments, the disclosure provides a method of treating a disease or disorder associated with hypoxia-induced glycogen accumulation. In some embodiments, the disease or disorder associated with hypoxia-induced glycogen accumulation is cancer. Further methods are described herein.

In some embodiments, any of the chimeric polypeptides disclosed herein may be used to decrease glycogen accumulation in an acidic cellular compartment (e.g., a lysosome or an autophagosome). In some embodiments, the chimeric polypeptides may be used to decrease glycogen accumulation in one or more cells of a patient having a disease associated with glycogen accumulation in acidic cellular compartments (e.g., lysosomes or autophagosomes). In some embodiments, the chimeric polypeptides may be used to decrease glycogen accumulation in a Pompe Disease (GSD II) cell. In some embodiments, the chimeric polypeptides may be used to treat a patient having Pompe Disease (GSD II).

In some embodiments, the chimeric polypeptides of the disclosure may be used to increase glycogen clearance in a cell. In some embodiments, the cell is a muscle (e.g., cardiac or diaphragm muscle), liver or neuronal (e.g., of the brain) cell. In some embodiments, the cell is in a subject having Lafora Disease.

In certain embodiments, chimeric polypeptides comprising any of the alpha-amylase polypeptides disclosed herein can be used to treat Lafora Disease. In certain embodiments, chimeric polypeptides comprising any of the alpha-amylase polypeptides disclosed herein can be used to treat Forbes-Cori Disease. In certain embodiments, the present disclosure provides methods of delivering chimeric polypeptides to cells, including cells in culture (in vitro or ex vivo) and cells in a subject. Delivery to cells in culture, such as healthy cells or cells from a model of disease, have numerous uses. These uses include to identify alpha-amylase substrates or binding partners, to evaluate localization and/or trafficking (e.g., to cytoplasm, lysosome, and/or autophagic vesicles), to evaluate enzymatic activity under a variety of conditions (e.g., pH), to assess glycogen accumulation, and the like. In certain embodiments, chimeric polypeptides of the disclosure can be used as reagents to understand alpha-amylase activity, localization, and trafficking in healthy or disease contexts.

Delivery to subjects, such as to cells in a subject, has numerous uses. Exemplary therapeutic uses are described below. Moreover, the chimeric polypeptides may be used for diagnostic or research purposes. For example, a chimeric polypeptide of the disclosure may be detectably labeled and administered to a subject, such as an animal model of disease or a patient, and used to image the chimeric polypeptide in the subject's tissues (e.g., localization to muscle, brain and/or liver). Additionally exemplary uses include delivery to cells in a subject, such as to an animal model of disease (e.g., Lafora Disease). By way of example, chimeric polypeptides of the disclosure may be used as reagents and delivered to animals to understand alpha-amylase bioactivity, localization and trafficking, protein-protein interactions, enzymatic activity, and impacts on animal physiology in healthy or diseased animals.

In certain embodiments, the present disclosure provides methods of treating conditions associated with, dysfunction of laforin, alpha-amylase, and/or malin, with aberrant glycogen accumulation and/or with Lafora Disease. In certain embodiments, the glycogen accumulation is in the cytoplasm, and delivery of alpha-amylase reduces cytoplasmic glycogen accumulation, such as in skeletal muscle or liver. In certain embodiments, the subject does not have dysfunction in endogenous laforin, alpha-amylase, and/or malin (e.g., the methods do not comprise replacement of the protein that is mutated or for which there is dysfunction).

In certain embodiments, these methods involve administering to the individual a therapeutically effective amount of a chimeric polypeptide as described above (e.g., a chimeric polypeptide comprising (i) an alpha-amylase polypeptide and (ii) an internalizing moiety portion). These methods are particularly aimed at therapeutic and prophylactic treatments of animals, and more particularly, humans. With respect to methods for treating Lafora Disease, the disclosure contemplates all combinations of any of the foregoing aspects and embodiments, as well as combinations with any of the embodiments set forth in the detailed description and examples. Accordingly, chimeric polypeptides of the disclosure are, in certain embodiments, suitable for treating diseases such as Lafora Disease. In certain embodiments, the chimeric polypeptide decreases glycogen accumulation in cells, such as muscle cells (e.g., diaphragm muscle or cardiac muscle cells), liver cells, and/or neuronal cells, to treat Lafora Disease in a patient in need thereof.

The present disclosure provides a method of delivering a chimeric polypeptide or nucleic acid construct into a cell via an equilibrative nucleoside transporter (ENT2) pathway, comprising contacting a cell with a chimeric polypeptide or nucleic acid construct. In certain embodiments, the method comprises contacting a cell with a chimeric polypeptide, which chimeric polypeptide comprises an alpha-amylase polypeptide or bioactive fragment thereof and an internalizing moiety which can mediate transport across a cellular membrane via an ENT2 pathway (and optionally via another ENT transporter, such as ENT3), thereby delivering the chimeric polypeptide into the cell. In certain embodiments, the cell is a muscle cell. The muscle cells targeted using any of the methods disclosed herein may include skeletal (e.g., diaphragm), cardiac or smooth muscle cells. In other embodiments, the chimeric polypeptides are delivered to liver or neuronal (e.g., brain) cells.

The present disclosure also provides a method of delivering a chimeric polypeptide or nucleic acid construct into a cell via a pathway that allows access to cells other than muscle cells. Other cell types that could be targeted using any of the methods disclosed herein include, for example, liver cells, neurons (e.g., of the brain), epithelial cells, uterine cells, and kidney cells.

In certain embodiments, the internalizing moiety is an antibody or antigen binding fragment, such as an antibody or antigen binding fragment that binds DNA. In certain embodiments, the internalizing moiety is an antibody, such as a full length antibody or a Fab. In certain embodiments, the full length antibody or Fab comprises one or more substitutions, relative to a native immunoglobulin constant region, such as to decrease effector function.

Lafora Disease, also called Lafora progressive myoclonic epilepsy or MELF, is a rare, fatal neurodegenerative disorder characterized by the accumulation of cytoplasmic polyglucosan inclusion bodies (known as Lafora bodies) in cells from most tissues of affected individuals, including the brain, heart, liver, muscle and skin. Lafora Disease patients typically first develop symptoms in adolescence. Symptoms include temporary blindness, depression, seizures, drop attacks, myoclonus, visual hallucinations, absences, ataxia and quickly developing and severe dementia. Death usually occurs 2-10 years (5 years mean) after onset.

The prevalence of Lafora Disease is unknown. While this disease occurs worldwide, it is most common in Mediterranean countries, parts of Central Asia, India, Pakistan, North Africa and the Middle East. In Western countries, the prevalence is estimated to be below $1/1,000,000$.

There is currently no cure or effective treatment for patients having Lafora Disease. However, the seizures and myoclonus can be managed, at least in early stages of the disease, with antiepileptic medications.

The terms "treatment", "treating", and the like are used herein to generally mean obtaining a desired pharmacologic and/or physiologic effect. "Treating" a condition or disease refers to curing as well as ameliorating at least one symptom of the condition or disease, and includes administration of a composition which reduces the frequency of, or delays the onset of, symptoms of a medical condition in a subject in need relative to a subject which does not receive the composition. "Treatment" as used herein covers any treatment of a disease or condition of a mammal, particularly a human, and includes: (a) preventing symptoms of the disease or condition from occurring in a subject which may be predisposed to the disease or condition but has not yet begun experiencing symptoms; (b) inhibiting the disease or condition (e.g., arresting its development); or (c) relieving the disease or condition (e.g., causing regression of the disease or condition, providing improvement in one or more symptoms). For example, "treatment" of Lafora Disease is contemplated and encompasses a complete reversal or cure of the disease, or any range of improvement in symptoms and/or adverse effects attributable to the disease.

Merely to illustrate, "treatment" of Lafora Disease includes an improvement in any of the following effects associated with Lafora Disease or combination thereof: blindness, depression, seizures, drop attacks, hepatic disease, muscle atrophy, myoclonus, visual hallucinations, absences, ataxia, dementia, and/or shortened lifespan. Treatment may also include a reduction of Lafora bodies and or aberrant accumulation of polyglucosan in, for example, muscle (e.g., cardiac or diaphragm), liver and/or brain. Other symptoms not listed above may also be monitored in order to determine the effectiveness of treating Lafora Disease. The population of subjects treated by the method of the disclosure includes subjects suffering from the undesirable condition or disease, as well as subjects at risk for development of the condition or disease. In certain embodiments, the subject being treated is treated before onset of dementia or before onset of measureable, appreciable dementia.

In certain embodiments, the disclosure provides methods of delivering alpha-amylase activity to cells, such as muscle and/or liver and/or kidney cells of a subject having Lafora Disease comprising administering a chimeric polypeptide of the disclosure or a composition comprising a chimeric polypeptide of the disclosure formulated with one or more pharmaceutically acceptable carriers and/or excipients.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, administration of a chimeric polypeptide of the disclosure is via any one of the routes of administration described herein, such as subcutaneous, intravenous, or via the hepatic portal vein. In other words, the disclosure contemplates methods of delivery by administering via any such route of administration.

In certain embodiments, the method results in delivery of greater alpha-amylase activity to the cytoplasm, in comparison, to that following deliver of a alpha-amylase polypeptide that is not conjugated to an internalizing moiety and/or in comparison to that of a alpha-amylase polypeptide conjugated to a different internalizing moiety.

In certain embodiments, one or more chimeric polypeptides of the present disclosure can be administered, together (simultaneously) or at different times (sequentially). In addition, chimeric polypeptides of the present disclosure can be administered alone or in combination with one or more additional compounds or therapies for treating Lafora Disease. For example, one or more chimeric polypeptides can be co-administered in conjunction with one or more other therapeutic compounds. When co-administration is indicated, the combination therapy may encompass simultaneous or alternating administration. In addition, the combination may encompass acute or chronic administration. Optionally, the chimeric polypeptide of the present disclosure and additional compounds act in an additive or synergistic manner for treating Lafora Disease. Additional compounds to be used in combination therapies include, but are not limited to, small molecules, polypeptides, antibodies, antisense oligonucleotides, and siRNA molecules. Depending on the nature of the combinatory therapy, administration of the chimeric polypeptides of the disclosure may be continued while the other therapy is being administered and/or thereafter. Administration of the chimeric polypeptides may be made in a single dose, or in multiple doses. In some instances, administration of the chimeric polypeptides is commenced at least several days prior to the other therapy, while in other instances, administration is begun either immediately before or at the time of the administration of the other therapy.

In some embodiments, any of the chimeric polypeptides described herein are administered to a subject (e.g., a subject having Lafora Disease) in combination with an anti-epileptic drug. In some embodiments, any of the chimeric polypeptides described herein are administered to a subject (e.g., a subject having Lafora Disease) in combination with any of the chimeric polypeptides disclosed in WO 2015/192092, which is incorporated by reference in its entirety. In particular embodiments, any of the chimeric polypeptides described herein are administered to a subject (e.g., a subject having Lafora Disease) in combination with any of the malin and/or laforin chimeric polypeptides disclosed in WO 2015/192092.

In another example of combination therapy, one or more chimeric polypeptides of the disclosure can be used as part of a therapeutic regimen combined with one or more additional treatment modalities. By way of example, such other treatment modalities include, but are not limited to, dietary therapy, occupational therapy, physical therapy, ventilator supportive therapy, massage, acupuncture, acupressure, mobility aids, assistance animals, and the like.

In certain embodiments, one or more chimeric polypeptides of the present disclosure can be administered prior to or following a liver transplant.

Note that although the chimeric polypeptides described herein can be used in combination with other therapies, in certain embodiments, a chimeric polypeptide is provided as the sole form of therapy. Regardless of whether administrated alone or in combination with other medications or therapeutic regiments, the dosage, frequency, route of administration, and timing of administration of the chimeric polypeptides is determined by a physician based on the condition and needs of the patient. The disclosure contemplates that a method may comprise administration at a dose and on a dosing schedule, such as administration at specified intervals over a period of time. In such cases, each dose contributes to efficacy, and is thus effective, although improvement in symptoms may only be observed after administration of multiple doses.

Chimeric polypeptides of the disclosure have numerous uses, including in vitro and in vivo uses. In vivo uses include not only therapeutic uses but also diagnostic and research uses in, for example, any of the foregoing animal models. By way of example, chimeric polypeptides of the disclosure may be used as research reagents and delivered to animals to understand alpha-amylase bioactivity, localization and trafficking, protein-protein interactions, enzymatic activity, and impacts on animal physiology in healthy or diseases animals.

Chimeric polypeptides may also be used in vitro to evaluate, for example, alpha-amylase bioactivity, localization and trafficking, protein-protein interactions, and enzymatic activity in cells in culture, including healthy and alpha-amylase deficient cells in culture. The disclosure contemplates that chimeric polypeptides of the disclosure may be used to deliver alpha-amylase to cytoplasm, lysosome, and/or autophagic vesicles of cells, including cells in culture.

The disclosure contemplates that any of the methods described herein may be carried out by administering or contacting cells with a chimeric polypeptide of the disclosure and/or a composition of the disclosure (e.g., a composition comprising a chimeric polypeptide of the disclosure formulated with one or more pharmaceutically acceptable carriers and/or excipients).

VI. Gene Therapy

Conventional viral and non-viral based gene transfer methods can be used to introduce nucleic acids encoding polypeptides of alpha-amylase (e.g., a mature alpha-amylase) and or chimeric polypeptides comprising alpha-amylase in mammalian cells or target tissues. Such methods can be used to administer nucleic acids encoding polypeptides of the disclosure (e.g., alpha-amylase including variants thereof, and include chimeric polypeptides) to cells in vitro. The disclosure contemplates that gene transfer methods may be used to deliver nucleic acid encoding any of the chimeric polypeptides of the disclosure or alpha-amylase polypeptides. In some embodiments, the nucleic acids encoding alpha-amylase are administered for in vivo or ex vivo gene therapy uses. In other embodiments, gene delivery techniques are used to study the activity of chimeric polypeptides or alpha-amylase polypeptide or to study Lafora Disease in cell based or animal models, such as to evaluate cell trafficking, enzyme activity, and protein-protein interactions following delivery to healthy or diseased cells and tissues. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the disclosure include lipofection, microinjection, biolistics, virosomes, liposomes, immunoliposomes, polycation or lipid:nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art.

The use of RNA or DNA viral based systems for the delivery of nucleic acids encoding alpha-amylase or its variants take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the disclosure could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SW), human immuno deficiency virus (HIV), and combinations thereof, all of which are well known in the art.

In applications where transient expression of the polypeptides of the disclosure is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures. Construction of recombinant AAV vectors are described in a number of publications, including U.S. Pat. No. 5,173,414; Tratschin et al., *Mol. Cell. Biol.* 5:3251-3260 (1985); Tratschin, et al.; *Mol. Cell. Biol.* 4:2072-2081 (1984); Hermonat & Muzyczka, *PNAS* 81:6466-6470 (1984); and Samulski et al., *J. Virol.* 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system.

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity.

Packaging cells are used to form virus particles that are capable of infecting a host cell. Such cells include 293 cells, which package adenovirus, and 42 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells, such as muscle cells.

Gene therapy vectors can be delivered in vivo by administration to an individual patient, by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. For example, cells are isolated from the subject organism, transfected with a nucleic acid (gene or cDNA) encoding, e.g., alpha-amylase or its variants, and re-infused back into the subject organism (e.g., patient). Various cell types suitable for ex vivo transfection are well known to those of skill in the art.

In certain embodiments, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Stem cells are isolated for transduction and differentiation using known methods.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present disclosure, as described herein.

VII. Methods of Administration

Various delivery systems are known and can be used to administer the chimeric polypeptides of the disclosure. Any such methods may be used to administer any of the chimeric polypeptides described herein. The disclosure contemplates than any of the methods of administration disclosed herein may be used to deliver any of the chimeric polypeptides of the disclosure in the context of any of the methods described herein (e.g., methods of treatment; methods of reducing cytoplasmic glycogen accumulation).

Methods of introduction can be enteral or parenteral, including but not limited to, intradermal, intramuscular, intraperitoneal, intramyocardial, intravenous, subcutaneous, pulmonary, intranasal, intraocular, epidural, intrathecal, intracranial, intraventricular and oral routes. The chimeric polypeptides may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

In certain embodiments, the chimeric polypeptide is administered intravenously.

In certain embodiments, it may be desirable to administer the chimeric polypeptides of the disclosure locally to the area in need of treatment (e.g., muscle); this may be achieved, for example, and not by way of limitation, by local infusion during surgery, by means of a catheter, or by means of an implant, the implant being of a porous, non-porous, or gelatinous material, including membranes, such as sialastic membranes, fibers, or commercial skin substitutes.

In another embodiment, such local administration can be to all or a portion of the heart. For example, administration can be by intrapericardial or intramyocardial administration. Similarly, administration to cardiac tissue can be achieved using a catheter, wire, and the like intended for delivery of agents to various regions of the heart.

In another embodiment, local administration is directed to the liver. Glycogen storage and glycogenolysis in the liver affect the availability of glycogen for many other tissues in the body. For example, a venous catheter may be placed in the hepatic portal vein to deliver chimeric polypeptides directly to the liver. In addition, in some embodiments where the internalizing moieties of the chimeric polypeptides show a lower affinity for liver cells than for other cell types, delivery through the hepatic portal vein ensures that adequate concentrations of alpha-amylase reach the liver cells.

Note that the disclosure contemplates methods in which chimeric polypeptides are administered, at the same or different times, via one than one route of administration. For example, the disclosure contemplates a regimen in which chimeric polypeptides are administered systemically, such as by intravenous infusion, in combination with local administration via the hepatic portal vein.

In other embodiments, the chimeric polypeptides of the disclosure can be delivered in a vesicle, in particular, a liposome (see Langer, 1990, Science 249:1527-1533). In yet another embodiment, the chimeric polypeptides of the disclosure can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, the chimeric polypeptides of the disclosure can be delivered intravenously.

In certain embodiments, the chimeric polypeptides are administered by intravenous infusion. In certain embodiments, the chimeric polypeptides are infused over a period of at least 10, at least 15, at least 20, or at least 30 minutes. In other embodiments, the chimeric polypeptides are infused over a period of at least 60, 90, or 120 minutes. Regardless of the infusion period, the disclosure contemplates that each infusion is part of an overall treatment plan where chimeric polypeptide is administered according to a regular schedule (e.g., weekly, monthly, etc.).

The foregoing applies to any of the chimeric polypeptides, compositions, and methods described herein. The disclosure specifically contemplates any combination of the features of such chimeric polypeptides, compositions, and methods (alone or in combination) with the features described for the various pharmaceutical compositions and route of administration described in this section.

VIII. Pharmaceutical Compositions

In certain embodiments, the subject chimeric polypeptides for use in any of the methods disclosed herein are formulated with a pharmaceutically acceptable carrier (e.g., formulated with one or more pharmaceutically acceptable carriers and/or excipients). One or more chimeric polypeptides can be administered alone or as a component of a pharmaceutical formulation (composition). Any of the chimeric polypeptides described herein may be formulated, as described herein, and any such compositions (e.g., pharmaceutical compositions, or preparations, or formulations) may be used in any of the methods described herein. In other embodiments, the composition comprises a chimeric polypeptide comprising an alpha-amylase polypeptide. The chimeric polypeptides may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject chimeric polypeptides include, for example, those suitable for oral, nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

In certain embodiments, any of the pharmaceutical compositions described herein comprise concentrated amounts of any of the chimeric polypeptides described herein. In some embodiments, the compositions have 50%, 100%, 150%, 200%, 250%, 300%, 350% or 400% more concentrated levels of the chimeric polypeptide as compared to the levels of chimeric polypeptide originally purified from the cells producing the chimeric polypeptide. In some embodiments, the concentration of the chimeric polypeptide is at least 2, 3, 4, 5, 6, 7, 8, 9, 10, 11, 12, 13, 14, 15, 16, 17, 18, 19, or 20 mg/ml. In some embodiments, the concentration of the chimeric polypeptide is at least 10 mg/ml or greater. In some embodiments, the concentration of the chimeric polypeptide is at least 15 mg/ml or greater. In some embodiments, the concentration of the chimeric polypeptide is at least 20 mg/ml or greater. In some embodiments, the concentration of the chimeric polypeptide is at least 30 mg/ml or greater. In some embodiments, the concentration of the chimeric polypeptide is at least 50 mg/ml or greater. In some embodiments, the concentration of the chimeric polypeptide is at least 70 mg/ml or greater. In some embodiments, the concentration of the chimeric polypeptide is at least 90 mg/ml or greater. In some embodiments, the concentration of the chimeric polypeptide is at least 110 mg/ml or greater. In some embodiments, the concentration of the chimeric polypeptide is 10-50 mg/ml, 10-40 mg/ml, 10-30 mg/ml, 10-25 mg/ml, 10-20 mg/ml. 20-50 mg/ml, 50-70 mg/ml, 70-90 mg/ml or 90-110 mg/ml. In some embodiments, any of the compositions described herein preserve at least 80%, 90%, 95% or 100% biological activity (as defined herein) for at least 24 hours, 2 days, 4 days, 1 week, 2 weeks or 1 month when stored in a pharmaceutically acceptable formulation at 4° C. In some embodiments of any of the foregoing, the chimeric polypeptide portion of the composition is substantially pure, as described herein (e.g., greater than 85% of the alpha-amylase present is in association or interconnected with an internalizing moiety).

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject chimeric polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more chimeric polypeptide therapeutic agents of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In certain embodiments, methods of the disclosure include topical administration, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers (e.g., HEPES buffer), or propellants which may be required. The ointments, pastes, creams and gels may contain, in addition to a subject chimeric polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject chimeric polypeptides, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more chimeric polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers (e.g., HEPES buffer), bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the chimeric polypeptides of the present disclosure are formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another embodiment, the chimeric polypeptides of the present disclosure are formulated for subcutaneous administration to human beings.

In certain embodiments, the chimeric polypeptides of the present disclosure are formulated for intrathecal, intracranial and/or intraventricular delivery. In certain embodiments, a chimeric polypeptide of the disclosure for use in treating Lafora Disease or for use in decreasing glycogen accumulation in neurons, such as in a subject having Lafora Disease, is formulated for intrathecal, intracranial and/or intraventricular delivery. In certain embodiments, a method of the disclosure, such as a method of treating Lafora Disease or for decreasing glycogen accumulation in neurons comprising delivering a chimeric polypeptide of the disclosure intrathecally, intracranially and/or intraventricularly.

In certain embodiments, the chimeric polypeptides of the present disclosure are formulated for deliver to the heart, such as for intramyocardial or intrapericaridal delivery.

In certain embodiments, the composition is intended for local administration to the liver via the hepatic portal vein, and the chimeric polypeptides are formulated accordingly.

Note that, in certain embodiments, a particular formulation is suitable for use in the context of deliver via more than one route. Thus, for example, a formulation suitable for intravenous infusion may also be suitable for delivery via the hepatic portal vein. However, in other embodiments, a formulation is suitable for use in the context of one route of delivery, but is not suitable for use in the context of a second route of delivery.

The amount of the chimeric polypeptides of the disclosure which will be effective in the treatment of a tissue-related condition or disease (e.g., Lafora Disease) can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

In certain embodiments, compositions of the disclosure, including pharmaceutical preparations, are non-pyrogenic. In other words, in certain embodiments, the compositions are substantially pyrogen free. In one embodiment the formulations of the disclosure are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in relatively large dosages and/or over an extended period of time (e.g., such as for the patient's entire life), even small amounts of harmful and dangerous endotoxin could be dangerous. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

In some embodiments, the disclosure provides a composition, such as a pharmaceutical composition comprising a chimeric polypeptide of the disclosure formulated with one or more pharmaceutically acceptable carriers and/or excipients. Such compositions include compositions comprising any of the internalizing moiety portions, described herein, and an alpha-amylase portion comprising, as described herein. For example, the disclosure provides compositions comprising an alpha-amylase-containing chimeric polypeptide. In certain embodiments, any of the compositions described herein may be based on any of the alpha-amylase portions and/or internalizing moiety portions described herein. Moreover, any such compositions may be described based on any of the structural and/or functional features described herein. Any such compositions may be used in any of the methods described herein, such as administered to cells and/or to subjects in need of treatment, such as administered to cells and/or to subjects having Lafora Disease. Any such compositions may be used to deliver alpha-amylase activity into cells, such as into muscle and/or liver cells in a patient in need thereof (e.g., a patient having Lafora Disease).

Such compositions, including any of the compositions described herein, may be provided, for example, in a bottle or syringe and stored prior to administration.

The foregoing applies to any of the chimeric polypeptides, compositions, and methods described herein. The disclosure specifically contemplates any combination of the features of such chimeric polypeptides, compositions, and methods (alone or in combination) with the features described for the various pharmaceutical compositions and route of administration described in this section.

IX. Animal Models

Mice engineered to be deficient in malin display a phenotype similar to that observed in human cases of Lafora Disease. Specifically, malin$^{-/-}$ mice presented in an age-dependent manner neurodegeneration, increased synaptic excitability, and propensity to suffer myoclonic seizures. Valles-Ortega et al., 2011, EMBO Mol Med, 3(11):667-681. In addition, these mice accumulated glycogen-filled inclusion bodies that were most abundant in the hippocampus and cerebellum, but that were also found in skeletal and cardiac muscle cells. Valles-Ortega et al. Glycogen was also found to be less branched in the cells of malin$^{-/-}$ mice as compared to glycogen observed in the cells of healthy control mice. Valles-Ortega et al. An increased level of glycogen hyperphosphorylation has also been described in this mouse model. Turnbull et al., 2010, Ann Neurol, 68(6):925-33.

Mice engineered to be deficient in laforin also display some phenotypic similarities to human cases of Lafora Disease. Specifically, laforin$^{-/-}$ mice are born developmentally normal, but develop an age-dependent ataxia and myoclonus epilepsy. Ganesh et al., 2002, Hum Mol Genet, 11(11):1251-62. In addition, laforin$^{-/-}$ mice display widespread degeneration of neurons by two months of age and the development of inclusion bodies by 4-12 months of age. Ganesh et al., 2002. Mice deficient for laforin also display hyperphosphorylation and aggregation of tau protein in the brain. Puri et al., 2009, J Biol Chem, 284(34):22657-63.

Accordingly, in certain embodiments, the present disclosure contemplates methods of surveying improvements in disease phenotypes using any of the alpha-amylase (e.g., a mature alpha-amylase) constructs of the disclosure disclosed herein in any one or more animal models, such as the mouse models described herein. By way of example, various parameters can be examined in experimental animals treated with a subject chimeric polypeptide, and such animals can be compared to controls. Exemplary parameters that can be assessed to evaluate potential efficacy include, but are not limited to: increase in lifespan; increase in glycogen clearance, decrease in glycogen accumulation, and improved muscle strength, for example in open field and open wire hang paradigms, improved heart function, improved liver function or decrease in liver size. Increase in glycogen clearance and decrease in glycogen accumulation may be assessed, for example, by periodic acid Schiff staining in a biopsy (e.g., muscle (e.g., cardiac or diaphragm), liver or neuronal) from a treated or untreated animal model. Further parameters that may be observed include a reduction in: neurodegeneration, number/duration/intensity of seizures, number or size of inclusion bodies, amount of glycogen hyperphosphorylation, ataxia, tau hyperphosphorylation and/or tau aggregation. In certain embodiments, the disclosure provides a method of decreasing cytoplasmic glycogen accumulation in a subject having any of the foregoing conditions. In particular embodiments, any of the parameters disclosed herein may be monitored in the skeletal muscle (e.g., diaphragm), liver, cardiac muscle, and or brain neurons from a Lafora Disease animal model.

Moreover, a complete pharmacokinetic study to determine the effective dose, clearance rate, volume of distribution, and half-life of any of the chimeric polypeptides described herein is determined. The PK/PD/TK of the final product can be examined in larger animals such as rats, dogs, and primates.

The above models are exemplary of suitable animal model systems for assessing the activity and effectiveness of the subject chimeric polypeptides and/or formulations. These models have correlations with symptoms of Lafora Disease, and thus provide appropriate models for studying Lafora Disease. Activity of the subject chimeric polypeptides and/or formulations is assessed in any one or more of these models, and the results compared to that observed in wildtype control animals and animals not treated with the chimeric polypeptides (or treated with alpha-amylase alone). Similarly, the subject chimeric polypeptides can be evaluated using cells in culture, for example, cells prepared from any of the foregoing mutant mice or other animals, as well as wild type cells, such as fibroblasts, myoblasts or hepatocytes. Cells from subjects having the disease may also be used. An example of an in vitro assay for testing activity of the chimeric polypeptides disclosed herein would be to treat Lafora Disease cells with or without the chimeric polypeptides and then, after a period of incubation, stain the cells for the presence of glycogen, e.g., by using a periodic acid Schiff (PAS) stain. The amount of inclusion bodies and glycogen hyperphosphorylation may also be monitored. Cell proliferation, morphology and cell death may also be monitored in treated or untreated cells.

Chimeric polypeptides of the disclosure have numerous uses, including in vitro and in vivo uses. In vivo uses include not only therapeutic uses but also diagnostic and research uses in, for example, any of the foregoing animal models. By way of example, chimeric polypeptides of the disclosure may be used as research reagents and delivered to animals to understand alpha-amylase bioactivity, localization and trafficking, protein-protein interactions, enzymatic activity, and impacts on animal physiology in healthy or diseased animals.

Chimeric polypeptides may also be used in vitro to evaluate, for example, alpha-amylase bioactivity, localization and trafficking, protein-protein interactions, and enzymatic activity in cells in culture, including healthy, diseased (but not alpha-amylase deficient) and laforin, alpha-amylase and/or malin deficient cells in culture. The disclosure contemplates that chimeric polypeptides of the disclosure may be used to deliver alpha-amylase to cytoplasm, lysosome, and/or autophagic vesicles of cells, including cells in culture. In some embodiments, the cultured cells are obtained from a Lafora Disease subject, such as from a Lafora Disease human patient or from a Lafora Disease animal model. In some embodiments, the chimeric polypeptides may be used in a hypoxic cell model, similar to that described in Pelletier et al., *Frontiers in Oncology*, 2(18): 1-9.

Additionally, cell free systems may be used to assess, for example, enzymatic activity of the subject chimeric polypeptides. For example, glycogen may be obtained from a sample from a healthy and/or a diseased subject (e.g. from a Lafora Disease subject), and the ability of any of the chimeric polypeptides disclosed herein to hydrolyze the glycogen may be assessed, e.g., in a manner similar to that described in the Example section provided herein. In some embodiments, the glycogen for used in such cell-free systems may be obtained from a muscle (e.g., diaphragm or cardiac muscle), liver, or neuronal (e.g., brain) cells from a subject (e.g., from a Lafora Disease subject). In some embodiments, the subject is a human Lafora Disease patient or an animal model of Lafora Disease.

Chimeric polypeptide, such as alpha-amylase chimeric polypeptides, may further be used to identify protein-protein interactions in systems where a protein such as alpha-amylase is not deficient, such as in Forbes-Cori Disease. Chimeric polypeptides may further be used to understand the relative benefit of decreasing accumulation of glycogen in certain cell types but potentially not all cell types in which symptoms are present. Chimeric polypeptides may be used to identify substrates for alpha-amylase particularly in settings where endogenous alpha-amylase is not mutated. Chimeric polypeptides are useful for evaluating trafficking of alpha-amylase and the chimeric polypeptides in healthy, as well as diseased cells where glycogen accumulation is due to different underlying causes.

X. Kits

In certain embodiments, the disclosure also provides a pharmaceutical package or kit comprising one or more containers filled with at least one chimeric polypeptide of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In certain embodiments, the kit includes additional materials to facilitate delivery of the subject chimeric polypeptides. For example, the kit may include one or more of a catheter, tubing, infusion bag, syringe, and the like. In certain embodiments, the chimeric polypeptide is packaged in a lyophilized form, and the kit includes at least two containers: a container comprising the lyophilized chimeric polypeptide and a container comprising a suitable amount of water, buffer (e.g., HEPES buffer), or other liquid suitable for reconstituting the lyophilized material.

The foregoing applies to any of the chimeric polypeptides, compositions, and methods described herein. The disclosure specifically contemplates any combination of the features of such chimeric polypeptides, compositions, and methods (alone or in combination) with the features described for the various kits described in this section.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example: Generation and Characterization of a Fab-Alpha-Amylase Protein

A. Synthesis of a Fab-Alpha-Amylase Protein

Chimeric polypeptides comprising a mature alpha-amylase polypeptide portion and an internalizing moiety portion were made recombinantly in two different mammalian cell lines, CHO-3E7 and HEK-293 6E cells. An alpha-amylase polypeptide comprising a mature alpha-amylase polypeptide (e.g., a polypeptide having the amino acid sequence of SEQ ID NO: 1) was fused to a Fab of a humanized 3E10 antibody comprising the heavy chain variable domain set forth in SEQ ID NO: 7. Specifically, an alpha-amylase polypeptide having the amino acid sequence of SEQ ID NO: 1 was fused to the C-terminus of the heavy chain constant region of a humanized 3E10 Fab fragment (which included the signal sequence of SEQ ID NO: 4) by means of a linker having the amino acid sequence of SEQ ID NO: 6 to generate a fusion polypeptide having the amino acid sequence of SEQ ID NO: 9. The light chain comprises the amino acid sequence of SEQ ID NO: 8 and the signal sequence of SEQ ID NO: 5 to provide the sequence of SEQ ID NO: 10. The resulting "Fab-alpha-amylase" comprising both the heavy chain and light chains is referred to in the experimental designs described below.

This Fab was made by expressing a vector encoding the light chain and a vector encoding the heavy chain-amylase fusion in either of two cell lines. Although two separate vectors were used, a single vector encoding both the heavy and light chain could also have been employed.

A nucleotide sequence encoding the recombinant heavy chain (SEQ ID NO: 9) and a nucleotide sequence encoding the light chain (SEQ ID NO: 10) was codon optimized for mammalian cell expression and cloned into the pTT5 vector using standard methods. Low endotoxin, giga-prep scale production of the expression plasmid encoding the sequence of SEQ ID NO: 9 and the expression plasmid encoding the sequence of SEQ ID NO: 10 resulted in 7.0 mg of each plasmid DNA (each, a vector). CHO-3E7 and HEK-293-6E cells were then each transfected with these two plasmids in a manner summarized below.

i. CHO-3E7

Four, 1 L cultures of CHO-3E7 cells (initial density of $1.9 \times 10^6$ cells/mL) in 2 L shake flasks were transfected with 1 mg total (1:1 ratio HC:LC) of plasmid DNA/L culture using PolyPlus linear Q-PEI at a 1:4 (w/v) DNA:PEI ratio. Culture parameters were monitored using a CedexXS (days 0-1) or a Vi-Cell XR (days 2-8) for density and viability. The culture media was F17 supplemented with 0.1% Pluronic F-68, 4 mM GlutaMAX. Cells were maintained at a density between $0.5\text{-}5 \times 10^6$ cells/mL in shake flasks. The flasks were incubated at 37° C. in a humidified 5% $CO_2$ environment with shaking at 135 rpm. Cultures were harvested 8 days post-transfection via centrifugation for 5 minutes at 1000×g. The conditioned culture supernatant was clarified by centrifugation for 30 minutes at 9300×g.

Fab-alpha-amylase was purified from the CHO-3E7 cells using a CaptureSelect IgG-CH1 affinity matrix (Life Technologies, #194320001). The CaptureSelect IgG-CH1 affinity resin (bed volume of 5 mL) was equilibrated in Buffer A (1×PBS (2.7 mM KCl, 1.7 mM $KH_2PO_4$, 136 mM NaCl, 10.1 mM $Na_2HPO_4$), pH 7.2 (23° C.)). Fab-alpha-amylase from 4 L of exhausted supernatant was batch bound with the CaptureSelect IgG-CH1 affinity resin at 4° C. overnight with stirring. The resin was collected in a 2.5 cm diameter Econo-column and washed with approximately 15 column volumes (CV) of Buffer A, 15 CV of Buffer B (1×PBS, 500 mM NaCl, pH 7.2 (23° C.)) and 15 CV Buffer A. The resin-bound Fab-alpha-amylase was eluted with ~4 CV of Buffer C (30 mM NaOAc, pH 3.5-3.6 (23° C.)) followed by ~4 CV of Buffer D (100 mM Glycine, pH 2.7 (23° C.)) collecting the protein in 2 mL fractions diluted in ⅒th volume Buffer E (3 M NaAcetate, ~pH 9.0 (23° C.)) to neutralize. To minimize the elution volume, elution was paused for several minutes between each fraction collected. Fractions were analyzed by A280 prior to pooling fractions 6-12 and 1-11 from the Buffer C and Buffer D elutions, respectively. The combined CaptureSelect IgG-CH1 affinity pool (50 mL) was dialyzed against 3×1 L of dialysis buffer (20 mM Histidine, 150 mM NaCl, pH 6.5 (23° C.)) at 4° C. The dialyzed pool was concentrated to ~10 mg/mL using a VivaSpin 20 (10K MWCO, PES membrane) centrifugal device prior to final analysis and storage at −80° C. Select fractions were analyzed by SDS-PAGE and by size exclusion chromatography, where it was confirmed that the Fab-alpha-amylase was being produced and successfully purified (data not shown).

ii. HEK-293-6E Cells

Twenty, 1 L cultures of 293-6E cells (initial density of $2.6 \times 10^6$ cells/mL) in 2 L shake flasks were transfected with 1 mg total (1:1 ratio HC:LC) of plasmid DNA/L culture using PolyPlus linear Q-PEI at a 1:1.5 (w/v) DNA:PEI ratio. Culture parameters were monitored using a ViCell XR for density and viability. The culture media was F17 supplemented with 0.1% Pluronic F-68, 4 mM GlutaMAX, 25 μg/mL G418. Cells were maintained at a density between $0.5\text{-}5 \times 10^6$ cells/mL in shake flasks. The flasks were incubated at 37° C. in a humidified 5% $CO_2$ environment with shaking at 135 rpm. Cultures were harvested 6 days post-transfection via centrifugation for 5 minutes at 1000×g. The conditioned culture supernatant was clarified by centrifugation for 30 minutes at 9300×g.

Fab-alpha-amylase was purified from the HEK-293-6E cells using a CaptureSelect IgG-CH1 affinity matrix (Life Technologies, #194320001). The CaptureSelect IgG-CH1 affinity resin was equilibrated in buffer A (1×PBS (2.7 mM KCl, 1.7 mM $KH_2PO_4$, 136 mM NaCl, 10.1 mM $Na_2HPO_4$), pH 7.2 (23° C.)). Fab-alpha-amylase from 20 L of exhausted supernatant was batch bound with the CaptureSelect IgG-CH1 affinity resin (40 mL bed volume) at 4° C. overnight with stirring. The resin was collected in a 5 cm diameter Econo-column and washed with approximately 15 column volumes (CV) of Buffer A, 15 CV of Buffer B (1×PBS, 500 mM NaCl, pH 7.2 (23° C.)) and 15 CV buffer A. The resin-bound fusion protein was eluted with ~4 CV of Buffer C (30 mM NaOAc, pH 3.5-3.6 (23° C.)) followed by ~4 CV of Buffer D (100 mM Glycine, pH 2.7 (23° C.)) collecting the protein in 10 mL fractions diluted in ⅒th volume Buffer E (3M NaAcetate, ~pH 9.0 (23° C.)) to neutralize. To minimize the elution volume, elution was paused for several minutes between each fraction collected. Fractions were analyzed by $A_{280}$ prior to pooling fractions 7-25. Select fractions were analyzed by SDS PAGE. Fab-alpha-amylase remained in the non-bound pool from the first affinity chromatography pass. The above procedure was repeated to capture remaining Fab-alpha-amylase. The affinity pools were combined prior to dialysis.

The combined CaptureSelect IgG-CH1 affinity pool (250 mL) was dialyzed against 3×4 L of dialysis buffer (20 mM Histidine, 150 mM NaCl, pH 6.5 (23° C.)) at 4° C. The dialyzed pool was concentrated to ~10 mg/mL using a VivaCell 100 (10K MWCO, PES membrane) centrifugal device prior to final analysis and storage at −80° C. Select fractions were analyzed by SDS-PAGE and by size exclusion chromatography, where it was confirmed that the Fab-alpha-amylase was being produced and successfully purified (data not shown).

In alternative embodiments, a protein comprising a full-length humanized 3E10 antibody and the alpha-amylase protein may be generated. Other chimeric proteins of the disclosure may be, for example, similarly made, and any such proteins may be used in any of the methods described herein.

B. Fab-Alpha-Amylase in a Cell-Free Activity Assay

The ability of Fab-alpha-amylase to digest glycogen was assessed in a cell-free assay. Glucose standards were prepared by dilution in water from 1 mg/mL glucose from the Glucose Oxidase kit (Sigma GAGO20-1KT): 0.08 mg/mL, 0.06 mg/mL, 0.04 mg/mL, 0.02 mg/mL, 0.01 mg/mL, 0.005 mg/mL (0.1 mg/mL=555.1 µM). Twenty mL of citrate/phosphate buffers from pH 3.5-7.0 were prepared by adding 0.1 M citric acid and 0.2 M sodium phosphate dibasic in the amounts indicated in Table 1. The buffers were spiked in 10% Tween-80 to 0.02% final, and pH was verified with a pH meter. The 0.1M sodium acetate pH 4.3+0.02% tween-80 was also prepared.

TABLE 1

| pH | mL 0.1M Citric Acid | mL 0.2M NaPO4 Dibasic |
|---|---|---|
| 3.5 | 6.04 | 13.96 |
| 4 | 7.72 | 12.28 |
| 4.3 | 8.49 | 11.51 |
| 4.5 | 9 | 11 |
| 5 | 10.28 | 9.72 |
| 5.5 | 11.36 | 8.64 |
| 6 | 12.84 | 7.16 |
| 6.5 | 14.2 | 5.8 |
| 7 | 17.44 | 2.56 |

Ten mg/mL glycogen was then prepared in each buffer solution to be tested. The Fab-alpha-amylase was diluted to 1 mg/mL in reaction buffer, and 1.8 µL of 1 mg/mL Fab-alpha-amylase was then added to 178.2 µL glycogen solution in a 500λ, vial (10 µg/mL final Fab-alpha-amylase concentration). The samples were mixed well and incubated at ambient temperature for 1 hour. Glycogen solution was also retained as a negative control. The digestion was terminated by heating the samples at 95° C. for 10 minutes. The Fab-alpha-amylase negative glycogen samples were heated as a negative control/blank sample. The glucose standards and digested glycogen test samples (40 µL/well) were then pipetted into 96 well plate in triplicate, and 80 µL Glucose Oxidase kit Reagent Mix (Sigma GAGO20-1KT; prepared as described in kit) was added to each well at room temperature with a multi-channel pipette, mixed well and incubated at 37° C. for 30 minutes. The reaction was terminated by adding 80 µL 12 N sulfuric acid with multi-channel pipette and mixing well. The plate was then read at 540 nm. No meaningful glycogen digestion was observed in the negative control samples. By comparison, glycogen digestion was observed in samples having the Fab-alpha-amylase protein, with the most robust activity observed at slightly acidic pHs. Representative results from test samples are shown below in Table 2.

TABLE 2

| pH | Specific Activity (µM/min/mg) |
|---|---|
| 5.5 | 753.5 |
| 6.0 | 689.4 |
| 6.5 | 562.3 |
| 7.0 | 435.1 |
| 7.5 | 390.2 |

The Fab-alpha-amylase protein was also found to be inactive at a pH of 4.3 (Data Not Shown).

In an additional or alternative experiment, polyglucosan bodies are isolated from a Lafora Disease animal model (e.g., the mouse model of Ganesh et al., 2002, Hum Mol Genet, 11:1251-1262) in a manner similar to that described in Zeng et al., 2012, FEBS J, 279(14):2467-78. Briefly, forebrain cortical neurons are microdissected from the brains of postnatal day 2 Epm2a wildtype or knockout mice into Neurobasal medium in a manner similar to that described in Wang et al., 2013, Mol Neurobiol, 48(1):49-61. Polyglucosan is then isolated in a manner similar to that described in Wang et al. Purified Fab-Alpha-Amylase fusion proteins are incubated with the isolated polyglucosan at various doses and for various timepoints, and the ability of the Fab-alpha-amylase to digest the polyglucosan is monitored.

C. Fab-Alpha-Amylase in Cell Culture

The efficacy of the Fab-alpha-amylase proteins on reducing polyglucosan levels in a primary neuron cell culture is tested in a manner similar to that described in Wang et al. (also see cell isolation protocol described above). Alternatively, N2A cells may be used in which a Lafora Disease phenotype is mimicked by treating these cells with the ER stressor thapsigargin in a manner similar to that described in Wang et al. The primary neuron cells or ER-stressed N2A cells (or control unstressed N2A cells) are then administered (or not) the Fab-alpha-amylase proteins, and the effect of the proteins on polyglucosan levels is monitored by PAS staining. A reduction in PAS staining in the protein treated cells is consistent with the polyglucosan being cleared from the cells by the chimeric polypeptides. In some embodiments, the effect of Fab-alpha-amylase on glycogen levels is tested on primary cells from a GSDIII and/or GSDIV human patient or animal model, or in an animal model.

In some embodiments, the effect of the Fab-alpha-amylase on glycogen levels is tested in a hypoxia cell model. In particular embodiments, the hypoxia tumor cell model is the same or similar to the one described in Pelletier et al., Frontiers in Oncology, 2(18):1-9, where it was shown that hyopoxia induces glycogen accumulation in certain cell types. Briefly, non-cancerous cells (e.g., Chinese hamser lung fibroblasts (CCL39) or mouse embryonic fibroblasts (MEF)) and/or cancerous cells (e.g., LS174 or BE colon carcinoma cells) are cultured at normoxic or hypoxic (1% $O_2$) conditions for 96 hours in the presence or absence of the Fab-alpha-amylase. Glycogen levels are assessed by electron microscopy and/or Periodic Acid Schiff staining. A reduction in glycogen levels in the Fab-alpha-amylase treated hypoxic cells as compared to the untreated hypoxic cells is assessed.

Figure 2:
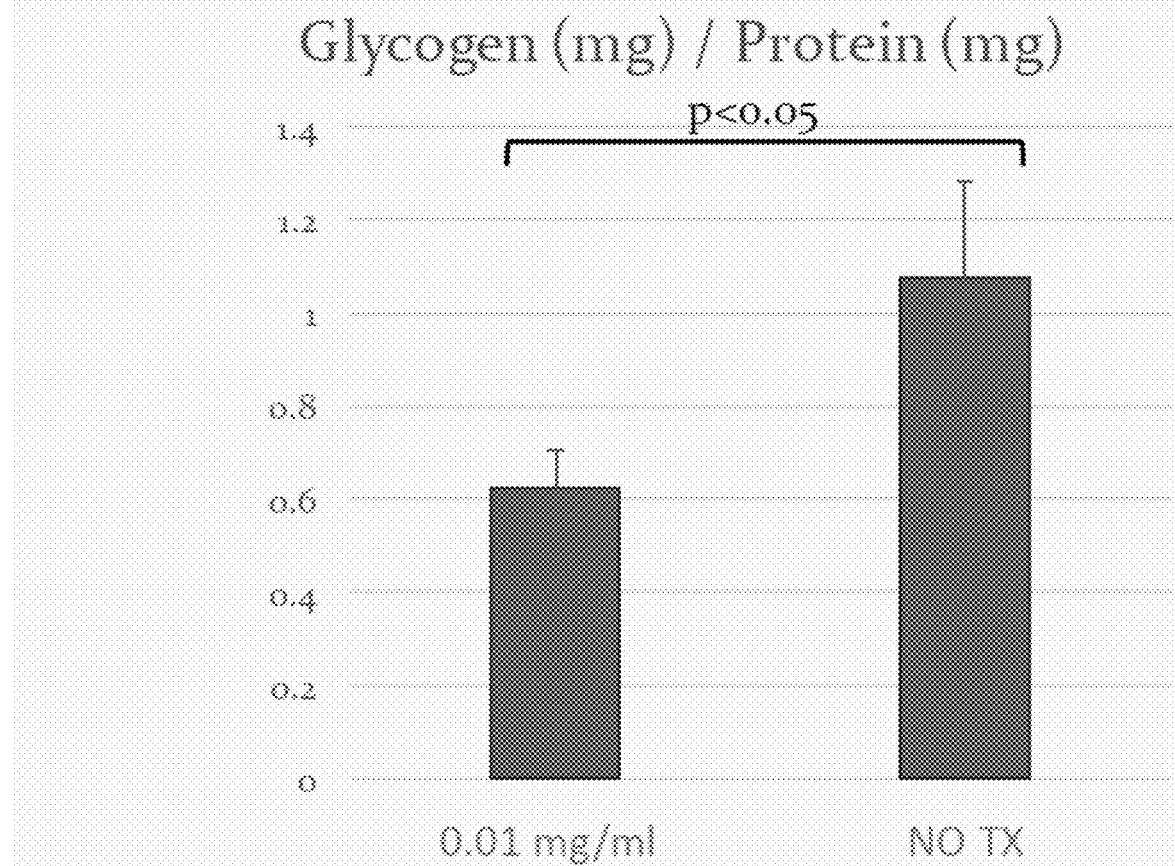
FIG. 2 is a graph demonstrating glycogen reduction in ENT2+C2C12 myotubes.

The efficacy of Fab-amylase on reducing polyglucosan levels in ENT2+C2C12 myotubes is tested. The dose dependent uptake of Fab-amylase in ENT2+C2C12 myotubes is shown in FIG. 1. A comparison of −Fab-amylase and +Fab-amylase at 0.01 mg/ml and 0.1 mg/ml is provided. The reduction of glycogen in ENT2+C2C12 myotubes by Fab-amylase is demonstrated by comparing glycogen (mg)/protein (mg) levels for non-transfected C2C12 myotubes to treated C2C12 myotubes (FIG. 2). Treated C2C12 myotubes are prepared by transfecting C2C12 myotubes with PTG and then treating the transfected myotubes with 0.01 mg/ml Fab-Amylase in the media after 24 hours.

D. Effect of Fab-Amylase on Lafora Bodies

Lafora Disease may be characterized by the accumulation of glycogen-filled inclusion bodies (also referred to herein as Lafora bodies or polyglucosan bodies) within the cytoplasm of the cells in the brain, heart, liver, muscle and skin.

i. Purification of Inclusion Bodies

Figures 3A, 3B, 3C, 3D:
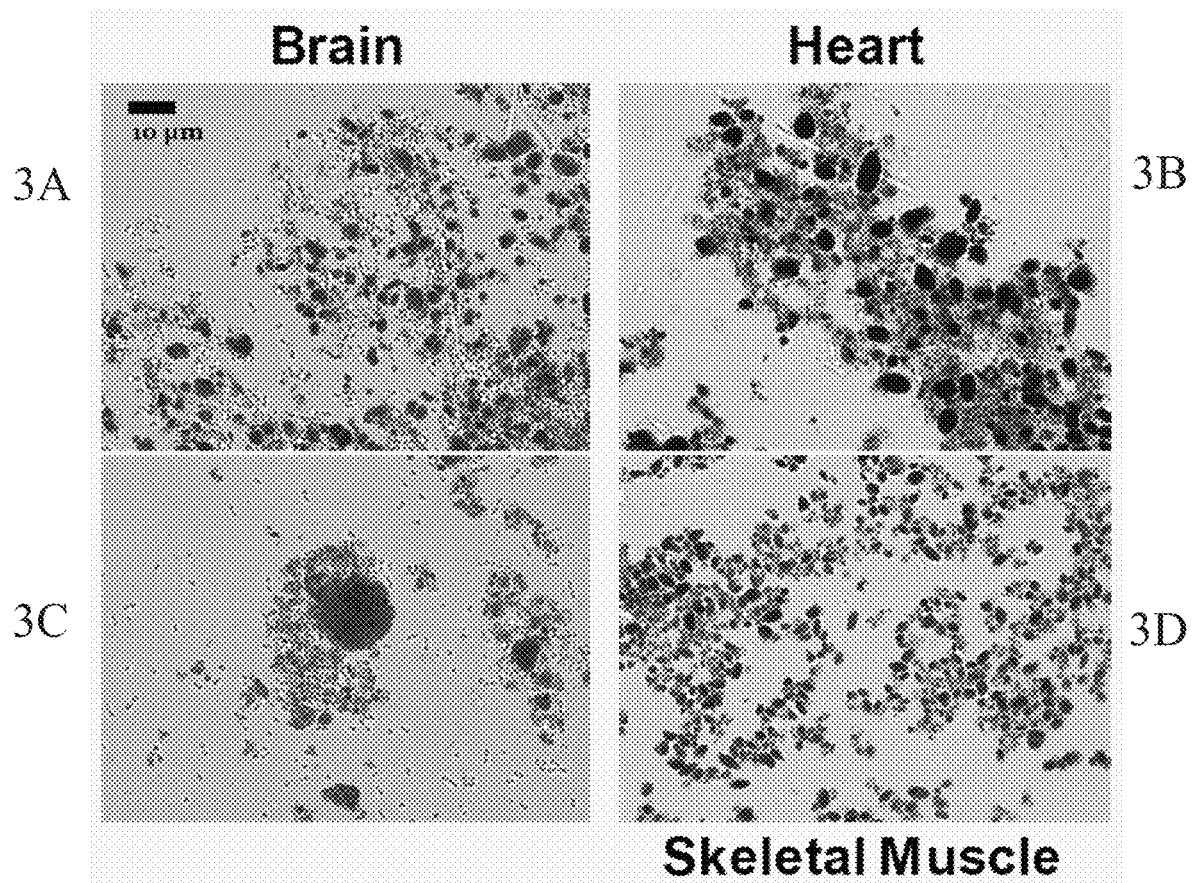
FIGS. 3A-3F summarize the results of a Lafora body purification scheme. The scheme includes (1) homogenizing tissue, resuspending and centrifuging; (2) digesting overnight with Proteinase K; (3) filtering; and (4) washing with SDS and buffer.
Figure 3E:
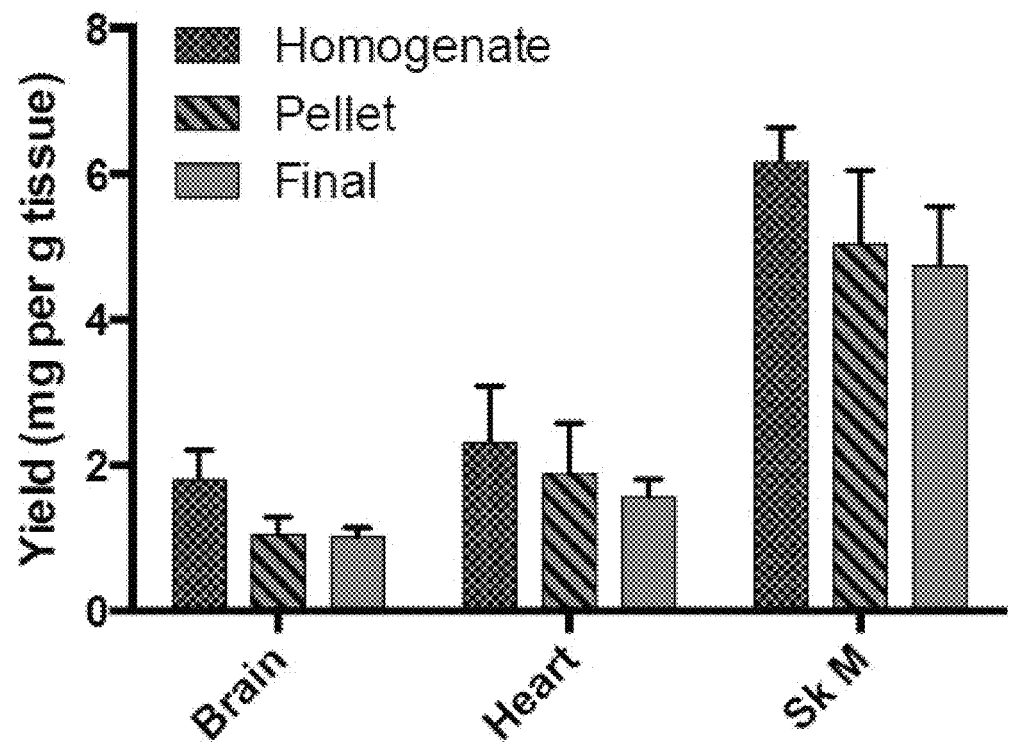
Figure 3F:

Inclusion bodies can be purified in a manner similar to that described in Yokoi et al., Arch Neurol, 19(1): 15-33. Inclusion bodies may also be purified by utilizing an improved purification scheme that involves four steps: (1) homogenizing the tissue, resuspending the mixture and centrifuging; (2) digesting overnight with Proteinase K; (3) filtering; and (4) washing with SDS and buffer. Samples from the homogenate, pellet and final sample may be assessed for yield (e.g., percentage of Lafora bodies successfully purified/isolated from the tissue lysate). The improved purification scheme was utilized on tissue samples obtained from the brain (FIG. 3A and FIG. 3C), heart (FIG. 3B), and skeletal muscle (FIG. 3D) of a Lafora knock out mouse. The samples demonstrated that there are some apparent visual similarities and differences between isolated Lafora bodies from a Lafora knock out mouse (e.g., laforin$^{-/-}$). Even within the brain there is evidence of heterogeneity with larger aggregated Lafora bodies (FIG. 3C). The yield (mg per g tissue) from the homogenate, pellet and final sample obtained from the brain, heart, and skeletal muscle was measured (FIG. 3E) showing a 50-70% yield of purified inclusion bodies in the skeletal muscle. In addition, the yield (mg per g tissue) of iodine and total glucose is measured from the brain, heart, and skeletal muscle samples (FIG. 3F).

ii. Assessment of Purified Inclusion Bodies

Figures 4A, 4B:
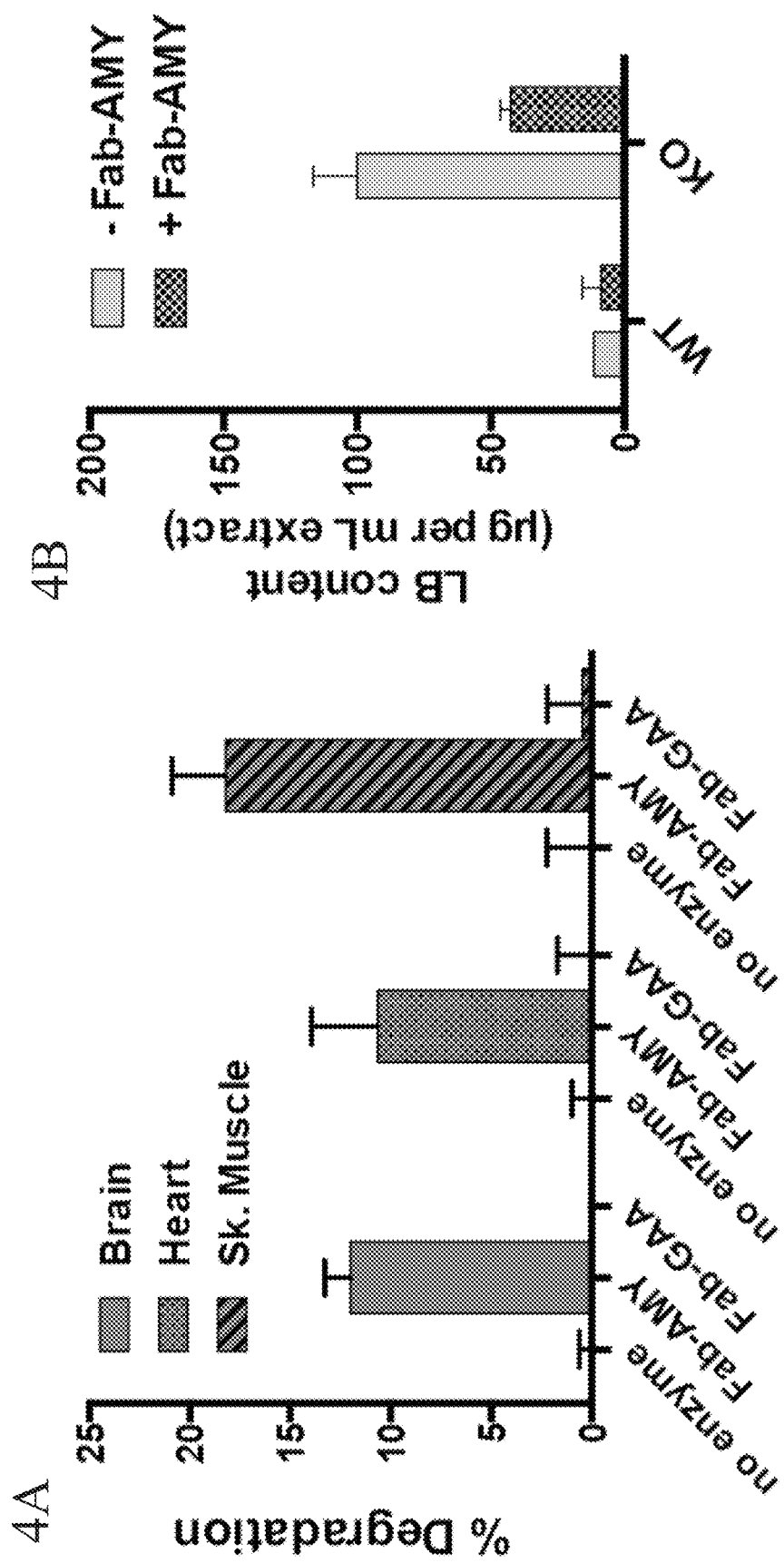
FIGS. 4A-4B show purified Lafora bodies can be degraded by Fab-amylase but not by Fab-glucosidase.

The efficacy of Fab-fusions can be assessed using the purified inclusion bodies. A degradation assay is performed applying Fab-amylase and Fab-glucosidase to purified inclusion bodies isolated from tissue of the brain, heart, and skeletal muscle of Lafora knock out mice. The results show that Fab-amylase, and not Fab-glucosidase, degrades the purified inclusion bodies (FIG. 4A). The effect of Fab-amylase on inclusion bodies is further assessed by measuring the inclusion body content (µg per mL extract) of samples obtained from wild type mice and knock out mice treated with −Fab-amylase and +Fab-amylase ex vivo (FIG. 4B).

E. Fab-Alpha-Amylase Activity

Figure 5A:
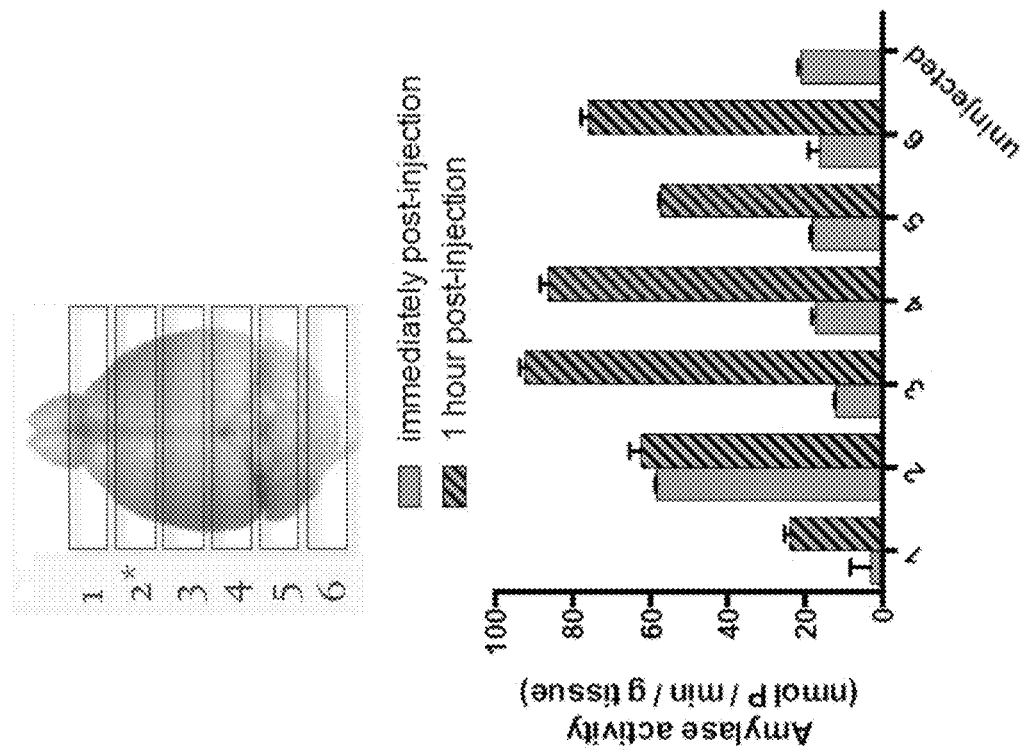
FIGS. 5A-5B demonstrate injected Fab-amylase is active in the muscle and brain.
Figure 5B:
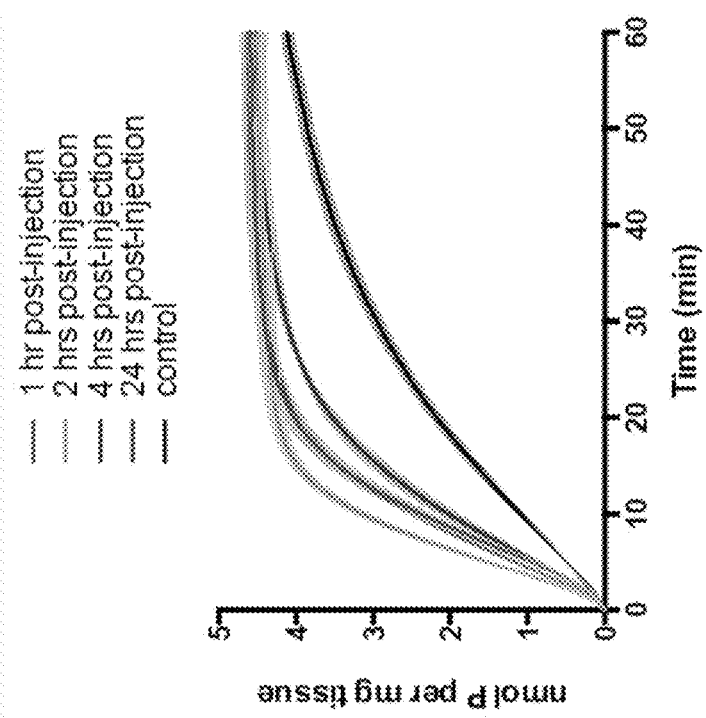

The activity of Fab-amylase can be measured using an amylase activity colorimetric assay kit (BioVision). The methods for using the assay kit are optimized by identifying a choice of time points to measure the sample at OD 405 nm and selecting the optimum time point. Fab-amylase activity (nmol P per mg tissue) is measured in the muscle at various time points post injection, including at 1 hour post-injection, 2 hours post-injection, 4 hours post-injection, and 24 hours post-injection (FIG. 5A). Amylase activity (nmol P/min/g tissue) is also measured for various sections of the brain (as identified in upper panel of FIG. 5B) immediately post-injection and 1 hour post-injection (FIG. 5B, lower panel).

F. Fab-Alpha-Amylase In Vivo

Mice engineered to be deficient in malin display a phenotype similar to that observed in human cases of Lafora Disease. Specifically, malin$^{-/-}$ mice presented in an age-dependent manner neurodegeneration, increased synaptic excitability, and propensity to suffer myoclonic seizures. Valles-Ortega et al., 2011, EMBO Mol Med, 3(11):667-681. In addition, these mice accumulated glycogen-filled inclusion bodies that were most abundant in the hippocampus and cerebellum, but that were also found in skeletal and cardiac muscle cells. Valles-Ortega et al. Glycogen was also found to be less branched in the cells of malin$^{-/-}$ mice as compared to glycogen observed in the cells of healthy control mice. Valles-Ortega et al. An increased level of glycogen hyperphosphorylation has also been described in this mouse model. Turnbull et al., 2010, Ann Neurol, 68(6):925-33. Alternative mouse models that could be used in the in vivo experiments described herein include the laforin$^{-/-}$ mouse model described in Ganesh et al., 2002, Hum Mol Genet, 11(11):1251-62.

i. Selection of dose of Fab-Alpha-Amylase

The evaluation dose of the Fab-alpha-amylase delivered to the Lafora Disease mice is determined empirically. To minimize the confounding effect of a neutralizing immune response to Fab-alpha-amylase and to maximize the ability to demonstrate a therapeutic effect, two high doses of 5 mg/kg of Fab-alpha-amylase are delivered in one week, followed by assessment of changes in disease endpoints. The development of anti-Fab-alpha-amylase antibodies is also monitored. Following establishment that intravenous Fab-alpha-amylase results in an improvement in aberrant glycogen storage in mice brain, heart, diaphragm or liver, subsequent in vivo assessments in other models (e.g., primates) are initiated, followed by assessment of changes in glycogen clearance, as determined by immunohistochemistry (e.g., PAS staining).

ii. Materials and Methods a) Injection of Chemically and Genetically Conjugated Fab-Alpha-Amylase Fab-alpha-amylase is formulated and diluted in a buffer that is consistent with intravenous injection (e.g. sterile saline solution or a buffered solution of 50 mM Tris-HCl, pH 7.4, 0.15 M NaCl). The amount of Fab-alpha-amylase given to each mouse is calculated as follows: dose (mg/kg)×mouse weight (kg)×stock concentration (mg/ml)=volume (ml) of stock per mouse, q.s. to 100 ul with vehicle.

b) Blood Collection

Blood is collected by cardiac puncture at the time that animals are sacrificed for tissue dissection. Serum is removed and frozen at −80° C. To minimize the effects of thawing and handling all analysis of Fab-alpha-amylase circulating in the blood is performed on the same day.

c) Tissue Collection and Preparation

Sampled tissues are divided for immunoblot, glycogen analysis, formalin-fixed paraffin-embedded tissue blocks and frozen sections in OCT. Heart, liver, lung, spleen, kidneys, quadriceps, EDL, soleus, diaphragm, brain, and biceps tissue (50-100 mg) are subdivided and frozen in plastic tubes for further processing for immunoblot and glycogen analysis. Additional samples of heart, liver, lung, spleen, kidneys, quadriceps, EDL, soleus, diaphragm, brain and biceps are subdivided, frozen in OCT tissue sectioning medium, or fixed in 3% glutaraldehyde formaldehyde fixation for 24 to 48 hours at 4° C. and embedded in Epon resin, or fixed in 10% NBF and processed into paraffin blocks. Some samples are homogenized in 30% KOH for 15 min, and glycogen levels are determined using an amyloglucosidase-based assay described in Valles-Ortega et al. In addition, glycogen branching are assessed in the homogenized samples using the methods described in Valles-Ortega et al. A reduction in glycogen accumulation and an increase in glycogen branching in samples from mice treated with Fab-alpha-amylase as compared to untreated control mice is indicative that the chimeric polypeptides are capable of clearing glycogen and improving glycogen branching in the cells of the mice.

d) Histological Evaluation

Epon-resin embedded samples are cut at 1 µm and stained with PAS-Richardson's stain for glycogen staining. Reduced levels of glycogen accumulation in tissues (e.g., muscle or liver) of Lafora Disease mice treated with Fab-alpha-amylase as compared to control-treated Lafora Disease mice is indicative that the Fab-alpha-amylase is capable of reducing glycogen levels in vivo.

e) Immunofluorescence

Exogenously delivered Fab-alpha-amylase are detected using a polyclonal or monoclonal anti-alpha-amylase antibody. Ten micrometer frozen sections are cut and placed on Superfrost Plus microscope slides.

f) Immunoblot

Immunoblotting is used to detect 3E10 and alpha-amylase immune reactive material in Fab-alpha-amylase treated muscles (e.g., diaphragm), heart and brain tissues. Protein isolation and immunoblot detection of 3E10 and alpha-amylase are performed according to routine immunoblot methods. Alpha-amylase is detected with an antibody specific for this protein. Antibody detection of blotted proteins use NBT/BCIP as a substrate. Controls include vehicle and treated Lafora Disease mice and vehicle and treated homozygous wildtype mice.

g) Analysis of Circulating Fab-Alpha-Amylase

An ELISA specific to human Fab-alpha-amylase is developed and validated using available anti-human amylase antibodies (or anti-CH1 antibodies to detect the constant heavy chain of the Fab portion of the Fab-alpha-amylase) and horseradish peroxidase conjugated anti-mouse secondary antibody (Jackson Immunoresearch). Recombinant Fab-alpha-amylase is diluted and used to generate a standard curve. Levels of Fab-alpha-amylase are determined from dilutions of serum (normalized to ng/ml of serum) or tissue extracts (normalized to ng/mg of tissue). Controls include vehicle and treated wildtype and Lafora Disease mice.

h) Monitoring of anti-Fab-Alpha-Amylase Antibody Responses

Purified Fab-alpha-amylase used to inject Lafora Disease mice are plated onto high-binding 96 well ELISA plates at 1 ug/ml in coating buffer (Pierce Biotech), allowed to coat overnight, blocked for 30 minutes in 1% nonfat drymilk (Biorad) in TBS, and rinsed three times in TBS. Two-fold dilutions of sera from vehicle and Fab-alpha-amylase injected animals are loaded into wells, allowed to incubate for 30 minutes at 37° C., washed three times, incubated with horseradish peroxidase (HRP)-conjugated rabbit anti-mouse IgA, IgG, and IgM, allowed to incubate for 30 minutes at 37° C., and washed three times. Mouse anti-Fab-alpha-amylase antibodies are detected with TMB liquid substrate and read at 405 nm in ELISA plate reader. A polyclonal anti-alpha-amylase antibody, followed by HRP-conjugated goat anti-rabbit serve as the positive control antibody reaction. Any absorbance at 405 nm greater than that of vehicle treated Lafora mice constitutes a positive anti-Fab-alpha-amylase antibody response. Controls include vehicle and treated wildtype mice and Lafora mice.

i) Tissue Glycogen Analysis

Tissue glycogen content is assayed using the protocol described in Akman (2011). Samples of frozen muscle (e.g., diaphragm or cardiac muscle), brain and liver tissue (~30-60 mg) are boiled in 200 µl of 30% (wt/vol) KOH for 30 min with occasional shaking. After cooling, 67 µl of 0.25 m Na2SO4 and 535 µl of ethanol is added. Next, samples are centrifuged at 14500 g for 20 min at 4° C. to collect glycogen. The glycogen pellet is suspended in water (100 µl), 200 µl of ethanol are added and centrifugation as described above is used to harvest glycogen. This ethanol precipitation step is repeated, and the glycogen pellet is dried in a Speed-Vac. Dried glycogen pellets are suspended in 100 µl of amyloglucosidase [0.3 mg/ml in 0.2 m sodium acetate (pH 4.8)] and incubated at 37° C. for 3 h to digest glycogen. To determine the glucose concentration in the samples, an aliquot (5 µl) of digested glycogen is added to 95 µl of a solution containing 0.3 m triethanolamine (pH 7.6), 0.4 mm MgCl2, 0.9 mm NADP, 1 mm ATP and 0.1 µg of glucose-6-phosphate dehydrogenase/ml. The absorbance at 340 nm is read before and after the addition of 0.1 µg of hexokinase.

j) Seizure Assessment

The malin$^{-/-}$ mice described by Valles-Ortega et al. were generated in the C57BL6 strain of mice, which are normally resistant to seizures. However, while administration of kainate did not induce any seizures in wildtype C57BL6 mice, malin$^{-/-}$ mice treated with kainate displayed clonic hippocampal seizures. Valles-Ortega et al. Malin$^{-/-}$ mice are treated with kainate and with or without Fab-alpha-amylase. If the mice treated with kainate and Fab-alpha-amylase display reduced seizures as compared to malin$^{-/-}$ mice treated with kainate but not with any chimeric polypeptides, this is indicative that the chimeric polypeptides are effective in treating some of the neurological defects observed in the malin$^{-/-}$ mice.

k) Neurodegeneration Analysis

The total number of parvalbumin positive interneurons is assessed in the hippocampus of malin$^{-/-}$ mice treated with or without Fab-alpha-amylase. Valles-Ortega et al. If the hippocampi from mice treated with Fab-alpha-amylase display less parvalbumin-positive neurodegeneration than in the hippocampi from untreated mice, than this is indicative that the chimeric polypeptides are effective in reducing neurodegeneration in the malin$^{-/-}$ mice.

l) Statistical Analysis

Pairwise comparisons employs Student's t-test. Comparisons among multiple groups employ ANOVA. In both cases a p-value<0.05 is considered statistically significant.

iii. Assessment of Fab-Alpha-Amylase Upon Intramuscular Injection

The effect of intramuscular injections of Fab-amylase is assessed by comparing Fab-amylase treated mice with control mice. In the Fab-amylase treated mice, four 20 ul (10 mg/ml) intramuscular injections are administered into the Tibialis anterior (TA) muscle of the right leg over the course of two weeks, while PBS is injected into the left leg. In the control mice, PBS is injected into both the right and left legs of the mice. At the end of the two weeks, the mice were sacrificed and the Tibialis anterior muscles were embedded with OCT mounting media, flash frozen in liquid nitrogen cooled isobutane, and then later sectioned for Periodic acid-Schiff (PAS) staining.

Figure 6:
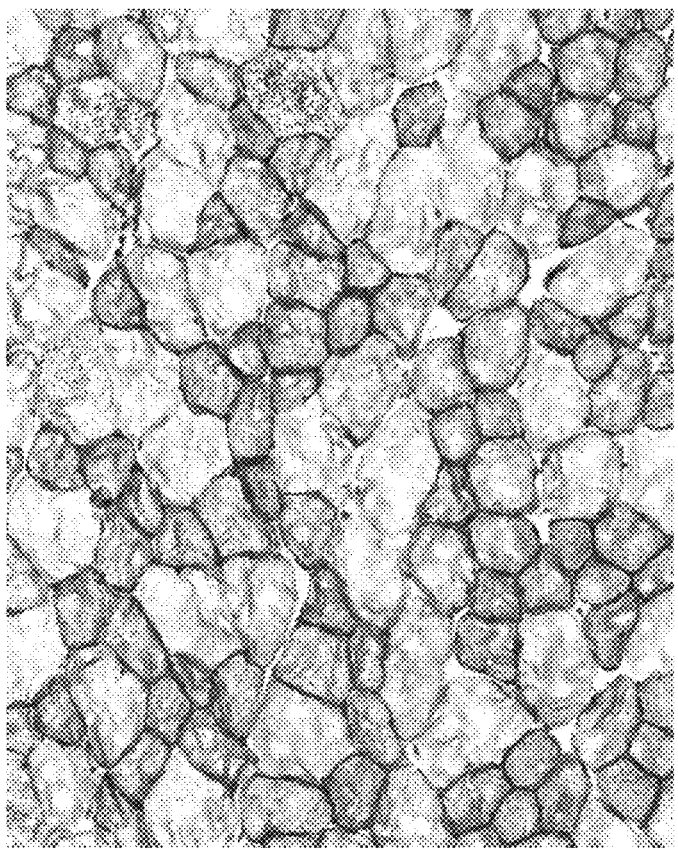
FIG. 6 shows Periodic acid-Schiff (PAS) staining of the Tibialis anterior (TA) muscle of an 8.5 month old female mouse injected with a vehicle (PBS) in the left leg (left panel) and Fab-Amylase in the right leg (right panel).
Figure 6:
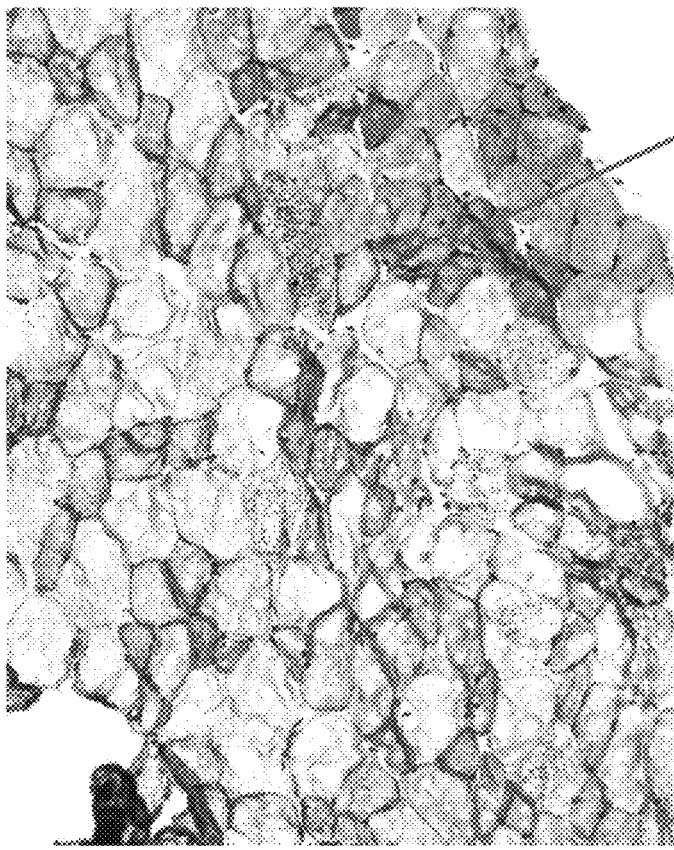
Figure 7:
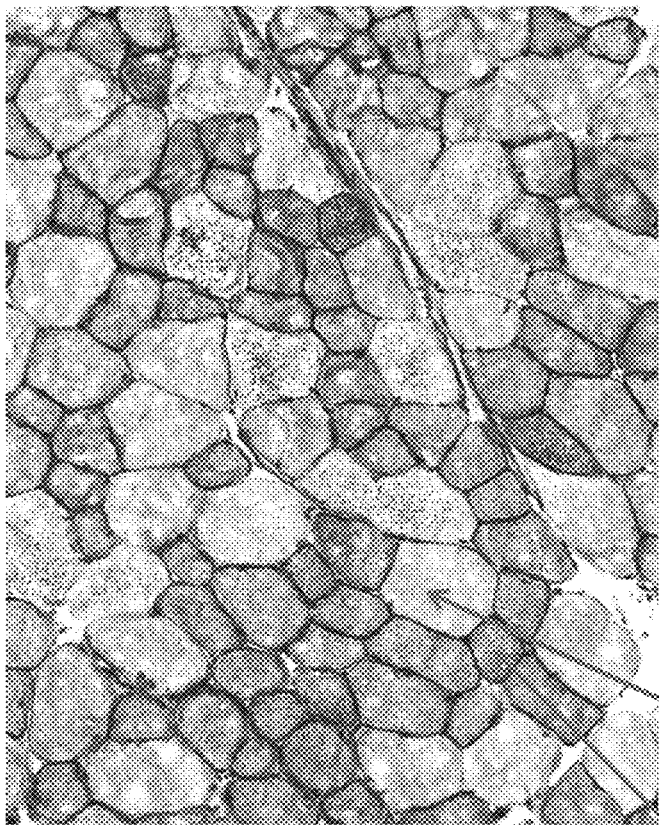
FIG. 7 shows Periodic acid-Schiff (PAS) staining of the Tibialis anterior (TA) muscle of an 8.5 month old female mouse injected with a vehicle (PBS) in the left leg (left panel) and Fab-Amylase in the right leg (right panel).
Figure 7:
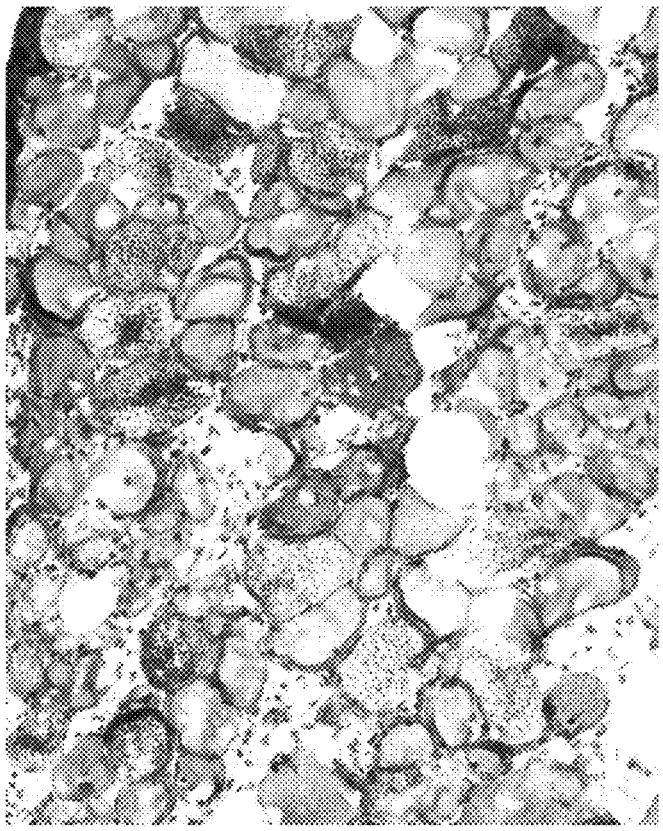
Figure 8:
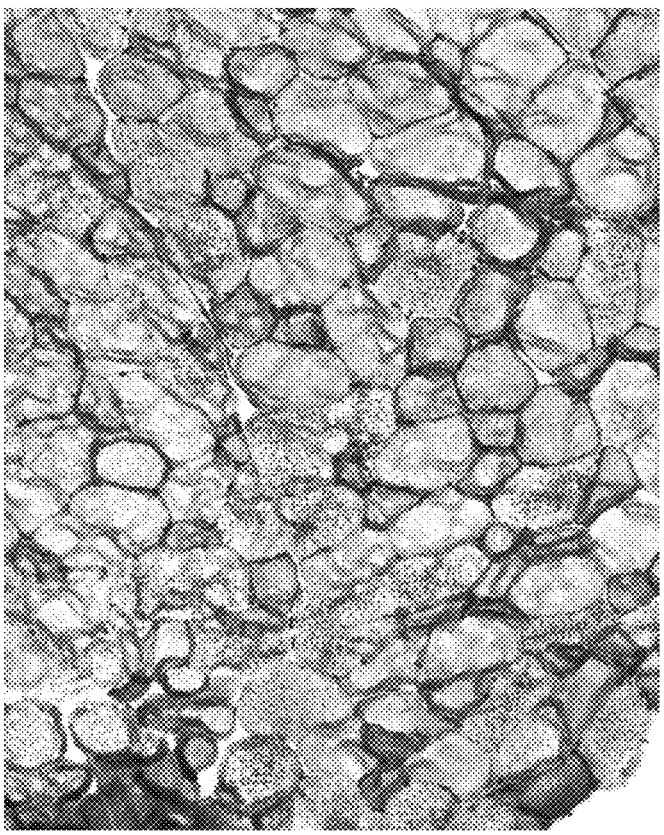
FIG. 8 shows Periodic acid-Schiff (PAS) staining of the Tibialis anterior (TA) muscle of an 8.5 month old female mouse injected with a vehicle (PBS) in the left leg (left panel) and a vehicle (PBS) in the right leg (right panel).
Figure 8:
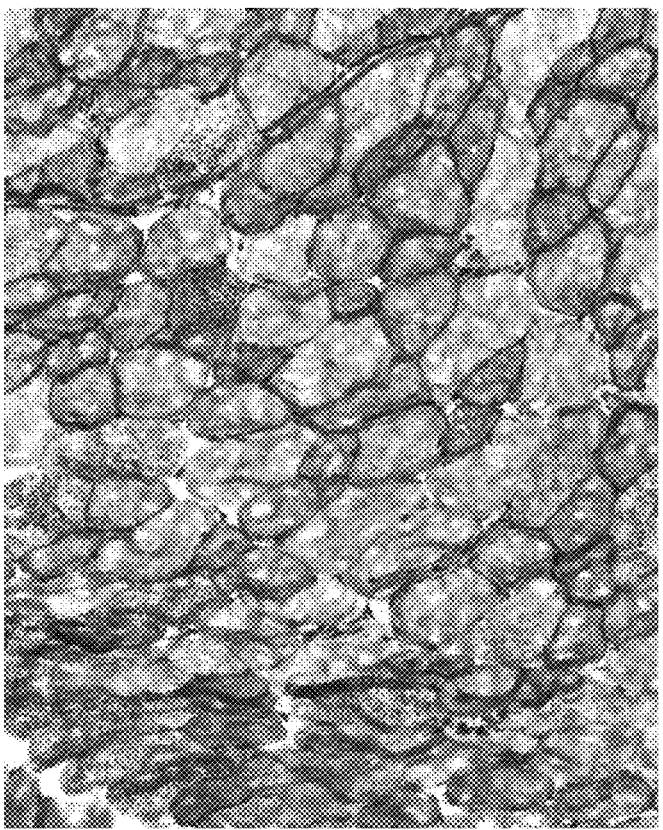
Figure 9:
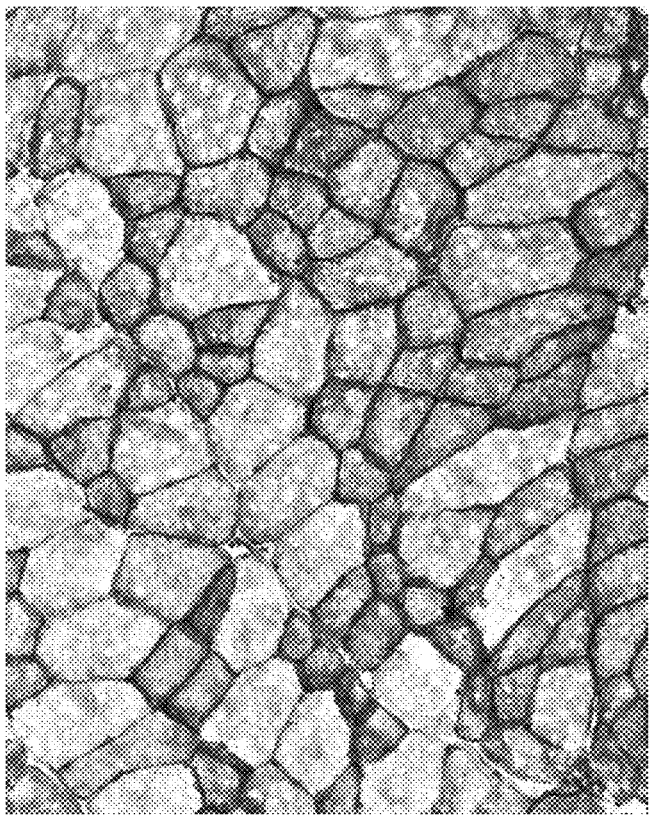
FIG. 9 shows Periodic acid-Schiff (PAS) staining of the Tibialis anterior (TA) muscle of a 4 month old female mouse injected with a vehicle (PBS) in the left leg (left panel) and Fab-Amylase in the right leg (right panel).
Figure 9:
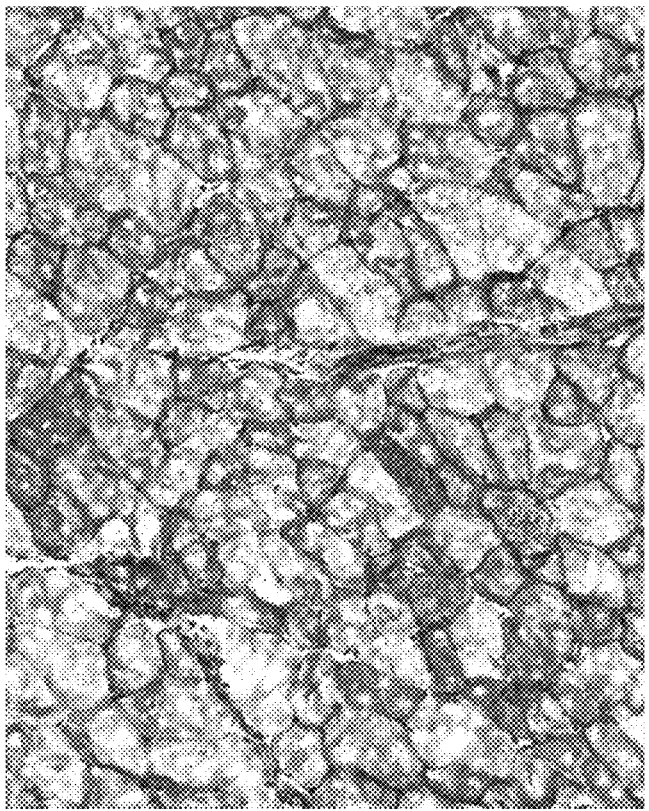

The mice that were treated with Fab-amylase showed a reduction in very strong instances of dark pink glycogen detection with PAS staining, as well as an improvement in muscle architecture (e.g., clear distinction between fast and slow muscle fibers). For example, as seen in FIG. 6, a treated 8.5 month old female mouse (specimen #8) demonstrates very dark pink staining in the left leg (PBS treated) (left panel) signifying over accumulated glycogen. In comparison, the Fab-amylase treated muscle does not show the same staining (right panel). A second treated 8.5 month old female mouse (specimen #7) exhibits similar results as seen in FIG. 7. The Fab-amylase treated muscle (right panel) also shows normal fiber differences between fast fibers (small, light purple) and slow fibers (larger, more clear), as compared to the PBS treated muscle (left panel). FIG. 9, which provides a comparison of PBS treated muscle (left panel) to Fab-amylase treated muscle (right panel) of a 4 month old female mouse (specimen #6), further supports these findings. An 8.5 month old female mouse (specimen #10) acts as a control (FIG. 8) with PBS treated muscles for both the left and right legs (left panel and right panel, respectively).

```
Exemplary Sequences
SEQ ID NO: 1--Alpha Amylase Polypeptide
Amino Acid Sequence (Genbank accession number
NP_000690)
QYSPNTQQGRTSIVHLFEWRWVDIALECERYLAPKGFGGVQVSPPNEN

VAIYNPFRPWWERYQPVSYKLCTRSGNEDEFRNMVTRCNNVGVRIYVD
```

AVINHMCGNAVSAGTSSTCGSYFNPGSRDFPAVPYSGWDFNDGKCKTG

SGDIENYNDATQVRDCRLTGLLDLALEKDYVRSKIAEYMNHLIDIGVA

GFRLDASKHMWPGDIKAILDKLHNLNSNWFPAGSKPFIYQEVIDLGGE

PIKSSDYFGNGRVTEFKYGAKLGTVIRKWNGEKMSYLKNWGEGWGFVP

SDRALVFVDNHDNQRGHGAGGASILTFWDARLYKMAVGFMLAHPYGFT

RVMSSYRWPRQFQNGNDVNDWVGPPNNNGVIKEVTINPDTTCGNDWVC

EHRWRQIRNMVIFRNVVDGQPFTNWYDNGSNQVAFGRGNRGFIVFNND

DWSFSLTLQTGLPAGTYCDVISGDKINGNCTGIKIYVSDDGKAHFSIS

NSAEDPFIAIHAESKL

SEQ ID NO: 2--Humanized Variable Heavy Chain
Amino Acid Sequence (VH3)
EVQLQESGGGVVQPGGSLRLSCAASGFTFSNYGMHWIRQAPGKGLEWV

SYISSGSSTIYYADSVKGRFTISRDNSKNTLYLQMNSLRSEDTAVYYC

ARRGLLLDYWGQGTLVTVSS

SEQ ID NO: 3--Humanized Variable Light Chain
Amino Acid Sequence (VL2)
DIQMTQSPSSLSASVGDRVTISCRASKSVSTSSYSYMHWYQQKPEKAP

KLLIKYASYLQSGVPSRFSGSGSGTDFTLTISSLQPEDVATYYCQHSR

EFPWTFGAGTKLELK

SEQ ID NO: 4--Heavy Chain Leader Amino Acid
Sequence
MEFGLSWLFLVAILKGVQC

SEQ ID NO: 5--Light Chain Leader Amino Acid
Sequence
MDMRVPAQLLGLLLLWLRGARC

SEQ ID NO: 6--Glycine-Serine Linker Amino
Acid Sequence
GGSGGGSGGGSGG

SEQ ID NO: 7--Humanized Heavy Chain Amino Acid
Sequence (including human IgG1 CH1 and truncated
hinge constant regions)
EVQLQESGGGVVQPGGSLRLSCAASGFTFSNYGMHWIRQAPGKGLEWV

SYISSGSSTIYYADSVKGRFTISRDNSKNTLYLQMNSLRSEDTAVYYC

ARRGLLLDYWGQGTLVTVSSASTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHT

SEQ ID NO: 8--Humanized Light Chain Amino Acid
Sequence (including human kappa light chain
region)
DIQMTQSPSSLSASVGDRVTISCRASKSVSTSSYSYMHWYQQKPEKAP

KLLIKYASYLQSGVPSRFSGSGSGTDFTLTISSLQPEDVATYYCQHSR

EFPWTFGAGTKLELKRTVAAPSVFIFPPSDEQLKSGTASVVCLLNNFY

PREAKVQWKVDNALQSGNSQESVTEQDSKDSTYSLSSTLTLSKADYEK

HKVYACEVTHQGLSSPVTKSFNRGEC

SEQ ID NO: 9--Heavy Chain + Alpha-Amylase
Fusion Protein Amino Acid Sequence (Including
Leader and Linker Sequences)
MEFGLSWLFLVAILKGVQCEVQLQESGGGVVQPGGSLRLSCAASGFTF

SNYGMHWIRQAPGKGLEWVSYISSGSSTIYYADSVKGRFTISRDNSKN

TLYLQMNSLRSEDTAVYYCARRGLLLDYWGQGTLVTVSSASTKGPSVF

PLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDK

THTGGSGGGSGGGSGGQYSPNTQQGRTSIVHLFEWRWVDIALECERYL

APKGFGGVQVSPPNENVAIYNPFRPWWERYQPVSYKLCTRSGNEDEFR

NMVTRCNNVGVRIYVDAVINHMCGNAVSAGTSSTCGSYFNPGSRDFPA

VPYSGWDFNDGKCKTGSDIENYNDATQVRDCRLTGLLDLALEKDYVR

SKIAEYMNHLIDIGVAGFRLDASKHMWPGDIKAILDKLHNLNSNWFPA

GSKPFIYQEVIDLGGEPIKSSDYFGNGRVTEFKYGAKLGTVIRKWNGE

KMSYLKNWGEGWGFVPSDRALVFVDNHDNQRGHGAGGASILTFWDARL

YKMAVGFMLAHPYGFTRVMSSYRWPRQFQNGNDVNDWVGPPNNNGVIK

EVTINPDTTCGNDWVCEHRWRQIRNMVIFRNVVDGQPFTNWYDNGSNQ

VAFGRGNRGFIVFNNDDWSFSLTLQTGLPAGTYCDVISGDKINGNCTG

IKIYVSDDGKAHFSISNSAEDPFIAIHAESKL

SEQ ID NO: 10--Light Chain + Leader Amino Acid
Sequence
MDMRVPAQLLGLLLLWLRGARCDIQMTQSPSSLSASVGDRVTISCRAS

KSVSTSSYSYMHWYQQKPEKAPKLLIKYASYLQSGVPSRFSGSGSGTD

FTLTISSLQPEDVATYYCQHSREFPWTFGAGTKLELKRTVAAPSVFIF

PPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

SEQ ID NO: 11--Heavy Chain IgG1 CH1 and
Truncated Hinge Constant Domain
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHT

SEQ ID NO: 12-Human Kappa Constant Domain of
Km3 Allotype
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC

SEQ ID NO: 13 = GS3 linker
GGGGSGGGGSGGGGS

SEQ ID NO: 14 = Linker
GSTSGSGKSSEGKG

SEQ ID NO: 15 = His tag
HHHHHHH

SEQ ID NO: 16 = c-Myc tag
EQKLISEEDL

SEQ ID NO: 17 = exemplary 3E10 Variable Heavy
Chain (V$_H$ having D31N substitution; see
examples)
EVQLVESGGGLVKPGGSRKLSCAASGFTFSNYGMHWVRQAPEKGLEWV

AYISSGSSTIYYADTVKGRFTISRDNAKNTLFLQMTSLRSEDTAMYYC

ARRGLLLDYWGQGTTLTVSS

SEQ ID NO: 18 = 3E10 Variable Light Chain (V_L)
DIVLTQSPASLAVSLGQRATISCRASKSVSTSSYSYMHWYQQKPGQPP
KLLIKYASYLESGVPARFSGSGSGTDFHLNIHPVEEEDAATYYCQHSR
EFPWTFGGGTKLELK SEQ ID NO: 19-heavy chain variable domain CDR1
of 3E10 VH (as that VH is defined with reference
to SEQ ID NO: 9), in accordance with Kabat
system
NYGMH SEQ ID NO: 20-heavy chain variable domain CDR2
of 3E10 VH (as that VH is defined with reference
to SEQ ID NO: 9), in accordance with Kabat
system
YISSGSSTIYYADTVKG SEQ ID NO: 21-heavy chain variable domain CDR3
of 3E10 VH (as that VH is defined with reference
to SEQ ID NO: 9), in accordance with Kabat
system
RGLLLDY SEQ ID NO: 22-light chain variable domain CDR1
of 3E10 VL (as that VL is defined with reference
to SEQ ID NO: 10), in accordance with Kabat
system
RASKSVSTSSYSYMH SEQ ID NO: 23-light chain variable domain CDR2
of 3E10 VL (as that VL is defined with reference
to SEQ ID NO: 10), in accordance with Kabat
system
YASYLES SEQ ID NO: 24-light chain variable domain CDR3
of 3E10 VL (as that VL is defined with reference
to SEQ ID NO: 10), in accordance with Kabat
system
QHSREFPWT

SEQ ID NO: 25
AGIH

SEQ ID NO: 26
SAGIH

SEQ ID NO: 27-heavy chain variable (V_H) domain
CDR1 of exemplary 3E10 molecule, in accordance
with CDRs as defined by the IMGT system
GFTFSNYG SEQ ID NO: 28-heavy chain variable (V_H) domain
CDR2 of exemplary 3E10 molecule, in accordance
with CDRs as defined by the IMGT system
ISSGSSTI SEQ ID NO: 29-heavy chain variable (V_H) domain
CDR3 of exemplary 3E10 molecule, in accordance
with CDRs as defined by the IMGT system
ARRGLLLDY SEQ ID NO: 30-light chain variable (V_L) domain
CDR1 of exemplary 3E10 molecule, in accordance
with CDRs as defined by the IMGT system
KSVSTSSYSY SEQ ID NO: 31-light chain variable (V_L) domain
CDR2 of exemplary 3E10 molecule, in accordance
with CDRs as defined by the IMGT system
YAS SEQ ID NO: 32-light chain variable (V_L) domain
CDR3 of exemplary 3E10 molecule, in accordance
with CDRs as defined by the IMGT system
QHSREFPWT SEQ ID NO: 33-amino acid sequence of humanized
3E10 heavy chain (hVH1)
EVQLVQSGGGLIQPGGSLRLSCAASGFTFSNYGMHWVRQAPGKGLEWV
SYISSGSSTIYYADSVKGRFTISRDNSKNTLYLQMNSLRAEDTAVYYC
ARRGLLLDYWGQGTTVTVSS SEQ ID NO: 34-amino acid sequence of humanized
3E10 heavy chain (hVH2)
EVQLVESGGGLIQPGGSLRLSCAASGFTFSNYGMHWVRQAPGKGLEWV
SYISSGSSTIYYADSVKGRFTISRDNSKNTLYLQMTSLRAEDTAVYYC
ARRGLLLDYWGQGTTLTVSS SEQ ID NO: 35-amino acid sequence of humanized
3E10 light chain (hVL1)
DIQMTQSPSSLSASVGDRVTITCRASKSVSTSSYSYLAWYQQKPEKAP
KLLIKYASYLQSGVPSRFSGSGSGTDFTLTISSLQPEDFATYYCQHSR
EFPWTFGAGTKLELK SEQ ID NO: 36-Human Pancreatic Alpha Amylase
Amino Acid Sequence (GenBank Accession No.:
NP_000690.1)
MKFFLLLFTIGFCWAQYSPNTQQGRTSIVHLFEWRWVDIALECERYLA
PKGFGGVQVSPPNENVAIYNPFRPWWERYQPVSYKLCTRSGNEDEFRN
MVTRCNNVGVRIYVDAVINHMCGNAVSAGTSSTCGSYFNPGSRDFPAV
PYSGWDFNDGKCKTGSGDIENYNDATQVRDCRLTGLLDLALEKDYVRS
KIAEYMNHLIDIGVAGFRLDASKHMWPGDIKAILDKLHNLNSNWFPAG
SKPFIYQEVIDLGGEPIKSSDYFGNGRVTEFKYGAKLGTVIRKWNGEK
MSYLKNWGEGWGFVPSDRALVFVDNHDNQRGHGAGGASILTFWDARLY
KMAVGFMLAHPYGFTRVMSSYRWPRQFQNGNDVNDWVGPPNNNGVIKE
VTINPDTTCGNDWVCEHRWRQIRNMVIFRNVVDGQPFTNWYDNGSNQV
AFGRGNRGFIVFNNDDWSFSLTLQTGLPAGTYCDVISGDKINGNCTGI
KIYVSDDGKAHFSISNSAEDPFIAIHAESKL SEQ ID NO: 37-heavy chain variable domain CDR2
of certain antibodies of the disclosure, in
accordance with CDRs as defined by Kabat
YISSGSSTIYYADSVKG SEQ ID NO: 38-light chain variable domain CDR1
of certain antibodies of the disclosure, in
accordance with CDRs as defined by Kabat
RASKSVSTSSYSYLA SEQ ID NO: 39-light chain variable domain CDR2
of certain antibodies of the disclosure, in
accordance with CDRs as defined by Kabat
YASYLQS SEQ ID NO: 40-amino acid sequence of a reference
humanized 3E10 light chain
DIVLTQSPASLAVSPGQRATITCRASKSVSTSSYSYMHWYQQKPGQPP
KLLIYYASYLESGVPARFSGSGSGTDFTLTINPVEANDTANYYCQHSR
EFPWTFGQGTKVEIK SEQ ID NO: 41-amino acid sequence of a reference
humanized 3E10 heavy chain
EVQLVESGGGLVQPGGSLRLSCSASGFTFSNYGMHWVRQAPGKGLEYV
SYISSGSSTIYYADTVKGRFTISRDNSKNTLYLQMSSLRAEDTAVYYC
VKRGLLLDYWGQGTLVTVSS SEQ ID NO: 42-Reference Humanized Fv3E10
DIVLTQSPASLAVSPGQRATITCRASKSVSTSSYSYMHWYQQKPGQPP

KLLIYYASYLESGVPARFSGSGSGTDFTLTINPVEANDTANYYCQHSR

EFPWTFGQGTKVEIKGGGGSGGGGSGGGGSEVQLVESGGGLVQPGGSL

RLSCSASGFTFSNYGMHWVRQAPGKGLEYVSYISSGSSTIYYADTVKG

RFTISRDNSKNTLYLQMSSLRAEDTAVYYCVKRGLLLDYWGQGTLVTV

SS

SEQ ID NO: 43--Heavy Chain + Alpha-Amylase
Fusion Protein Amino Acid Sequence (excluding
Linker Sequence)
EVQLQESGGGVVQPGGSLRLSCAASGFTFSNYGMHWIRQAPGKGLEWV

SYISSGSSTIYYADSVKGRFTISRDNSKNTLYLQMNSLRSEDTAVYYC

ARRGLLLDYWGQGTLVTVSSASTKGPSVFPLAPSSKSTSGGTAALGCL

VKDYFPEPVTVSWNSGALTSGVHTFPAVLQSSGLYSLSSVVTVPSSSL

GTQTYICNVNHKPSNTKVDKKVEPKSCDKTHTGGSGGGSGGGSGGQYS

PNTQQGRTSIVHLFEWRWVDIALECERYLAPKGFGGVQVSPPNENVAI

YNPFRPWWERYQPVSYKLCTRSGNEDEFRNMVTRCNNVGVRIYVDAVI

NHMCGNAVSAGTSSTCGSYFNPGSRDFPAVPYSGWDFNDGKCKTGSGD

IENYNDATQVRDCRLTGLLDLALEKDYVRSKIAEYMNHLIDIGVAGFR

LDASKHMWPGDIKAILDKLHNLNSNWFPAGSKPFIYQEVIDLGGEPIK

SSDYFGNGRVTEFKYGAKLGTVIRKWNGEKMSYLKNWGEGWGFVPSDR

ALVFVDNHDNQRGHGAGGASILTFWDARLYKMAVGFMLAHPYGFTRVM

SSYRWPRQFQNGNDVNDWVGPPNNNGVIKEVTINPDTTCGNDWVCEHR

WRQIRNMVIFRNVVDGQPFTNWYDNGSNQVAFGRGNRGFIVFNNDDWS

FSLTLQTGLPAGTYCDVISGDKINGNCTGIKIYVSDDGKAHFSISNSA

EDPFIAIHAESKL

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

I claim:

1. A chimeric polypeptide comprising: (i) an alpha-amylase polypeptide, and (ii) an internalizing moiety; wherein the alpha-amylase polypeptide comprises the amino acid sequence of SEQ ID NO: 1; and wherein the internalizing moiety is an antibody or antigen binding fragment, wherein the antibody or antigen binding fragment comprises a heavy chain variable domain and a light chain variable domain; wherein the heavy chain variable domain comprises the amino acid sequence of SEQ ID NO: 2; and wherein the light chain variable domain comprises the amino acid sequence of SEQ ID NO: 3.

2. A chimeric polypeptide comprising: (i) an alpha-amylase polypeptide, and (ii) an internalizing moiety; wherein the alpha-amylase polypeptide comprises the amino acid sequence of SEQ ID NO: 1, but wherein the alpha-amylase polypeptide does not comprise the full-length alpha-amylase polypeptide of SEQ ID NO: 36; and wherein the internalizing moiety is an antibody or antigen binding fragment, wherein the antibody or antigen binding fragment comprises a heavy chain comprising a heavy chain variable domain and a light chain comprising a light chain variable domain; wherein the heavy chain variable domain comprises the amino acid sequence of SEQ ID NO: 2; and wherein the light chain variable domain comprises the amino acid sequence of SEQ ID NO: 3.

3. The chimeric polypeptide of claim 1, wherein the alpha-amylase polypeptide consists of the amino acid sequence of SEQ ID NO: 1.

4. The chimeric polypeptide of claim 1, wherein the chimeric polypeptide is capable of hydrolyzing alpha-1,4-glucosidic bonds in a cell from a subject having Lafora Disease.

5. The chimeric polypeptide of claim 4, wherein the subject is a non-human animal.

6. The chimeric polypeptide of claim 4, wherein the subject is a human.

7. The chimeric polypeptide of claim 4, wherein the cell is selected from the group consisting of a muscle cell, a diaphragm muscle cell, a brain cell, and a neuron.

8. The chimeric polypeptide of claim 1, wherein the alpha-amylase polypeptide is chemically conjugated to the internalizing moiety.

9. The chimeric polypeptide of any one of claim 1, wherein the chimeric polypeptide comprises a fusion protein comprising the alpha-amylase polypeptide and the internalizing moiety.

10. The chimeric polypeptide of claim 9, wherein the chimeric polypeptide does not include a linker interconnecting the alpha-amylase polypeptide to the internalizing moiety.

11. The chimeric polypeptide of claim 9, wherein the fusion protein comprises a linker.

12. The chimeric polypeptide of, claim 1 wherein the internalizing moiety is conjugated or joined, directly or via a linker, to the N-terminal amino acid of the alpha-amylase polypeptide; or wherein the internalizing moiety is conjugated or joined, directly or via a linker, to the C-terminal amino acid of the alpha-amylase polypeptide; or wherein the internalizing moiety is conjugated or joined, directly or indirectly to an internal amino acid of the alpha-amylase polypeptide.

13. The chimeric polypeptide of claim 1, wherein the internalizing moiety comprises an antibody where the antibody comprises a heavy chain variable domain and a light chain variable domain; wherein the heavy chain variable domain comprises the amino acid sequence of SEQ ID NO: 2; and wherein the light chain variable domain comprises the amino acid sequence of SEQ ID NO: 3.

14. The chimeric polypeptide of claim 1, wherein the internalizing moiety comprises an antigen-binding fragment.

15. The chimeric polypeptide of claim 1, wherein the chimeric polypeptide comprises the amino acid sequence of SEQ ID NO: 7 or SEQ ID NO: 8.

16. The chimeric polypeptide of claim 1, wherein the chimeric polypeptide comprises the amino acid sequence of SEQ ID NOs: 7 and 8.

17. The chimeric polypeptide of claim 1, wherein the chimeric polypeptide comprises the amino acid sequence of SEQ ID NO: 9 or SEQ ID NO: 10.

18. The chimeric polypeptide of claim 1, wherein the chimeric polypeptide comprises the amino acid sequence of SEQ ID NOs: 9 and 10.

19. The chimeric polypeptide of claim 1, wherein the chimeric polypeptide comprises the amino acid sequence of SEQ ID NO: 43 or SEQ ID NO: 8.

20. The chimeric polypeptide of claim 1, wherein the chimeric polypeptide comprises the amino acid sequences of SEQ ID NOs: 8 and 43.

21. A nucleic acid construct, comprising a nucleotide sequence that encodes the chimeric polypeptide of claim 1 as a chimeric polypeptide comprising a fusion protein.

22. A method for treating a subject having Lafora disease, comprising administering to the subject a therapeutically effective amount of the chimeric polypeptide of claim 1.

* * * * *

SEQUENCE LISTING

```
<160> NUMBER OF SEQ ID NOS: 43

<210> SEQ ID NO 1
<211> LENGTH: 496
<212> TYPE: PRT
<213> ORGANISM: Artificial
<220> FEATURE:
<223> OTHER INFORMATION: Alpha Amylase Polypeptide Amino Acid Sequence

<400> SEQUENCE: 1
```

Gln Tyr Ser Pro Asn Thr Gln Gln Gly Arg Thr Ser Ile Val His Leu
1               5                   10                  15

Phe Glu Trp Arg Trp Val Asp Ile Ala Leu Glu Cys Glu Arg Tyr Leu
            20                  25                  30

Ala Pro Lys Gly Phe Gly Gly Val Gln Val Ser Pro Pro Asn Glu Asn
        35                  40                  45

Val Ala Ile Tyr Asn Pro Phe Arg Pro Trp Trp Glu Arg Tyr Gln Pro
    50                  55                  60

Val Ser Tyr Lys Leu Cys Thr Arg Ser Gly Asn Glu Asp Glu Phe Arg
65                  70                  75                  80

Asn Met Val Thr Arg Cys Asn Asn Val Gly Val Arg Ile Tyr Val Asp
                85                  90                  95

Ala Val Ile Asn His Met Cys Gly Asn Ala Val Ser Ala Gly Thr Ser
            100                 105                 110

Ser Thr Cys Gly Ser Tyr Phe Asn Pro Gly Ser Arg Asp Phe Pro Ala
        115                 120                 125

Val Pro Tyr Ser Gly Trp Asp Phe Asn Asp Gly Lys Cys Lys Thr Gly
    130                 135                 140

Ser Gly Asp Ile Glu Asn Tyr Asn Asp Ala Thr Gln Val Arg Asp Cys
145                 150                 155                 160

Arg Leu Thr Gly Leu Leu Asp Leu Ala Leu Glu Lys Asp Tyr Val Arg

```
                165                 170                 175
Ser Lys Ile Ala Glu Tyr Met Asn His Leu Ile Asp Ile Gly Val Ala
            180                 185                 190

Gly Phe Arg Leu Asp Ala Ser Lys His Met Trp Pro Gly Asp Ile Lys
        195                 200                 205

Ala Ile Leu Asp Lys Leu His Asn Leu Asn Ser Asn Trp Phe Pro Ala
    210                 215                 220

Gly Ser Lys Pro Phe Ile Tyr Gln Glu Val Ile Asp Leu Gly Gly Glu
225                 230                 235                 240

Pro Ile Lys Ser Ser Asp Tyr Phe Gly Asn Gly Arg Val Thr Glu Phe
                245                 250                 255

Lys Tyr Gly Ala Lys Leu Gly Thr Val Ile Arg Lys Trp Asn Gly Glu
            260                 265                 270

Lys Met Ser Tyr Leu Lys Asn Trp Gly Glu Gly Trp Gly Phe Val Pro
        275                 280                 285

Ser Asp Arg Ala Leu Val Phe Val Asp Asn His Asp Asn Gln Arg Gly
    290                 295                 300

His Gly Ala Gly Gly Ala Ser Ile Leu Thr Phe Trp Asp Ala Arg Leu
305                 310                 315                 320

Tyr Lys Met Ala Val Gly Phe Met Leu Ala His Pro Tyr Gly Phe Thr
                325                 330                 335

Arg Val Met Ser Ser Tyr Arg Trp Pro Arg Gln Phe Gln Asn Gly Asn
            340                 345                 350

Asp Val Asn Asp Trp Val Gly Pro Pro Asn Asn Asn Gly Val Ile Lys
        355                 360                 365

Glu Val Thr Ile Asn Pro Asp Thr Thr Cys Gly Asn Asp Trp Val Cys
    370                 375                 380

Glu His Arg Trp Arg Gln Ile Arg Asn Met Val Ile Phe Arg Asn Val
385                 390                 395                 400

Val Asp Gly Gln Pro Phe Thr Asn Trp Tyr Asp Asn Gly Ser Asn Gln
                405                 410                 415

Val Ala Phe Gly Arg Gly Asn Arg Gly Phe Ile Val Phe Asn Asn Asp
            420                 425                 430

Asp Trp Ser Phe Ser Leu Thr Leu Gln Thr Gly Leu Pro Ala Gly Thr
        435                 440                 445

Tyr Cys Asp Val Ile Ser Gly Asp Lys Ile Asn Gly Asn Cys Thr Gly
    450                 455                 460

Ile Lys Ile Tyr Val Ser Asp Asp Gly Lys Ala His Phe Ser Ile Ser
465                 470                 475                 480

Asn Ser Ala Glu Asp Pro Phe Ile Ala Ile His Ala Glu Ser Lys Leu
                485                 490                 495

<210> SEQ ID NO 2
<211> LENGTH: 116
<212> TYPE: PRT
<213> ORGANISM: Artificial
<220> FEATURE:
<223> OTHER INFORMATION: Humanized Variable Heavy Chain Amino Acid
      Sequence

<400> SEQUENCE: 2

Glu Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met His Trp Ile Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ser Glu Asp Thr Ala Val Tyr Tyr Cys
                 85                  90                  95

Ala Arg Arg Gly Leu Leu Leu Asp Tyr Trp Gly Gln Gly Thr Leu Val
            100                 105                 110

Thr Val Ser Ser
        115

<210> SEQ ID NO 3
<211> LENGTH: 111
<212> TYPE: PRT
<213> ORGANISM: Artificial
<220> FEATURE:
<223> OTHER INFORMATION: Humanized Variable Light Chain Amino Acid
      Sequence (VL2)

<400> SEQUENCE: 3

Asp Ile Gln Met Thr Gln Ser Pro Ser Ser Leu Ser Ala Ser Val Gly
 1               5                  10                  15

Asp Arg Val Thr Ile Ser Cys Arg Ala Ser Lys Ser Val Ser Thr Ser
             20                  25                  30

Ser Tyr Ser Tyr Met His Trp Tyr Gln Gln Lys Pro Glu Lys Ala Pro
         35                  40                  45

Lys Leu Leu Ile Lys Tyr Ala Ser Tyr Leu Gln Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Val Ala Thr Tyr Tyr Cys Gln His Ser Arg
                 85                  90                  95

Glu Phe Pro Trp Thr Phe Gly Ala Gly Thr Lys Leu Glu Leu Lys
            100                 105                 110

<210> SEQ ID NO 4
<211> LENGTH: 19
<212> TYPE: PRT
<213> ORGANISM: Artificial
<220> FEATURE:
<223> OTHER INFORMATION: Heavy Chain Leader Amino Acid Sequence

<400> SEQUENCE: 4

Met Glu Phe Gly Leu Ser Trp Leu Phe Leu Val Ala Ile Leu Lys Gly
 1               5                  10                  15

Val Gln Cys

<210> SEQ ID NO 5
<211> LENGTH: 22
<212> TYPE: PRT
<213> ORGANISM: Artificial
<220> FEATURE:
<223> OTHER INFORMATION: Light Chain Leader Amino Acid Sequence

<400> SEQUENCE: 5

Met Asp Met Arg Val Pro Ala Gln Leu Leu Gly Leu Leu Leu Leu Trp
 1               5                  10                  15

Leu Arg Gly Ala Arg Cys
```

<210> SEQ ID NO 6
<211> LENGTH: 13
<212> TYPE: PRT
<213> ORGANISM: Artificial
<220> FEATURE:
<223> OTHER INFORMATION: Glycine-Serine Linker Amino Acid Sequence

<400> SEQUENCE: 6

```
Gly Gly Ser Gly Gly Gly Ser Gly Gly Gly Ser Gly Gly
1               5                   10
```

<210> SEQ ID NO 7
<211> LENGTH: 224
<212> TYPE: PRT
<213> ORGANISM: Artificial
<220> FEATURE:
<223> OTHER INFORMATION: Humanized Heavy Chain Amino Acid Sequence
      (including human IgG1 CH1 and truncated hinge constant regions)

<400> SEQUENCE: 7

```
Glu Val Gln Leu Gln Glu Ser Gly Gly Val Val Gln Pro Gly Gly
1               5                   10                  15

Ser Leu Arg Leu Ser Cys Ala Ala Ser Gly Phe Thr Phe Ser Asn Tyr
            20                  25                  30

Gly Met His Trp Ile Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Arg Arg Gly Leu Leu Leu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

<210> SEQ ID NO 8
<211> LENGTH: 218
<212> TYPE: PRT
<213> ORGANISM: Artificial
<220> FEATURE:
<223> OTHER INFORMATION: Humanized Light Chain Amino Acid Sequence
      (including human kappa light chain region)

<400> SEQUENCE: 8

-continued

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Lys Ser Val Ser Thr Ser
            20                  25                  30

Ser Tyr Ser Tyr Met His Trp Tyr Gln Gln Lys Pro Glu Lys Ala Pro
        35                  40                  45

Lys Leu Leu Ile Lys Tyr Ala Ser Tyr Leu Gln Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln His Ser Arg
                85                  90                  95

Glu Phe Pro Trp Thr Phe Gly Ala Gly Thr Lys Leu Glu Leu Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 9
<211> LENGTH: 752
<212> TYPE: PRT
<213> ORGANISM: Artificial
<220> FEATURE:
<223> OTHER INFORMATION: Heavy Chain + Alpha-Amylase Fusion Protein
      Amino Acid Sequence (Including Leader and Linker Sequences)

<400> SEQUENCE: 9

Met Glu Phe Gly Leu Ser Trp Leu Phe Leu Val Ala Ile Leu Lys Gly
1               5                   10                  15

Val Gln Cys Glu Val Gln Leu Gln Glu Ser Gly Gly Gly Val Val Gln
            20                  25                  30

Pro Gly Gly Ser Leu Arg Leu Ser Cys Ala Ala Ser Gly Phe Thr Phe
        35                  40                  45

Ser Asn Tyr Gly Met His Trp Ile Arg Gln Ala Pro Gly Lys Gly Leu
    50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ser Glu Asp Thr Ala Val
            100                 105                 110

Tyr Tyr Cys Ala Arg Arg Gly Leu Leu Leu Asp Tyr Trp Gly Gln Gly
        115                 120                 125

Thr Leu Val Thr Val Ser Ser Ala Ser Thr Lys Gly Pro Ser Val Phe
    130                 135                 140
```

```
Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
210                 215                 220

Ser Asn Thr Lys Val Asp Lys Lys Val Glu Pro Lys Ser Cys Asp Lys
225                 230                 235                 240

Thr His Thr Gly Gly Ser Gly Gly Gly Ser Gly Gly Gly Ser Gly Gly
                245                 250                 255

Gln Tyr Ser Pro Asn Thr Gln Gln Gly Arg Thr Ser Ile Val His Leu
            260                 265                 270

Phe Glu Trp Arg Trp Val Asp Ile Ala Leu Glu Cys Glu Arg Tyr Leu
        275                 280                 285

Ala Pro Lys Gly Phe Gly Gly Val Gln Val Ser Pro Pro Asn Glu Asn
290                 295                 300

Val Ala Ile Tyr Asn Pro Phe Arg Pro Trp Trp Glu Arg Tyr Gln Pro
305                 310                 315                 320

Val Ser Tyr Lys Leu Cys Thr Arg Ser Gly Asn Glu Asp Glu Phe Arg
                325                 330                 335

Asn Met Val Thr Arg Cys Asn Asn Val Gly Val Arg Ile Tyr Val Asp
            340                 345                 350

Ala Val Ile Asn His Met Cys Gly Asn Ala Val Ser Ala Gly Thr Ser
        355                 360                 365

Ser Thr Cys Gly Ser Tyr Phe Asn Pro Gly Ser Arg Asp Phe Pro Ala
370                 375                 380

Val Pro Tyr Ser Gly Trp Asp Phe Asn Asp Gly Lys Cys Lys Thr Gly
385                 390                 395                 400

Ser Gly Asp Ile Glu Asn Tyr Asn Asp Ala Thr Gln Val Arg Asp Cys
                405                 410                 415

Arg Leu Thr Gly Leu Leu Asp Leu Ala Leu Glu Lys Asp Tyr Val Arg
            420                 425                 430

Ser Lys Ile Ala Glu Tyr Met Asn His Leu Ile Asp Ile Gly Val Ala
        435                 440                 445

Gly Phe Arg Leu Asp Ala Ser Lys His Met Trp Pro Gly Asp Ile Lys
450                 455                 460

Ala Ile Leu Asp Lys Leu His Asn Leu Asn Ser Asn Trp Phe Pro Ala
465                 470                 475                 480

Gly Ser Lys Pro Phe Ile Tyr Gln Glu Val Ile Asp Leu Gly Gly Glu
                485                 490                 495

Pro Ile Lys Ser Ser Asp Tyr Phe Gly Asn Gly Arg Val Thr Glu Phe
            500                 505                 510

Lys Tyr Gly Ala Lys Leu Gly Thr Val Ile Arg Lys Trp Asn Gly Glu
        515                 520                 525

Lys Met Ser Tyr Leu Lys Asn Trp Gly Glu Gly Trp Gly Phe Val Pro
530                 535                 540

Ser Asp Arg Ala Leu Val Phe Val Asp Asn His Asp Asn Gln Arg Gly
545                 550                 555                 560
```

His Gly Ala Gly Gly Ala Ser Ile Leu Thr Phe Trp Asp Ala Arg Leu
            565                 570                 575

Tyr Lys Met Ala Val Gly Phe Met Leu Ala His Pro Tyr Gly Phe Thr
        580                 585                 590

Arg Val Met Ser Ser Tyr Arg Trp Pro Arg Gln Phe Gln Asn Gly Asn
    595                 600                 605

Asp Val Asn Asp Trp Val Gly Pro Asn Asn Asn Gly Val Ile Lys
610                 615                 620

Glu Val Thr Ile Asn Pro Asp Thr Thr Cys Gly Asn Asp Trp Val Cys
625                 630                 635                 640

Glu His Arg Trp Arg Gln Ile Arg Asn Met Val Ile Phe Arg Asn Val
                645                 650                 655

Val Asp Gly Gln Pro Phe Thr Asn Trp Tyr Asp Asn Gly Ser Asn Gln
            660                 665                 670

Val Ala Phe Gly Arg Gly Asn Arg Gly Phe Ile Val Phe Asn Asn Asp
        675                 680                 685

Asp Trp Ser Phe Ser Leu Thr Leu Gln Thr Gly Leu Pro Ala Gly Thr
    690                 695                 700

Tyr Cys Asp Val Ile Ser Gly Asp Lys Ile Asn Gly Asn Cys Thr Gly
705                 710                 715                 720

Ile Lys Ile Tyr Val Ser Asp Asp Gly Lys Ala His Phe Ser Ile Ser
                725                 730                 735

Asn Ser Ala Glu Asp Pro Phe Ile Ala Ile His Ala Glu Ser Lys Leu
            740                 745                 750

<210> SEQ ID NO 10
<211> LENGTH: 240
<212> TYPE: PRT
<213> ORGANISM: Artificial
<220> FEATURE:
<223> OTHER INFORMATION: Light Chain + Leader Amino Acid Sequence

<400> SEQUENCE: 10

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Ser Cys Arg Ala Ser
        35                  40                  45

Lys Ser Val Ser Thr Ser Ser Tyr Ser Tyr Met His Trp Tyr Gln Gln
    50                  55                  60

Lys Pro Glu Lys Ala Pro Lys Leu Leu Ile Lys Tyr Ala Ser Tyr Leu
65                  70                  75                  80

Gln Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Val Ala Thr Tyr
            100                 105                 110

Tyr Cys Gln His Ser Arg Glu Phe Pro Trp Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

```
Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
            210                 215                 220

Gln Gly Leu Ser Ser Pro Val Thr Lys Ser Phe Asn Arg Gly Glu Cys
225                 230                 235                 240

<210> SEQ ID NO 11
<211> LENGTH: 108
<212> TYPE: PRT
<213> ORGANISM: Artificial
<220> FEATURE:
<223> OTHER INFORMATION: Heavy Chain IgG1 CH1 and Truncated Hinge
      Constant Domain

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 12
<211> LENGTH: 107
<212> TYPE: PRT
<213> ORGANISM: Artificial
<220> FEATURE:
<223> OTHER INFORMATION: Human Kappa Constant Domain of Km3 Allotype

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 13
<211> LENGTH: 15
<212> TYPE: PRT
```

```
<213> ORGANISM: Artificial
<220> FEATURE:
<223> OTHER INFORMATION: GS3 linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 14
<212> TYPE: PRT
<213> ORGANISM: Artificial
<220> FEATURE:
<223> OTHER INFORMATION: Linker

<400> SEQUENCE: 14

Gly Ser Thr Ser Gly Ser Gly Lys Ser Ser Glu Gly Lys Gly
1               5                   10

<210> SEQ ID NO 15
<211> LENGTH: 7
<212> TYPE: PRT
<213> ORGANISM: Artificial
<220> FEATURE:
<223> OTHER INFORMATION: His tag

<400> SEQUENCE: 15

His His His His His His His
1               5

<210> SEQ ID NO 16
<211> LENGTH: 10
<212> TYPE: PRT
<213> ORGANISM: Artificial
<220> FEATURE:
<223> OTHER INFORMATION: c-Myc tag

<400> SEQUENCE: 16

Glu Gln Lys Leu Ile Ser Glu Glu Asp Leu
1               5                   10

<210> SEQ ID NO 17
<211> LENGTH: 116
<212> TYPE: PRT
<213> ORGANISM: Artificial
<220> FEATURE:
<223> OTHER INFORMATION: exemplary 3E10 Variable Heavy Chain (VH having
      D31N substitution; see examples)

<400> SEQUENCE: 17

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110
```

Thr Val Ser Ser
          115

<210> SEQ ID NO 18
<211> LENGTH: 111
<212> TYPE: PRT
<213> ORGANISM: Artificial
<220> FEATURE:
<223> OTHER INFORMATION: 3E10 Variable Light Chain (VL)

<400> SEQUENCE: 18

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110

<210> SEQ ID NO 19
<211> LENGTH: 5
<212> TYPE: PRT
<213> ORGANISM: Artificial
<220> FEATURE:
<223> OTHER INFORMATION: heavy chain variable domain CDR1 of 3E10 VH

<400> SEQUENCE: 19

Asn Tyr Gly Met His
1               5

<210> SEQ ID NO 20
<211> LENGTH: 17
<212> TYPE: PRT
<213> ORGANISM: Artificial
<220> FEATURE:
<223> OTHER INFORMATION: heavy chain variable domain CDR2 of 3E10 VH

<400> SEQUENCE: 20

Tyr Ile Ser Ser Gly Ser Ser Thr Ile Tyr Tyr Ala Asp Thr Val Lys
1               5                   10                  15

Gly

<210> SEQ ID NO 21
<211> LENGTH: 7
<212> TYPE: PRT
<213> ORGANISM: Artificial
<220> FEATURE:
<223> OTHER INFORMATION: heavy chain variable domain CDR3 of 3E10 VH

<400> SEQUENCE: 21

Arg Gly Leu Leu Leu Asp Tyr
1               5

<210> SEQ ID NO 22
<211> LENGTH: 15

```
<212> TYPE: PRT
<213> ORGANISM: Artificial
<220> FEATURE:
<223> OTHER INFORMATION: light chain variable domain CDR1 of 3E10 VL

<400> SEQUENCE: 22

Arg Ala Ser Lys Ser Val Ser Thr Ser Ser Tyr Ser Tyr Met His
1               5                   10                  15

<210> SEQ ID NO 23
<211> LENGTH: 7
<212> TYPE: PRT
<213> ORGANISM: Artificial
<220> FEATURE:
<223> OTHER INFORMATION: light chain variable domain CDR2 of 3E10 VL

<400> SEQUENCE: 23

Tyr Ala Ser Tyr Leu Glu Ser
1               5

<210> SEQ ID NO 24
<211> LENGTH: 9
<212> TYPE: PRT
<213> ORGANISM: Artificial
<220> FEATURE:
<223> OTHER INFORMATION: light chain variable domain CDR3 of 3E10 VL

<400> SEQUENCE: 24

Gln His Ser Arg Glu Phe Pro Trp Thr
1               5

<210> SEQ ID NO 25
<211> LENGTH: 4
<212> TYPE: PRT
<213> ORGANISM: Artificial
<220> FEATURE:
<223> OTHER INFORMATION: chimeric polypeptide

<400> SEQUENCE: 25

Ala Gly Ile His
1

<210> SEQ ID NO 26
<211> LENGTH: 5
<212> TYPE: PRT
<213> ORGANISM: Artificial
<220> FEATURE:
<223> OTHER INFORMATION: chimeric polypeptide

<400> SEQUENCE: 26

Ser Ala Gly Ile His
1               5

<210> SEQ ID NO 27
<211> LENGTH: 8
<212> TYPE: PRT
<213> ORGANISM: Artificial
<220> FEATURE:
<223> OTHER INFORMATION: heavy chain variable (VH) domain CDR1 of
      exemplary 3E10 molecule

<400> SEQUENCE: 27

Gly Phe Thr Phe Ser Asn Tyr Gly
1               5

<210> SEQ ID NO 28
<211> LENGTH: 8
```

```
<212> TYPE: PRT
<213> ORGANISM: Artificial
<220> FEATURE:
<223> OTHER INFORMATION: heavy chain variable (VH) domain CDR2 of
      exemplary 3E10 molecule

<400> SEQUENCE: 28

Ile Ser Ser Gly Ser Ser Thr Ile
1               5

<210> SEQ ID NO 29
<211> LENGTH: 9
<212> TYPE: PRT
<213> ORGANISM: Artificial
<220> FEATURE:
<223> OTHER INFORMATION: heavy chain variable (VH) domain CDR3 of
      exemplary 3E10 molecule

<400> SEQUENCE: 29

Ala Arg Arg Gly Leu Leu Leu Asp Tyr
1               5

<210> SEQ ID NO 30
<211> LENGTH: 10
<212> TYPE: PRT
<213> ORGANISM: Artificial
<220> FEATURE:
<223> OTHER INFORMATION: light chain variable (VL) domain CDR1 of
      exemplary 3E10 molecule

<400> SEQUENCE: 30

Lys Ser Val Ser Thr Ser Ser Tyr Ser Tyr
1               5                   10

<210> SEQ ID NO 31
<211> LENGTH: 3
<212> TYPE: PRT
<213> ORGANISM: Artificial
<220> FEATURE:
<223> OTHER INFORMATION: light chain variable (VL) domain CDR2 of
      exemplary 3E10 molecule

<400> SEQUENCE: 31

Tyr Ala Ser
1

<210> SEQ ID NO 32
<211> LENGTH: 9
<212> TYPE: PRT
<213> ORGANISM: Artificial
<220> FEATURE:
<223> OTHER INFORMATION: light chain variable (VL) domain CDR3 of
      exemplary 3E10 molecule

<400> SEQUENCE: 32

Gln His Ser Arg Glu Phe Pro Trp Thr
1               5

<210> SEQ ID NO 33
<211> LENGTH: 116
<212> TYPE: PRT
<213> ORGANISM: Artificial
<220> FEATURE:
<223> OTHER INFORMATION: amino acid sequence of humanized 3E10 heavy
      chain (hVH1)

<400> SEQUENCE: 33

Glu Val Gln Leu Val Gln Ser Gly Gly Gly Leu Ile Gln Pro Gly Gly
```

```
1               5                   10                  15
Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ser Tyr Ile Ser Ser Gly Ser Ser Thr Ile Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Val
            100                 105                 110

Thr Val Ser Ser
            115

<210> SEQ ID NO 34
<211> LENGTH: 116
<212> TYPE: PRT
<213> ORGANISM: Artificial
<220> FEATURE:
<223> OTHER INFORMATION: amino acid sequence of humanized 3E10 heavy
      chain (hVH2)

<400> SEQUENCE: 34

Glu Val Gln Leu Val Glu Ser Gly Gly Gly Leu Ile Gln Pro Gly Gly
 1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
            35                  40                  45

Ser Tyr Ile Ser Ser Gly Ser Ser Thr Ile Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Thr Ser Leu Arg Ala Glu Asp Thr Ala Val Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
            115

<210> SEQ ID NO 35
<211> LENGTH: 111
<212> TYPE: PRT
<213> ORGANISM: Artificial
<220> FEATURE:
<223> OTHER INFORMATION: amino acid sequence of humanized 3E10 light
      chain (hVL1)

<400> SEQUENCE: 35

Asp Ile Gln Met Thr Gln Ser Pro Ser Ser Leu Ser Ala Ser Val Gly
 1               5                   10                  15

Asp Arg Val Thr Ile Thr Cys Arg Ala Ser Lys Ser Val Ser Thr Ser
            20                  25                  30

Ser Tyr Ser Tyr Leu Ala Trp Tyr Gln Gln Lys Pro Glu Lys Ala Pro
            35                  40                  45

Lys Leu Leu Ile Lys Tyr Ala Ser Tyr Leu Gln Ser Gly Val Pro Ser
```

```
                50              55              60
Arg Phe Ser Gly Ser Gly Ser Gly Thr Asp Phe Thr Leu Thr Ile Ser
 65              70              75              80

Ser Leu Gln Pro Glu Asp Phe Ala Thr Tyr Tyr Cys Gln His Ser Arg
                85              90              95

Glu Phe Pro Trp Thr Phe Gly Ala Gly Thr Lys Leu Glu Leu Lys
            100             105             110

<210> SEQ ID NO 36
<211> LENGTH: 511
<212> TYPE: PRT
<213> ORGANISM: Artificial
<220> FEATURE:
<223> OTHER INFORMATION: Human Pancreatic Alpha Amylase Amino Acid
      Sequence

<400> SEQUENCE: 36

Met Lys Phe Phe Leu Leu Phe Thr Ile Gly Phe Cys Trp Ala Gln
 1               5              10              15

Tyr Ser Pro Asn Thr Gln Gln Gly Arg Thr Ser Ile Val His Leu Phe
                20              25              30

Glu Trp Arg Trp Val Asp Ile Ala Leu Glu Cys Glu Arg Tyr Leu Ala
            35              40              45

Pro Lys Gly Phe Gly Gly Val Gln Val Ser Pro Pro Asn Glu Asn Val
 50              55              60

Ala Ile Tyr Asn Pro Phe Arg Pro Trp Trp Glu Arg Tyr Gln Pro Val
 65              70              75              80

Ser Tyr Lys Leu Cys Thr Arg Ser Gly Asn Glu Asp Glu Phe Arg Asn
                85              90              95

Met Val Thr Arg Cys Asn Asn Val Gly Val Arg Ile Tyr Val Asp Ala
            100             105             110

Val Ile Asn His Met Cys Gly Asn Ala Val Ser Ala Gly Thr Ser Ser
            115             120             125

Thr Cys Gly Ser Tyr Phe Asn Pro Gly Ser Arg Asp Phe Pro Ala Val
            130             135             140

Pro Tyr Ser Gly Trp Asp Phe Asn Asp Gly Lys Cys Lys Thr Gly Ser
145             150             155             160

Gly Asp Ile Glu Asn Tyr Asn Asp Ala Thr Gln Val Arg Asp Cys Arg
                165             170             175

Leu Thr Gly Leu Leu Asp Leu Ala Leu Glu Lys Asp Tyr Val Arg Ser
            180             185             190

Lys Ile Ala Glu Tyr Met Asn His Leu Ile Asp Ile Gly Val Ala Gly
            195             200             205

Phe Arg Leu Asp Ala Ser Lys His Met Trp Pro Gly Asp Ile Lys Ala
 210             215             220

Ile Leu Asp Lys Leu His Asn Leu Asn Ser Asn Trp Phe Pro Ala Gly
225             230             235             240

Ser Lys Pro Phe Ile Tyr Gln Glu Val Ile Asp Leu Gly Gly Glu Pro
                245             250             255

Ile Lys Ser Ser Asp Tyr Phe Gly Asn Gly Arg Val Thr Glu Phe Lys
            260             265             270

Tyr Gly Ala Lys Leu Gly Thr Val Ile Arg Lys Trp Asn Gly Glu Lys
            275             280             285

Met Ser Tyr Leu Lys Asn Trp Gly Glu Gly Trp Gly Phe Val Pro Ser
 290             295             300
```

```
Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
            340                 345                 350

Val Met Ser Ser Tyr Arg Trp Pro Arg Gln Phe Gln Asn Gly Asn Asp
        355                 360                 365

Val Asn Asp Trp Val Gly Pro Asn Asn Gly Val Ile Lys Glu
    370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Ile Phe Arg Asn Val Val
                405                 410                 415

Asp Gly Gln Pro Phe Thr Asn Trp Tyr Asp Asn Gly Ser Asn Gln Val
                420                 425                 430

Ala Phe Gly Arg Gly Asn Arg Gly Phe Ile Val Phe Asn Asn Asp Asp
            435                 440                 445

Trp Ser Phe Ser Leu Thr Leu Gln Thr Gly Leu Pro Ala Gly Thr Tyr
450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ile His Ala Glu Ser Lys Leu
                500                 505                 510

<210> SEQ ID NO 37
<211> LENGTH: 17
<212> TYPE: PRT
<213> ORGANISM: Artificial
<220> FEATURE:
<223> OTHER INFORMATION: heavy chain variable domain CDR2

<400> SEQUENCE: 37

Tyr Ile Ser Ser Gly Ser Ser Thr Ile Tyr Tyr Ala Asp Ser Val Lys
1               5                   10                  15

Gly

<210> SEQ ID NO 38
<211> LENGTH: 15
<212> TYPE: PRT
<213> ORGANISM: Artificial
<220> FEATURE:
<223> OTHER INFORMATION: light chain variable domain CDR1

<400> SEQUENCE: 38

Arg Ala Ser Lys Ser Val Ser Thr Ser Ser Tyr Ser Tyr Leu Ala
1               5                   10                  15

<210> SEQ ID NO 39
<211> LENGTH: 7
<212> TYPE: PRT
<213> ORGANISM: Artificial
<220> FEATURE:
<223> OTHER INFORMATION: light chain variable domain CDR2

<400> SEQUENCE: 39

Tyr Ala Ser Tyr Leu Gln Ser
1               5
```

```
<210> SEQ ID NO 40
<211> LENGTH: 111
<212> TYPE: PRT
<213> ORGANISM: Artificial
<220> FEATURE:
<223> OTHER INFORMATION: amino acid sequence of a reference humanized
      3E10 light chain

<400> SEQUENCE: 40

Asp Ile Val Leu Thr Gln Ser Pro Ala Ser Leu Ala Val Ser Pro Gly
1               5                   10                  15

Gln Arg Ala Thr Ile Thr Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Tyr Tyr Ala Ser Tyr Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Arg
                85                  90                  95

Glu Phe Pro Trp Thr Phe Gly Gln Gly Thr Lys Val Glu Ile Lys
            100                 105                 110

<210> SEQ ID NO 41
<211> LENGTH: 116
<212> TYPE: PRT
<213> ORGANISM: Artificial
<220> FEATURE:
<223> OTHER INFORMATION: amino acid sequence of a reference humanized
      3E10 heavy chain

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Gly Met His Trp Val Arg Gln Ala Pro Gly Lys Gly Leu Glu Tyr Val
        35                  40                  45

Ser Tyr Ile Ser Ser Gly Ser Ser Thr Ile Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Arg Gly Leu Leu Leu Asp Tyr Trp Gly Gln Gly Thr Leu Val
            100                 105                 110

Thr Val Ser Ser
        115

<210> SEQ ID NO 42
<211> LENGTH: 242
<212> TYPE: PRT
<213> ORGANISM: Artificial
<220> FEATURE:
<223> OTHER INFORMATION: Reference Humanized Fv3E10

<400> SEQUENCE: 42

Asp Ile Val Leu Thr Gln Ser Pro Ala Ser Leu Ala Val Ser Pro Gly
```

```
              1               5                  10                 15
           Gln Arg Ala Thr Ile Thr Cys Arg Ala Ser Lys Ser Val Ser Thr Ser
                            20                 25                 30
           Ser Tyr Ser Tyr Met His Trp Tyr Gln Gln Lys Pro Gly Gln Pro Pro
                        35                 40                 45
           Lys Leu Leu Ile Tyr Tyr Ala Ser Tyr Leu Glu Ser Gly Val Pro Ala
                    50                 55                 60
           Arg Phe Ser Gly Ser Gly Ser Gly Thr Asp Phe Thr Leu Thr Ile Asn
           65                 70                 75                 80
           Pro Val Glu Ala Asn Asp Thr Ala Asn Tyr Tyr Cys Gln His Ser Arg
                            85                 90                 95
           Glu Phe Pro Trp Thr Phe Gly Gln Gly Thr Lys Val Glu Ile Lys Gly
                       100                105                110
           Gly Gly Gly Ser Gly Gly Gly Gly Ser Gly Gly Gly Gly Ser Glu Val
                       115                120                125
           Gln Leu Val Glu Ser Gly Gly Gly Leu Val Gln Pro Gly Gly Ser Leu
                       130                135                140
           Arg Leu Ser Cys Ser Ala Ser Gly Phe Thr Phe Ser Asn Tyr Gly Met
           145                150                155                160
           His Trp Val Arg Gln Ala Pro Gly Lys Gly Leu Glu Tyr Val Ser Tyr
                           165                170                175
           Ile Ser Ser Gly Ser Ser Thr Ile Tyr Tyr Ala Asp Thr Val Lys Gly
                       180                185                190
           Arg Phe Thr Ile Ser Arg Asp Asn Ser Lys Asn Thr Leu Tyr Leu Gln
                       195                200                205
           Met Ser Ser Leu Arg Ala Glu Asp Thr Ala Val Tyr Tyr Cys Val Lys
                       210                215                220
           Arg Gly Leu Leu Leu Asp Tyr Trp Gly Gln Gly Thr Leu Val Thr Val
           225                230                235                240
           Ser Ser

<210> SEQ ID NO 43
<211> LENGTH: 733
<212> TYPE: PRT
<213> ORGANISM: Artificial
<220> FEATURE:
<223> OTHER INFORMATION: Heavy Chain + Alpha-Amylase Fusion Protein
      Amino Acid Sequence

<400> SEQUENCE: 43

Glu Val Gln Leu Gln Glu Ser Gly Gly Val Val Gln Pro Gly Gly
           1               5                  10                 15
           Ser Leu Arg Leu Ser Cys Ala Ala Ser Gly Phe Thr Phe Ser Asn Tyr
                            20                 25                 30
           Gly Met His Trp Ile Arg Gln Ala Pro Gly Lys Gly Leu Glu Trp Val
                        35                 40                 45
           Ser Tyr Ile Ser Ser Gly Ser Ser Thr Ile Tyr Tyr Ala Asp Ser Val
                    50                 55                 60
           Lys Gly Arg Phe Thr Ile Ser Arg Asp Asn Ser Lys Asn Thr Leu Tyr
           65                 70                 75                 80
           Leu Gln Met Asn Ser Leu Arg Ser Glu Asp Thr Ala Val Tyr Tyr Cys
                            85                 90                 95
           Ala Arg Arg Gly Leu Leu Leu Asp Tyr Trp Gly Gln Gly Thr Leu Val
                       100                105                110
           Thr Val Ser Ser Ala Ser Thr Lys Gly Pro Ser Val Phe Pro Leu Ala
```

```
            115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
210                 215                 220

Gly Gly Ser Gly Gly Ser Gly Gly Ser Gly Gly Gln Tyr Ser
225                 230                 235                 240

Pro Asn Thr Gln Gln Gly Arg Thr Ser Ile Val His Leu Phe Glu Trp
                245                 250                 255

Arg Trp Val Asp Ile Ala Leu Glu Cys Glu Arg Tyr Leu Ala Pro Lys
                260                 265                 270

Gly Phe Gly Gly Val Gln Val Ser Pro Pro Asn Glu Asn Val Ala Ile
                275                 280                 285

Tyr Asn Pro Phe Arg Pro Trp Trp Glu Arg Tyr Gln Pro Val Ser Tyr
290                 295                 300

Lys Leu Cys Thr Arg Ser Gly Asn Glu Asp Glu Phe Arg Asn Met Val
305                 310                 315                 320

Thr Arg Cys Asn Asn Val Gly Val Arg Ile Tyr Val Asp Ala Val Ile
                325                 330                 335

Asn His Met Cys Gly Asn Ala Val Ser Ala Gly Thr Ser Thr Cys
                340                 345                 350

Gly Ser Tyr Phe Asn Pro Gly Ser Arg Asp Phe Pro Ala Val Pro Tyr
                355                 360                 365

Ser Gly Trp Asp Phe Asn Asp Gly Lys Cys Lys Thr Gly Ser Gly Asp
                370                 375                 380

Ile Glu Asn Tyr Asn Asp Ala Thr Gln Val Arg Asp Cys Arg Leu Thr
385                 390                 395                 400

Gly Leu Leu Asp Leu Ala Leu Glu Lys Asp Tyr Val Arg Ser Lys Ile
                405                 410                 415

Ala Glu Tyr Met Asn His Leu Ile Asp Ile Gly Val Ala Gly Phe Arg
                420                 425                 430

Leu Asp Ala Ser Lys His Met Trp Pro Gly Asp Ile Lys Ala Ile Leu
                435                 440                 445

Asp Lys Leu His Asn Leu Asn Ser Asn Trp Phe Pro Ala Gly Ser Lys
                450                 455                 460

Pro Phe Ile Tyr Gln Glu Val Ile Asp Leu Gly Gly Glu Pro Ile Lys
465                 470                 475                 480

Ser Ser Asp Tyr Phe Gly Asn Gly Arg Val Thr Glu Phe Lys Tyr Gly
                485                 490                 495

Ala Lys Leu Gly Thr Val Ile Arg Lys Trp Asn Gly Glu Lys Met Ser
                500                 505                 510

Tyr Leu Lys Asn Trp Gly Glu Gly Trp Gly Phe Val Pro Ser Asp Arg
                515                 520                 525

Ala Leu Val Phe Val Asp Asn His Asp Asn Gln Arg Gly His Gly Ala
                530                 535                 540
```

```
Gly Gly Ala Ser Ile Leu Thr Phe Trp Asp Ala Arg Leu Tyr Lys Met
545                 550                 555                 560

Ala Val Gly Phe Met Leu Ala His Pro Tyr Gly Phe Thr Arg Val Met
                565                 570                 575

Ser Ser Tyr Arg Trp Pro Arg Gln Phe Gln Asn Gly Asn Asp Val Asn
            580                 585                 590

Asp Trp Val Gly Pro Pro Asn Asn Asn Gly Val Ile Lys Glu Val Thr
        595                 600                 605

Ile Asn Pro Asp Thr Thr Cys Gly Asn Asp Trp Val Cys Glu His Arg
    610                 615                 620

Trp Arg Gln Ile Arg Asn Met Val Ile Phe Arg Asn Val Val Asp Gly
625                 630                 635                 640

Gln Pro Phe Thr Asn Trp Tyr Asp Asn Gly Ser Asn Gln Val Ala Phe
                645                 650                 655

Gly Arg Gly Asn Arg Gly Phe Ile Val Phe Asn Asn Asp Asp Trp Ser
            660                 665                 670

Phe Ser Leu Thr Leu Gln Thr Gly Leu Pro Ala Gly Thr Tyr Cys Asp
            675                 680                 685

Val Ile Ser Gly Asp Lys Ile Asn Gly Asn Cys Thr Gly Ile Lys Ile
    690                 695                 700

Tyr Val Ser Asp Asp Gly Lys Ala His Phe Ser Ile Ser Asn Ser Ala
705                 710                 715                 720

Glu Asp Pro Phe Ile Ala Ile His Ala Glu Ser Lys Leu
                725                 730
```